US008252912B2

(12) United States Patent
Ain et al.

(10) Patent No.: US 8,252,912 B2
(45) Date of Patent: Aug. 28, 2012

(54) TRANSCRIPTIONAL REPRESSION OF SODIUM-IODIDE SYMPORTER IN THYROID CARCINOMA

(75) Inventors: Kenneth Ain, Lexington, KY (US); Wei Li, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 524 days.

(21) Appl. No.: 12/081,790

(22) Filed: Apr. 21, 2008

(65) Prior Publication Data

US 2009/0191584 A1 Jul. 30, 2009

Related U.S. Application Data

(60) Provisional application No. 60/907,881, filed on Apr. 20, 2007.

(51) Int. Cl.
*C07H 21/02* (2006.01)

(52) U.S. Cl. ...................................................... 536/23.1

(58) Field of Classification Search .................. 536/23.1
See application file for complete search history.

(56) References Cited

U.S. PATENT DOCUMENTS 4,683,195 A 7/1987 Mullis et al.
2001/0053519 A1 * 12/2001 Fodor et al. ....................... 435/6

OTHER PUBLICATIONS

Abdelkarim et al "Protective effects of PF34, a novel, potent inhibitor of ply(ADP-ribos) polymeras (PARP) in in vitro and invivo models of stroke" pp. 225-260 International Journal of Molecular Medicine vol. 7, No. 3 Mar. 2001.

Kim et al "NAD+—Dependent Modulation of Chromatin Structure and Transcription by Nucleosome Binding Properties of PARP-1" pp. 803-814 Cell vol. 119, Dec. 17, 2004 Cell Press.

Virag et al "The Therapeutic Potential of Poly(ADP-Ribose) Polymerase Inhibitors" pp. 375-429 Pharmacological Reviews vol. 54 No. 3 The American Society for Pharmacology and Experimental Therapeutics 2002, Downloaded at Univ. of Kentucky on Aug. 6, 2008.

Krishnakumar et al "Reciprocal Binding of PARP-1 and Histone H1 at Promoters Specifies Transcriptional Outcomes" pp. 819-821 vol. 319, Science www.science.org Feb. 8, 2008. Downloaded at Univ. of Kentucky on Aug. 6, 2008.

Li et al "Protein Synthesis Inhibitors in Synergy with 5-Azacytidine, Restore Sodium/Iodine, Symporter Gene Expression in Human thyroid Adenoma Cell Line, KAK-1, Suggesting *Trans*-Active Transcriptional Repressor" pp. 1080-1087 The Journal of Clinical Endocrinology & Metabolism 92(3) Mar. 2007 The Endocrine Society Downloaded at Univ. of Kentucky on Aug. 6, 2008.

Ain et al "Somatostatin Analogs Affect proliferation of Human Thyroid Carcinoma Cell Lines in Vitro" pp. 1097-1102 The Journal of Clinical Endocrinology & Metablolism vol. 78, No. 5 1994 The Endocrine Society Downloaded at Univ. of Kentucky on Aug. 6, 2008.

Venkatarman et al "Restoration of Iodide Uptake in Dedifferentiated Thyroid Carcinoma: Relationship to Human $Na^+/I^-$ Symporter Gene Methylation Status" pp. 2449-2457 The Journal of Clinical Endocrinology & Metablolism vol. 84 No. 7 1999 The Endocrine Society Downloaded at Univ. of Kentucky on Aug. 6, 2008.

Schreiber et al "A Dominant-negative mutant of human poly(ADP-ribose) phymerase affects cell recovery, apoptosis, and sister chromatid exchange following DNA damage" pp. 4753-4757 Proc. Natl. Acad. Sci. USA vol. 92 May 1995.

Di Magliano et al "Pax8 has a key role in thyroid cell differentiation" pp. 13144-13149 PNAS www.pnas.org vol. 97, No. 24, Nov. 21, 2000.

Riedel et al "Post-transcriptional Regulation of the Sodium/ Iodide Symporter by Thyrotropin" pp. 21458-214463 The Journal of Biological Chemistry vol. 276, No. 24, Apr. 4, 2001, www.jbc.org Downloaded at Univ. of Kentucky on Aug. 6, 2008.

Simbulan-Rosenthal et al "PARP-1 binds E2F-1 Independently of its DNA binding and catalytic domains, and acts as a novel coactivator of E2F-1-mediated transcription during re-entry of quiescent cells into S-phase" pp. 8460-8471 Oncogene vol. 22 Jun. 19, 2003 The Nature Publishing group www.nature.com/onc.

Ain "Management of Undifferentiated Thyroid Cancer" pp. 1-16 Bailliere's Clinical Endocrinolgy and Metabolism vol. 14, No. 4 Hardcourt Publishers Ltd. 2000 http:/www.idealibrary.com.

Gadgil et al "Review: DNA Affinity Chromatography of Transcription Factors" pp. 147-178 Analytical Biochemistry vol. 290 Academic Press 2001 http://www.idealibrary.com Miyamoto et al "Inhibition of Nuclear Receptor Signaling by Poly(ADP-Ribose) Polymerase" pp. 2644-2649 Molecular and Clellular Biology vol. 19, No. 4 Apr. 1999 American Society for Microbiology.

Schreiber et al "Poly(ADP-ribose): novel functions for an old molecule" pp. 517-528 Nature Reviews: Molecular Cell Biology vol. 7 Jul. 2006 www.nature.com/reviews/molcellbio.

Schmitt et al Transcriptional Regulation of the Human Sodium/Iodine Symporter Gene by Pax8 and TTF-1. pp. 27-31 Exp. Clin. Endocrinol Diabetes 2001 vol. 109.

Zhang et al "Sequence-Specific Binding of poly(ADP-ribose) polymerase-1 to the Human T-cell Leukemia Virus Type-I Tax Responsive Element" pp. 107-116 Virology 2006 vol. 296.

Falek et al "Regulation of α-Synuclein Expression by Poly (ADP Ribose) Polymerase-1 (PARP-1) Binding to the NCAP-Repl Polymorphic Site Upstream of the SNCA Gene" pp. 478-492 American Journal of Human Genetics vol. 76 The American Society of Human Genetics 2005.

Robbins et al "Thyroid Cancer: A Lethal Endocrine Neoplasm" pp. 133-147 Annals of Internal Medicine vol. 115 No. 2 Jul. 1991.

(Continued)

*Primary Examiner* — J. E. Angell
(74) *Attorney, Agent, or Firm* — McDermott Will & Emery LLP

(57) ABSTRACT

The present disclosure relates to a sodium iodide symporter (NIS)-repressor binding site (NRBS) consisting of a DNA molecule spanning from −645 to −605 nucleotides (SEQ ID NO:4) or from −648 to −620 nucleotides (SEQ ID NO:5) upstream from the translation start site of human NIS gene. The disclosure further relates to a method of restoring iodide transport to a human thyroid carcinoma cell, including: the steps of: i) contacting the cell expressing and forming a NIS repressor protein complex capable of binding to the NRBS of the disclosure with a modulator of said complex, and ii) administering to the cell radiolabeled iodide.

7 Claims, 22 Drawing Sheets

OTHER PUBLICATIONS

Edwards et al "Special Report: Annual Report to the Nation on the Status of Cancer, 1975-2002, Featuring Population-Based Trends in Cancer Treatment" pp. 1407-1427 Journal of the Nation Cancer Institute, vol. 97 No. 19 Oct. 5, 2005.
Parkin et al "Global Cancer Statistics, 2002" pp. 74-108 A Cancer Journal for Clinicians vol. 55 No. 2 The American Cancer Society Mar./Apr. 2005 Downloaded from caonline.amcancersoc.org on Oct. 22, 2008.
Wu et al "Cancer incidence patterns among adolescents and young adults in the United States" pp. 309-320 Cancer Causes and Control vol. 16 Springer 2005.
Samaan et al "The Results of Various Modalities of Treatment of Well Differentiated Thyroid Carcinoma: A Retrospective Review of 1599 Patients" pp. 714-720 Journal of Clinical Endocrine Society and Metabolism vol. 75 No. 3 The Endocrine Society 1992 Downloaded from jcem.endojournals.org at Unv. Kentucky on Oct. 29, 2008.
Ain "Anaplastic Thyroid Carcinoma: A Therapeutic Challenge" pp. 64-69 Seminars in Surgical oncology vol. 16 Wiley-Liss. Inc. 1999.
Ain "Anaplastic Thyroid Carcinoma: Behavior, Biology, and Therapeutic Approaches" pp. 1-34, (1998).
Schlumberger et al Radioactive Iodine Treatment and External Radiotheraphy for Lung and Bone Metastases from Thyroid Carcinoma pp. 598-605 The Journal of Nuclear Medicine vol. 37 No. 4 Apr. 1996.
Kang et al "Combining Chromatin immunoprecipitations and DNA footprinting: a novel method to analyze protein-DNA interactions in vivo" pp. 1-5 Nucleic Acids Research vol. 30, No. 10, Oxford University Press 2002.
Kurreck et al "Design of antisense oligonucleotides stabilized by locked nucleic acids" pp. 1911-1918 Neucleic Acids Research vol. 30 No. 9 Oxford University Press 2002.
Tallet-Lopez et al "Antisense oligonucleotides targeted to the domain IIID of the hepatitis C virus IRES compete with 40S ribosomal subunit binding and prevent in vitro translation" pp. 734-742 Nucleic Acids Research vol. 31 No. 2 Oxford University Press 2003.
Sullivan et al "Hammerhead ribozymes designed to cleave all human rod opsin mRNAs wich cause autosomal dominant reinitis pigmentosa" pp. 102-113 Molecular Vision 2002 vol. 8 Apr. 8, 2002.
Wang et al "A General Approach for the Use of Oligonucleotides Effectors to Regulate the Catalysiss of RNA-Cleaving Ribozymes and DNAzymes" pp. 1735-1742 Nucleic Acids Research vol. 30 No. 8 Oxford University Press Feb. 18, 2002.
Mackay et al "Characterization of Potent and Specific Class of Antisense Olingonucleotide Inhibitor of Human Protein Kinase C-α Expression" pp. 1715-1722 Journal of Biological Chemistry vol. 274 No. 3 The American Society for Biochemistry and Molecular Biology, Inc. Jan. 15, 1999. http://www.jbc.org.
Schumacher et al "Exposure of Human Vascular Smooth Muscle Cells to Raf-1 Antisense Oligodeoxynucleotides: Cellular Responses and Pharmacodynamic Imlications" pp. 97-104 Molecular Pharmacology vol. 53 The American Society for Pharmacology and Experimental Therapeutics 1998 http://www.molopharm.org Downloaded at Univ of Kentucky Oct. 22, 2008.
Hicke et al "Tenascin-C Aptamers are Generated Using Tumor Cells and Purified Protein" pp. 48644-48654 The Journal of Biological Chemistry vol. 276, No. 52 The American Society of Biochemistry and Molecular Biology Inc. Dec. 28, 2001.
Rhodes et al "The Generation and Characteristics of Antagonist RNA Aptamers to Human Oncostatin M" pp. 28555-28561 The Journal of Biological Chemistry vol. 275, No. 37 The American Society of Biochemistry and Molecular Biology, Inc. Sep. 15, 2000 http://www.jbc.org Downloaded at Univ of Kentucky on Oct. 29, 2008.
Giovannangeli et al "Accessibility of Nuclear DNA to triplex-forming oligonucleotides: the integrated HIV-1 Provirus as a target" pp. 79-84 Proc. Natl. Acad. Sci. USA vol. 94 Jan. 1997 http://www.pnas.org.
McGuffie et al "Antigene and Antiproliferatiive Effects of a c-myc-trageting Phosphorothioate Triple Helix-forming Oligonucleotide in Human Leukemia Cells" pp. 3790-3797 Cancer Research vol. 60 Jul. 15, 2000.
Zhou-Sun et al "A Physico-chemical Study of Triple Helix Formation by an Oligodeoxythymidylate with N3'—>P5' Phosophoramidate Linkages" pp. 1782-1787 nucleic Acids Research vol. 25 No. 9 Oxford University Press 1997.
D'Add et al "Functions of poly(ADP-ribose) polymerase in Controlling telomere length and chromosomal stability" pp. 76-80 Nature Genetics vol. 23 Nature America Inc. Sep. 1999 http://genetics.nature.com.
Wagner "Potent and Selective Inhibition of Gene Expression by an antisense Heptanucleotide" pp. 840-844 Nature Biotechnology vol. 14 Nature Publishing Group Jul. 1996 http://www.nature.com/naturebiotechnology.
Beigelman et al "Synthesis of 2'-modified nucleotides and their incorporation into hammerhead ribozymes" pp. 4434-4442 Nucleic Acids Research vol. 23 No. 21 Sep. 19, 1995.
Morishita et al "Application of Transcription Factor 'Decory' Strategy as Means of Gene Therapy and Study of Gene Expression in Cardiovascular Disease" pp. 1023-1028 Circulation Research: Journal of the American Heart Association vol. 82 The American Heart Association 1998 Downloaded at Univ Kentucky Nov. 10, 2008.
Peele et al "Characterization and Use of Green Fluorescent Proteins from *Renilla mulleri* and *Ptilosarcus guernyi* for the Human Cell Display of Functional Peptides" pp. 507-519 Journal of Protein Chemistry vol. 20. No. 6 Aug. 2001 Plenum Publishing Corporation.
Matz et al "Fluorescent proteins from Nonbioluminescent Anthozoa Species" pp. 969-973 Nature Bioltechnology vol. 17 Oct. 1999 Nature American Inc. http://biotch.nature.com.
Gilbert et al "D-Valine as a Selective Agent for Normal Human and Rodent Epithelial Cells in Culture" pp. 11-17 Cell vol. 5 May 1975 MIT.

* cited by examiner

SEQ ID NO:1

The proximal promoter region of human NIS gene (Sodium/iodide symporter, SLC5a5):

5'GGAGACGGGGTCTTGCTGTGCTGCCCAGGCTGGAGTGCTGTGCAGTTCTCGACCACAGCTCATTGCAGCCTCGAACTTC
CACGCTCAAGCGATCCTCCCACTTCAGCCTTCTGAGTAGCTGGGATTACAGGCATGTGCCACCACGCCTCGCTAATATTG
TATTTTTCATACAGACAAGATCTCACTATGTTGCTCAGGGTAGTCTCGAATTCTGGGACTCAAATGATCCTCCCACTTCA
GCCTCCCAAAGTGCTGGGATTACAGGCATAAGCCATCATGCCCGGCCTCTGACGCTGTTTCTTTCAACCCCCAGGATTTC
AGATTCCACCAGCTTATGGAGAAGGGAACCAAGTTTGAGATGCGTGATTGCCCAGAAAGTTGGAGGCTGAGCTGAGACTT
GAACCCAGAGACCAGAACCTCCAGAGGTCAAAGTCCTCCTGGGTCCCCCAGAGAAGGGCCCTGAGATGACAGCTCGTTGG
TCCTCATGGAAGCGTGACCCCCCCAGTAGACTTTCTCCCACACCCAACCTTGGTTTCCTCATCTATATGATAGGGACAAG
CCAGACTCTACCTCCCTGGTGGTCATGGTCTCCGCTTATTCGGGTTCATAACCTTAAAGGCCCCTCGCACCACCTCAGTG
AGCCATTTATGCCTGGCACAGGGCCAACTCTCAGTGCATATCTGCAAAGGAACCAATGAATGAATGAATGAAGTGACAAA
TGAATAAAGGAATAAATGAATGAGGCACTTATCATGTACCAGGCTTTCGTTACCACGTCCCATTTATTCCTCTGAGGCAG
GGTCTATTTTATCCTTGTTACAGATGGGGAAACTAAGGCCCAGGGAGGAGCAAAGTCTTCCCCAAGTATGTACCCACTCA
GAACTTGAGCTCTGAATGTCTCCCACCCAGCTTAGCCCAAGAGCGGGGTTCAGTGATGCCCACCCCCTAAGGCTCTAGAG
AAAGGGGGTAGGCCCACATGCCAGTTTGGGGGTGGTAAAGCCAGGTAAGTTTTCTTTATGGGTCCCCTGAAACCCTGAAA
GTGAACCCCAGTCCTGCATGAAAGTGAGCTCCCCATAGCTCAAGGTATTCAAGCACAATACGGCTTTGAGTGCTGAAGCA
GGCTGTGCAGGCTTGGATAGTGACATGCCCTTTTTGAGCCTCAATTTCCCCACCTGTCAACAGCAGACAGTGACAGCTGT
GATCAGGGGATCACAGTGCATGGGGATGGGTGTGTGCATGGGGATGGAGGGGCATTTGGGAGCCCTCCCCGATACCACCC
CCTGCAGCCACCCAGATAGCCTGTCCTGGCCTGTCTGTCCCAGTCCAGGGCTGAAAGGGTGCGGGTCCTGCCCGCCCCTA
GGTCTGGAGGCGGAGTCGCGGTGACCCGGGAGCCCAATAAATCTGCAACCCACAATCACGAGCTGCTCCCGTAAGCCCCA
AGGCGACCTCCAGCTGTCAGCGCTGAGCACAGCGCCCAGGGAGAGGGACAGACAGCCGGCTGCATGGGACAGCGGAACCC
AGAGTGAGAGGGGAGGTGGCAGGACAGACAGACAGCAGGGGCGGACGCAGAGACAGACAGCGGGGACAGGGAGGCCGACA
CGGACATCGACAGCCCATAGATTCCTAACCCAGGGAGCCCCGGCCCCTCTCGCCGCTTCCCACCCCAGACGGAGCGGGGA
CAGGCTGCCGAGCATCCTCCCACCCGCCCTCCCCGTCCTGCCTCCTCGGCCCCTGCCAGCTTCCCCCGCTTGAGCACGCA
GGGCGTCCGAGGACGCGCTGGGCCTCCGCACCCGCCCTC*ATG* 3'

Figure 2

#1 #2 #3 #4 #5
[TAGCTC]AAGG[TATTCA]AGCACAAT[ACGGCT]TTGA[GTGCTG]AAGC[AGGC
aaaaa aaaaaa aaaaaa aaa aaaaa

#6 #7 #8 #9 #10
TG]TGCA[GGCTTG]GATA[GTGACA]T[GCCCTT]TTT[GAGCCT]CAATTT[CCCC
aaaaaa aaa aaaaaa aaaa aaaaaa

#11 #12 #13 #14 #15 #16
AC][CTGTCA]A[CAGCAG]ACA[GTGACA][GCTGTG]AT[CAGGGG]AT[CACAGT
aaaaaa aaa aaaaaa aaa aaa aaaa

#17 #19 #20 #21 #22 #23
][GCATGG]GGATGG[GTGTGT][GCATGG][GGATGG][AGGGGC]ATTT[GGGAG
aaaaaa aaaaaa aaaa aaaaaa aaaaaa aaaaaa

C]CCT (SEQ ID NO:2)

SEQ ID NO:3

5'TAGCTCAAGGTATTCAAGCACAATACGGCTTTGAGTGCTGAAGCAGGCT
GTGCAGGCTTGGATAGTGACATGCCCTTTTT*GAGCCTCAATTTCCCCACC*
*TGTCAACAGCAGACAGTGACAG*CTGTGATCAGGGGATCACAGTGCATGGG
GATGGGTGTGTGCATGGGGATGGAGGGGCATTTGGGAGCCCTCCCCGATA
CCACCCCCTGCAGCCACCCAGATAGCCTGTCCTGGCCTGTCTGTCCCAGT
CCAGGGCTGAAAGGGTGCGGGTCCTGCCCGCCCCTAGGTCTGGAGGCGGA
GTCGCGGTGACCCGGGAGCCCAATAAATCTGCAACCCACAATCACGAGCT
GCTCCCGTAAGCCCCAAGGCGACCTCCAGCTGTCAGCGCTGAGCACAGCG
CCCAGGGAGAGGGACAGACAGCCGGCTGCATGGGACAGCGGAACCCAGAG
TGAGAGGGGAGGTGGCAGGACAGACAGACAGCAGGGGCGGACGCAGAGAC
AGACAGCGGGGACAGGGAGGCCGACACGGACATCGACAGCCCATAGATTC
CTAACCCAGGGAGCCCCGGCCCCTCTCGCCGCTTCCCACCCCAGACGGAG
CGGGGACAGGCTGCCGAGCATCCTCCCACCCGCCCTCCCCGTCCTGCCTC
CTCGGCCCCTGCCAGCTTCCCCCGCTTGAGCACGCAGGGCGTCCGAGGAC
GCGCTGGGCCTCCGCACCCGCCCTC*ATG* 3'

B

SEQ ID NO:4

5'GAGCCTCAATTTCCCCACCTGTCAACAGCAGACAGTGACAG 3'

C

SEQ ID NO:5

5' TTTGAGCCTCAATTTCCCCACCTGTCAAC 3'

Figure 22

TRANSCRIPTIONAL REPRESSION OF SODIUM-IODIDE SYMPORTER IN THYROID CARCINOMA

This patent application claims the priority benefit under 35 U.S.C. §119(e) to provisional application No. 60/907,881, filed Apr. 20, 2007, the content of which is incorporated by reference as if recited herein in its entirety.

STATEMENT OF GOVERNMENT SUPPORT

This disclosure was made, in part, with support from the Merit Review award program of the U.S. Department of Veterans Affairs, and the government may have certain rights in this disclosure.

FIELD OF THE DISCLOSURE

This disclosure relates to compounds, compositions, kits and methods of restoring iodide transport in cells defective in iodine transport. The present disclosure is further directed to a method of treating tumors by antagonizing the elements that repress the iodide transport in a cancerous cell.

BACKGROUND OF THE DISCLOSURE

Thyroid cancer is now increasing in incidence in the United States more rapidly than any other cancer in both men and women (Edwards et al. 2005 J Natl Cancer Inst 97:1407-1427). The American Cancer Society estimates that, in the United States, 25,690 people (6,500 men and 19,190 women) were diagnosed with and 1,490 people died of cancer of the thyroid in 2005 with prevalence exceeding 327,000 in 2002. Global data from 2002 show an incidence of 141,000 new cases (Parkin et al. 2002. *CA Cancer J Clin* 55:74-108). Age-specific incidence rates reveal thyroid cancer to have a higher incidence than all other cancers in white women between the ages of 20 to 30 (Wu et al. 2005 *Cancer Causes Control* 16:309-320). The most current SEER Data (National Cancer Institute, Bethesda, Md.; posted 2006) evaluating trends in cancer incidence and death from 1994 to 2003 documents thyroid carcinoma exceeding all other cancers in rate of increased incidence and second only to liver/intrahepatic bile duct cancers in rate of increased death. This most rapid rate of incidence increase for thyroid cancer is seen both in people over 65 yrs and under 65 yrs of age and in both men and women.

Radioiodide is a "magic bullet" for systemic therapy of thyroid carcinoma. Radioiodine treatment is an effective post-surgical therapy with unique specificity for differentiated thyroid carcinoma cells that retain the ability to concentrate iodine (DeGroot et al. 1994 *Wold J Surg* 18:123-130; Mazzaferri et al. 1994 *Am J Med* 97:418-428; Samaan et al. 1992 *J Clin Endocrinol Metab* 75:714-720; Simpson et al. 1988 *Int J Rad One Biol Phys* 14:1063-1075; Wong et al. 1990 *Endocrinol Metab Clin N Amer* 19:741-760). Successful destruction of malignant thyroid cells requires delivery of a sufficient total radiation dosage using $I^{131}$ while at a dose rate of 0.6 to 3.0 Gy/h in order to prevent cellular repair of sublethal radiation damage. The efficacy of this treatment requires thyroid cancer cells to manifest "differentiated" functional abilities. Differentiated functions include: expression and membrane-localization of the sodium/iodide symporter (NIS) enabling intracellular concentration of radioiodide, expression of thyrotropin (TSH) receptors (permitting both stimulation of the cell and increased hNIS production by raising TSH levels and suppression of the cell by decreasing TSH levels), organification of internalized iodide (enhancing radioiodide retention and radiation dose delivery), and production of thyroglobulin (clinically useful as a specific tumor marker in thyroidectomized patients).

NIS actively transports iodide into thyroid follicular cells against an electrochemical gradient, by a factor of 20-40, for organification by thyroid peroxidase in the cell. This process is stimulated by thyrotropin (TSH) and powered by $Na^+/K^+$-ATPase. Normal thyroid, stimulated by TSH, concentrates $I^{131}$ (uptake) to 1% of administered dose/gram tissue. Differentiated thyroid cancer metastases typically concentrate $I^{131}$ at 0.06 to 0.3% of administered $I^{131}$ dose/gram tumor (3-17-fold less than normal thyroid tissue).

Undifferentiated and dedifferentiated thyroid carcinoma, however, constitute a broad spectrum of tumors that show varying degrees of differentiated function and clinical aggressiveness. This is epitomized by anaplastic carcinomas with median survival measured in months despite the most assertive therapeutic efforts (Ain K B 1999 Seminars in surgical oncology 16:64-69; Ain K B 1998 *Thyroid* 8:715-726). Despite the fact that fewer than 400 new cases of anaplastic thyroid carcinoma are expected in North America each year, thousands of patients will manifest poorly differentiated metastatic thyroid cancers with sufficient loss of differentiated function to make classical treatment with radioactive iodine ineffectual, constituting at least one third of patients with distant metastases (Schlumberger et al. 1996 *J Nucl Med* 37:598-605). In most cases, the failure of radioiodine treatment is due to loss of NIS function, which ultimately result in ≈10% of patients die (Robbins et al. 1991 *Ann Int Med* 115:133-147).

Therefore, there exists a need for restoring the expression or function of NIS in thyroid cancer cells to facilitate the uptake and/or retention of radioactive iodine in such cells in which NIS expression and/or function is reduced or lost.

SUMMARY OF THE DISCLOSURE

One aspect of the disclosure relates to a sodium iodide symporter (NIS)-repressor binding site (NRBS) selected from the group consisting of a DNA molecule spanning from −645 to −605 nucleotides upstream from the translation start site of human NIS gene (SEQ ID NO:4), a DNA molecule spanning from −648 to −620 nucleotides upstream from the translation start site of human NIS gene (SEQ ID NO:5), and nucleic acid sequence having at least 85% sequence identity thereto.

Another aspect of the disclosure relates to a method of restoring iodide transport to a human thyroid carcinoma cell, including: the steps of: i) contacting the cell expressing and forming a NIS repressor protein complex capable of binding to the NRBS of the disclosure with a modulator of said complex, and ii) administering to the cell radiolabeled iodide.

Another aspect of the disclosure relates to a method of restoring iodide transport to an undifferentiated or dedifferentiated thyroid carcinoma cell, including: contacting said cell with a modulator of a PARP-1 protein, and administering to the cell radiolabeled iodide.

Another aspect of the disclosure relates to a method of restoring iodide transport to a human thyroid carcinoma cell, including: the steps of: i) contacting the cell expressing and forming a NIS repressor protein complex capable of binding to the NRBS of the disclosure with a modulator of said NRBS, and ii) administering to the cell radiolabeled iodide.

Another aspect of the present disclosure relates to a method of screening for a therapeutic agent capable of restoring NIS gene expression and radioiodine uptake in a thyroid cancer cell, including: the steps of: i) contacting the cell with a pharmacologic antagonist against one or more components of an NIS repressor protein complex capable of binding to the NRBS of the disclosure, ii) detecting NIS expression or radioiodine uptake by the cell; wherein an increase in the NIS expression or radioiodine uptake by the cell indicates that said agent is capable of restoring radioiodine uptake.

Another aspect of the disclosure relates to a kit for restoring iodide transport to a human thyroid carcinoma cell, including: a therapeutic agent capable of antagonizing the association between the NRBS of the disclosure and one or more components of a NIS repressor protein complex, and a radiolabeled iodide.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

The accompanying drawings, which are incorporated in and constitute a part of this specification, illustrate one (several) embodiment(s) of the disclosure and together with the description, serve to explain the principles of the disclosure.

BRIEF DESCRIPTION OF THE DRAWINGS

FIG. 2 shows the sequences for the proximal promoter region of human sodium/iodide symporter gene (NIS, SLC5a5) (SEQ ID NO:1). The bold italic letters ATG designate the translation start codon for human NIS protein, the A is assigned +1. The underlined bold letter G is the transcription initiation site for human NIS gene, based on the genomic sequence for human chromosome 19 from NCBI website, and is −348 relative to the A+1. All the sequences of the probes used in the electrophoretic mobility shift assays (EMSA) and the luciferase reporter assays are numbered based on this sequence and numbering system.

FIG. 6 shows the DNA sequence from −724 to −534 bp of hNIS promoter (SEQ ID NO: 2) with the numbers above the sequence indicating the mutations and the square brackets enclosing the original promoter sequences, the sequences in lower case below each square bracket showing the mutated sequence (SEQ ID NO:152).

radio-labeled Probe A only; Lane-2 & 3: hot Probe A plus KAK-1 nuclear extract with and without 60× cold Probe A: Lane-4: hot Probe A plus KAK-1 nuclear extract with 60× cold Comp-1 as competitor; Lane-5: hot Probe A plus KAK-1 nuclear extract with 60× cold Comp-2 as competitor; Lane-6: hot Probe A plus KAK-1 nuclear extract with 60× cold Comp-0.9 as competitor; Lane-7: hot Probe A plus KAK-1 nuclear extract with 60× cold Comp-1.1 as competitor; Lane-8: hot Probe A plus KAK-1 nuclear extract with 60× cold Comp-1.2 as competitor; Lane-9: hot Probe A plus KAK-1 nuclear extract with 60× cold Comp-1.3 as competitor; Lane-10: hot Probe A plus KAK-1 nuclear extract with 60× cold Comp-1.4 as competitor.

Figure 13:
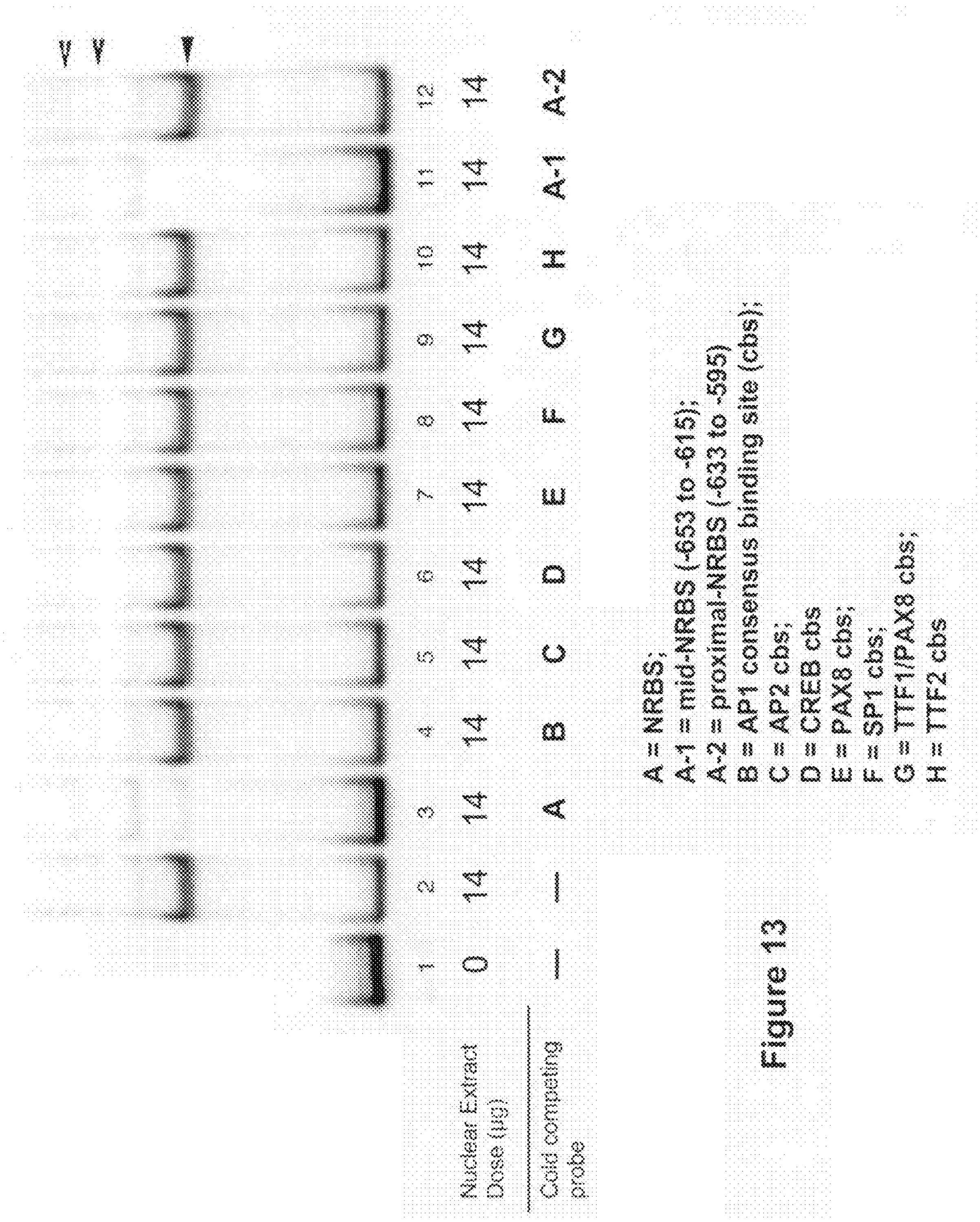

FIG. 13 shows the EMSA results using radio-labeled EMSA probe-A, nuclear extract from KAK-1 cells cultured under basal condition and cold annealed double strand oligos containing corresponding DNA-binding sites for several transcriptional factors. Lane-1: hot EMSA probe-A; Lane-2: hot probe-A mixed with 14 μg nuclear extract from KAK-1 cells cultured under basal condition; Lane-3: mixture in Lane-2 plus 20-fold cold probe-A; Lane-4 to 10: mixture in Lane-2 plus 90-fold cold annealed doubled strand oligos containing AP-1, AP-2, CREB, Pax-8, SP-1, TTF-1/Pax-8, TTF-2 DNA-binding site, respectively; Lane-11, 12: mixture in Lane-2 plus 90-fold cold annealed double strand EMSA competitor oligo-1 and oligo-2, respectively. The results indicated that the protein factor(s) resulting in the shifted bands do not involve AP-1, AP-2, CREB, Pax-8, SP-1, TTF-1, TTF-2. The binding site for the protein factor(s) is in EMSA competitor oligo-1, corresponding to −653 to −615 base pair in the human NIS proximal promoter region. The arrows point to the mobility shifted bands, which are EMSA probe-A-specific.

Figure 14:
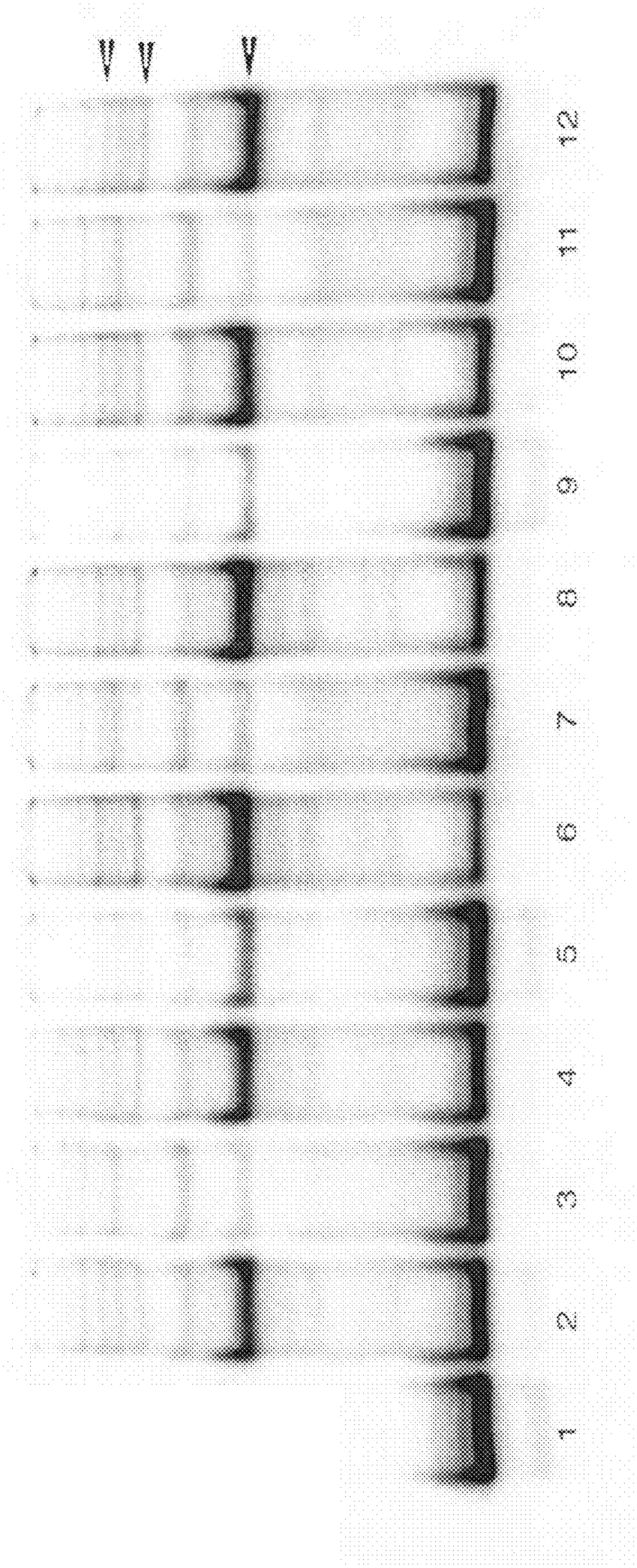

FIG. 14 shows the results of EMSA using radio-labeled EMSA probe-A, nuclear extracts from KAK-1 cells and NPA-87 cells cultured under basal condition, and cold annealed double strand oligo containing SP-1 DNA-binding site. Lane-1: hot probe-A; Lane-2: hot probe-A mixed with 14 μg of nuclear extract from KAK-1 cells cultured under basal condition; lane-3: mixture in Lane-2 plus 20-fold cold probe-A; Lane-4: mixture in Lane-2 plus 90-fold cold annealed oligo containing SP-1 DNA-binding site; lane-5, 6: hot probe-A mixed with 8 and 23 μg new batch of nuclear extract from KAK-1 cells cultured under basal condition, respectively; Lane-7: mixture in Lane-6 plus 20-fold cold probe-A; Lane-8: mixture in Lane-6 plus 90-fold cold annealed oligo containing SP-1 DNA-binding site; Lane-9, 10: hot probe-A mixed with 7 and 21 μg of nuclear extract from NPA-87 cells cultured under basal condition; Lane-11: mixture in Lane-10 plus 20-fold cold probe-A; Lane-12: mixture in Lane-10 plus 90-fold cold annealed oligo containing SP-1 DNA-binding site. The arrows point to the mobility shifted bands, which are EMSA probe-A-specific. These results indicate that the protein factor(s) in KAK-1 cells resulting in the shifted bands also exist in NPA-87 cells.

Figure 15:
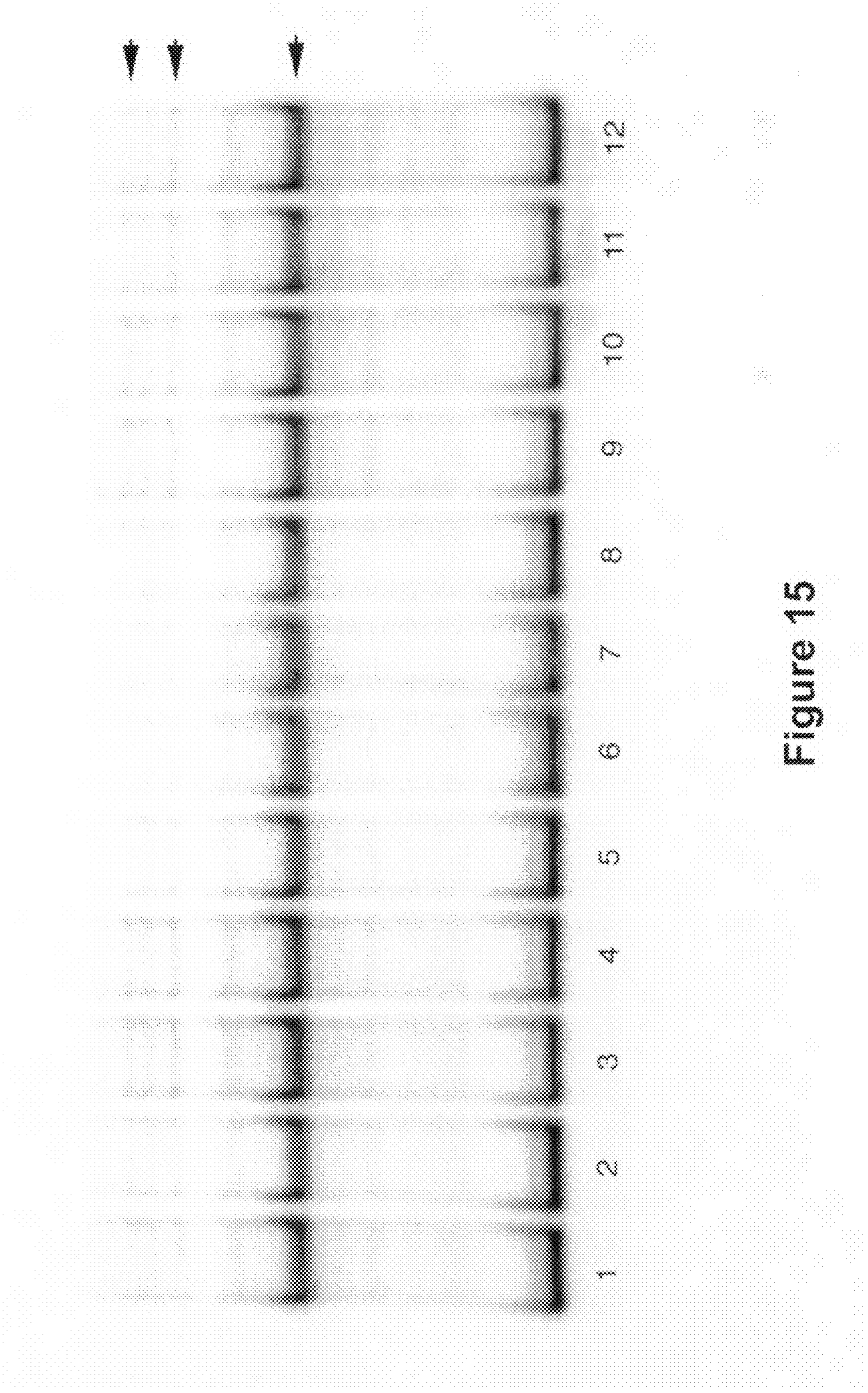

FIG. 15 is the EMSA results using radio-labeled EMSA probe-A, nuclear extracts from KAK-1 cells cultured under basal condition and KAK-1 cells cultured under basal condition supplemented with azaC (0.5 μM), NaB (1 mM), azaC plus NaB, CHX (10 μg/ml), azaC plus CHX for 2 days, respectively. Lane-1, 2: hot probe-A mixed with 17 μg nuclear extract from KAK-1 cells cultured under basal condition; Lane-3, 4: hot probe-A mixed with 17 μg nuclear extract from KAK-1 cells cultured under basal condition supplemented with azaC (0.5 μM); Lane-5, 6: hot probe-A mixed with 17 μg nuclear extract from KAK-1 cells cultured under basal condition supplemented with NaB (1 mM); Lane-7, 8: hot probe-A mixed with 17 μg nuclear extract from KAK-1 cells cultured under basal condition supplemented with azaC plus NaB; Lane-9, 10: hot probe-A mixed with 17 μg nuclear extract from KAK-1 cells cultured under basal condition supplemented with CHX (10 μg/ml); Lane-11, 12: hot probe-A mixed with 17 μg nuclear extract from KAK-1 cells cultured under basal condition supplemented with azaC plus CHX. The arrows point to the mobility shifted bands, which are EMSA probe-A-specific.

Figure 16:
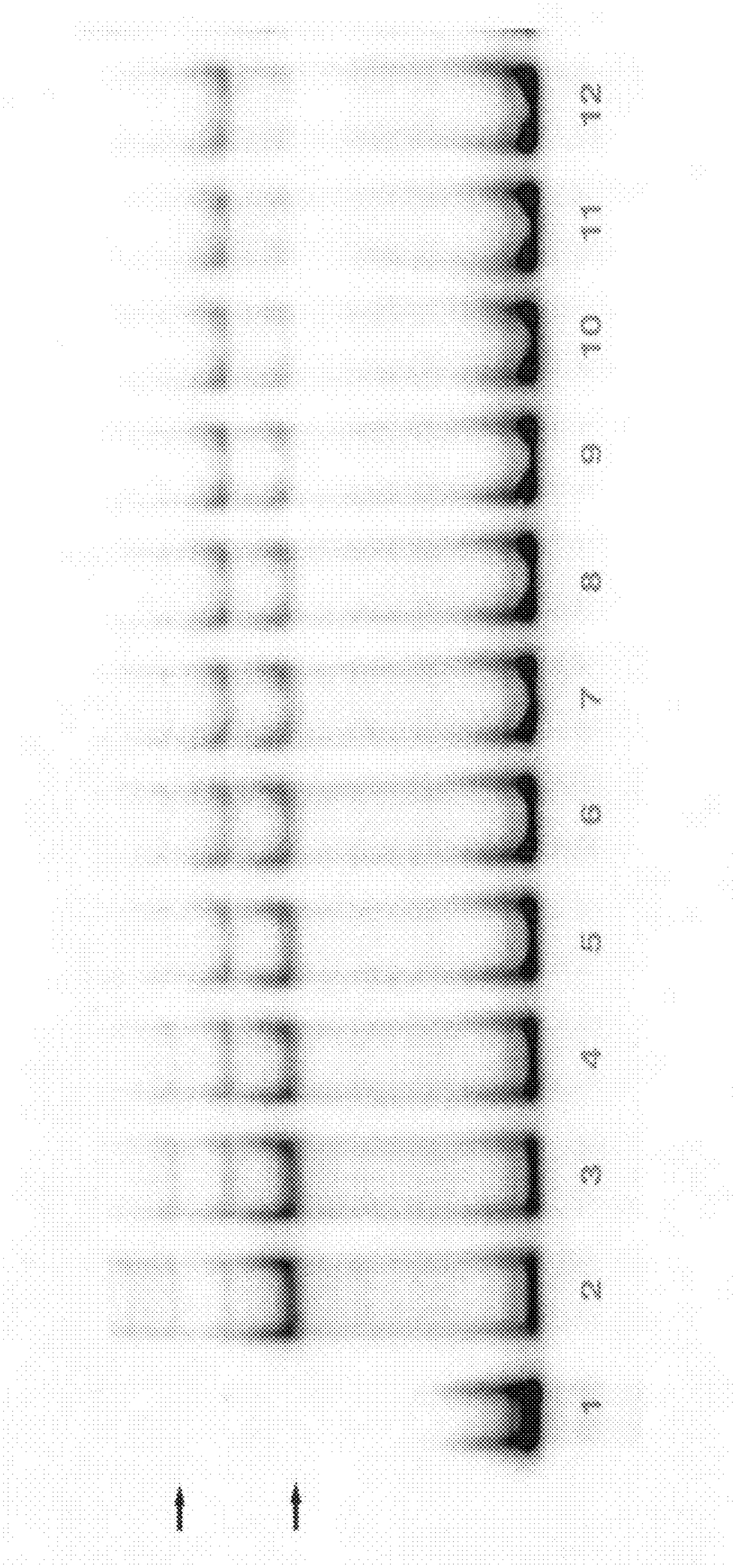

FIG. 16 is a gel showing the EMSA results using radio-labeled EMSA probe-A and nuclear extract from KAK-1 cells cultured under basal condition and having increased KCl concentration in the EMSA buffer system to show the influence of KCl on the probe-A-specific mobility shift pattern. Lane-1: hot probe-A; Lane-2: EMSA using hot probe-A and 20 μg nuclear extract from KAK-1 cultured under basal condition in 1×EMSA buffer system (100 mM KCl, 20 mM HEPES, 0.2 mM EDTA, 0.5 mM DTT, 125 μg/ml sonicated Salmon sperm DNA, 0.5 U/ml poly dI:dC); Lane-3: the mixture in Lane-2 plus 0.1 M KCl; Lane-4: the mixture in Lane-2 plus 0.2 M KCl; Lane-5: the mixture in Lane-2 plus 0.3 M KCl; Lane-6: the mixture in Lane-2 plus 0.4 M KCl; Lane-7: the mixture in Lane-2 plus 0.5 M KCl; Lane-8: the mixture in Lane-2 plus 0.6 M KCl; Lane-9: the mixture in Lane-2 plus 0.7 M KCl; Lane-10: the mixture in Lane-2 plus 0.8 M KCl; Lane-11: the mixture in Lane-2 plus 0.9 M KCl; Lane-12: the mixture in Lane-2 plus 1 M KCl. The arrows point to the mobility shifted band, which are EMSA probe-A-specific.

Figure 17:
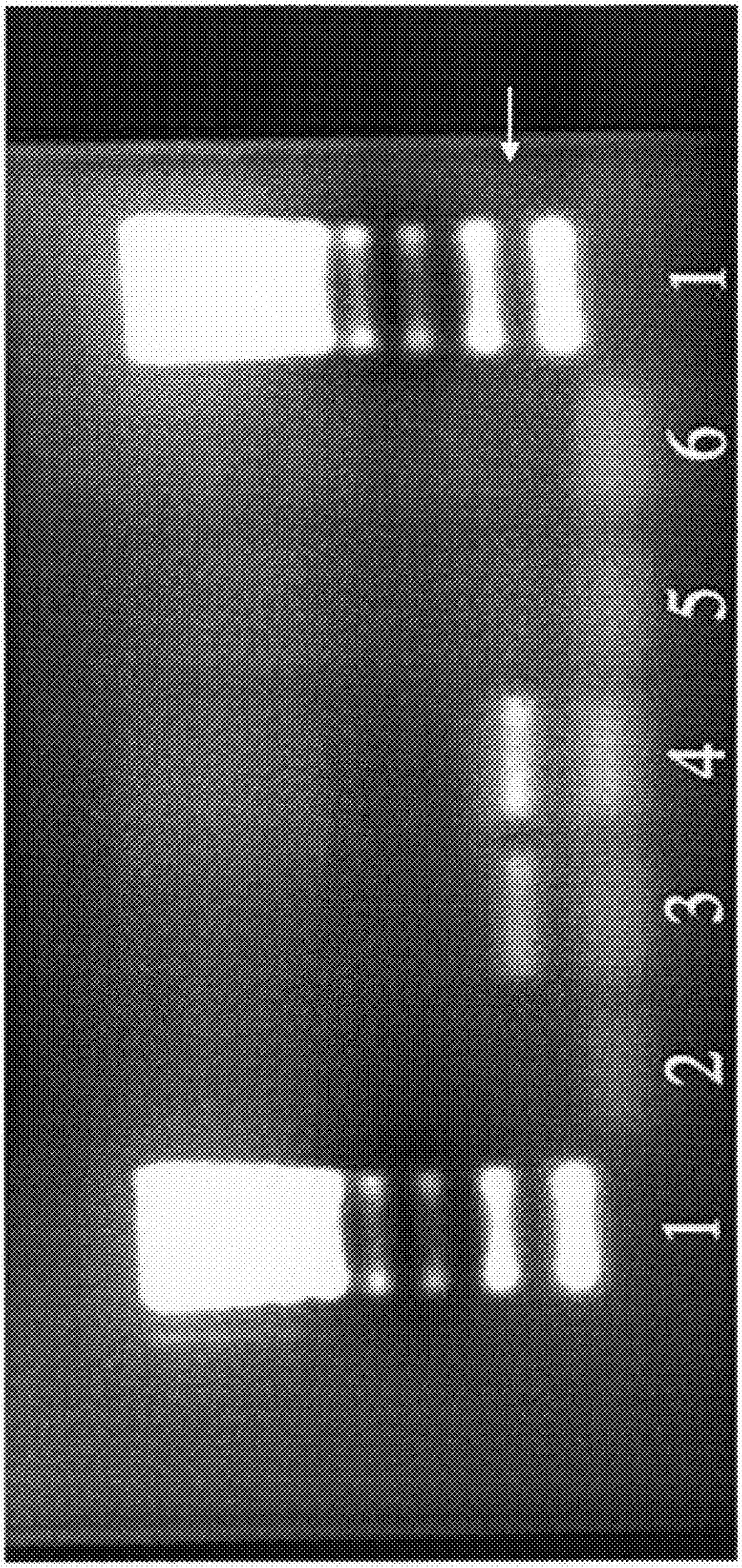

FIG. 17 shows the results of the chromatin immunoprecipitation assay in which the interaction between human PARP-1 and human NIS-repressor binding site (NRBS) is interrogated by PCR using NRBS-F and NRBS-R primer pair flanking NRBS. As shown in this figure, PCR products are resolved in a 1.5%-agarose gel. The arrow points to a positive PCR amplification of the NRBS DNA fragment of 191 bp in length in lanes 3 and 4. Lane-1: 100 bp DNA ladder; Lane-2: anti-Actin antibody is used in immunoprecipitation; Lane-3: anti-human PARP-1 antibody from R&D Systems® is used in immunoprecipitation; Lane-4: anti-human PARP-1 antibody from Roche® is used in immunoprecipitation; Lane-5: the genomic Input DNA is used as template in PCR; Lane-6: anti-RNA polymerase II antibody in ChIP-IT™ kit from Active Motifis® is used in immunoprecipitation.

Figure 18:
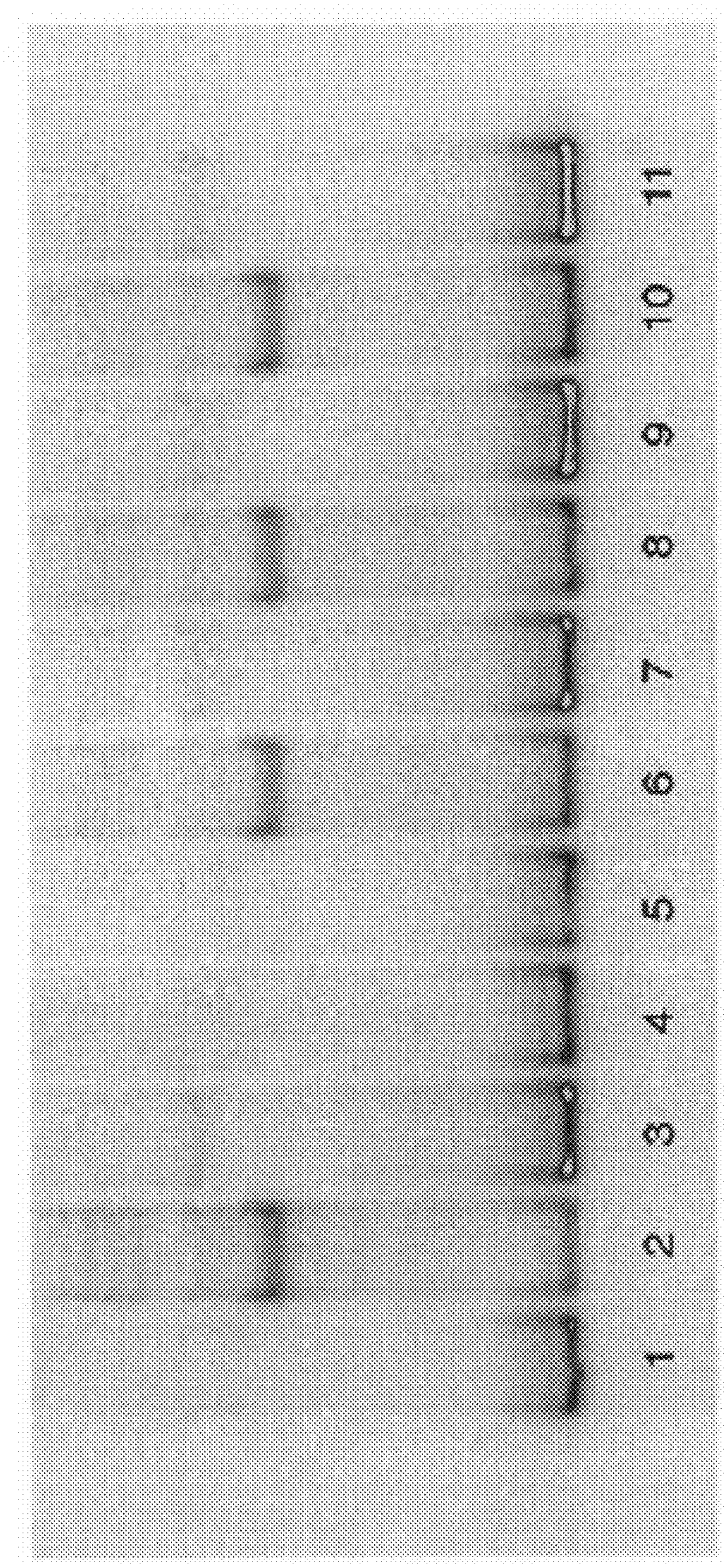

FIG. 18 shows the EMSA analysis of commercial hPARP-1 and the nuclear extracts prepared from KAK-1 cells stably transfected with the control pCR3.1 plasmid or the expression plasmid expressing the DNA-binding domain of human PARP-1. The protein samples are indicated as follows: Lane-1: radiolabeled Probe A only, Lane-2 & 3: nuclear extract prepared from KAK-1 cells in the absence or presence of 50× cold Probe A as competitor; Lane-4 & 5: 1.5 μg commercial hPARP-1 from Trevigen in the absence or presence of 50× cold Probe A as competitor; Lane-6 & 7: nuclear extract prepared from DBD/pCR3.1-transfected KAK-1 cells in the absence or presence of 50× cold Probe A as competitor; Lane-8 & 9: nuclear extract prepared from pCR3.1-transfected KAK-1 cells in the absence or presence of 50× cold Probe A as competitor; Lane-10 & 11: nuclear extract from DBD/pCR3.1-transfected KAK-1 clone #C cells, which had strong expression for the DBD domain of hPARP-1 as detected by western blotting, in the absence or presence of 50× cold Probe A as competitor. The arrows point to the Probe A-specific gel-shift bands.

Figure 19:
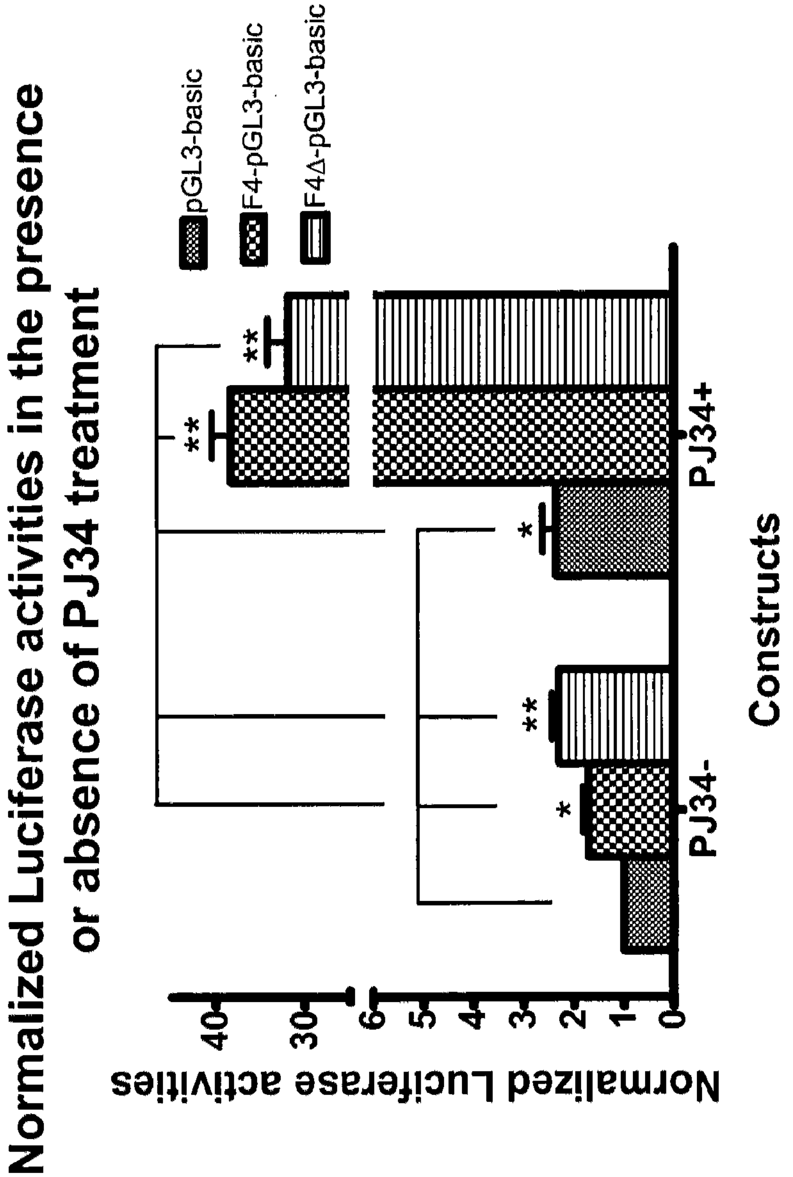

FIG. 19 shows the luciferase activities from 3 hNIS promoter reporter constructs with or without treatment with PJ34 at 30 μM for 2 days were determined and normalized with Rennilar luciferase activities respectively for transfection efficiency, followed by normalization to the luciferase activity of pGL3-basic vector in the absence of PJ34 treatment. Experiments were triplicates. The luciferase activities were analyzed using paired one-tail t-test. * indicates $p<0.05$, ** indicates $p<0.01$.

Figure 20:
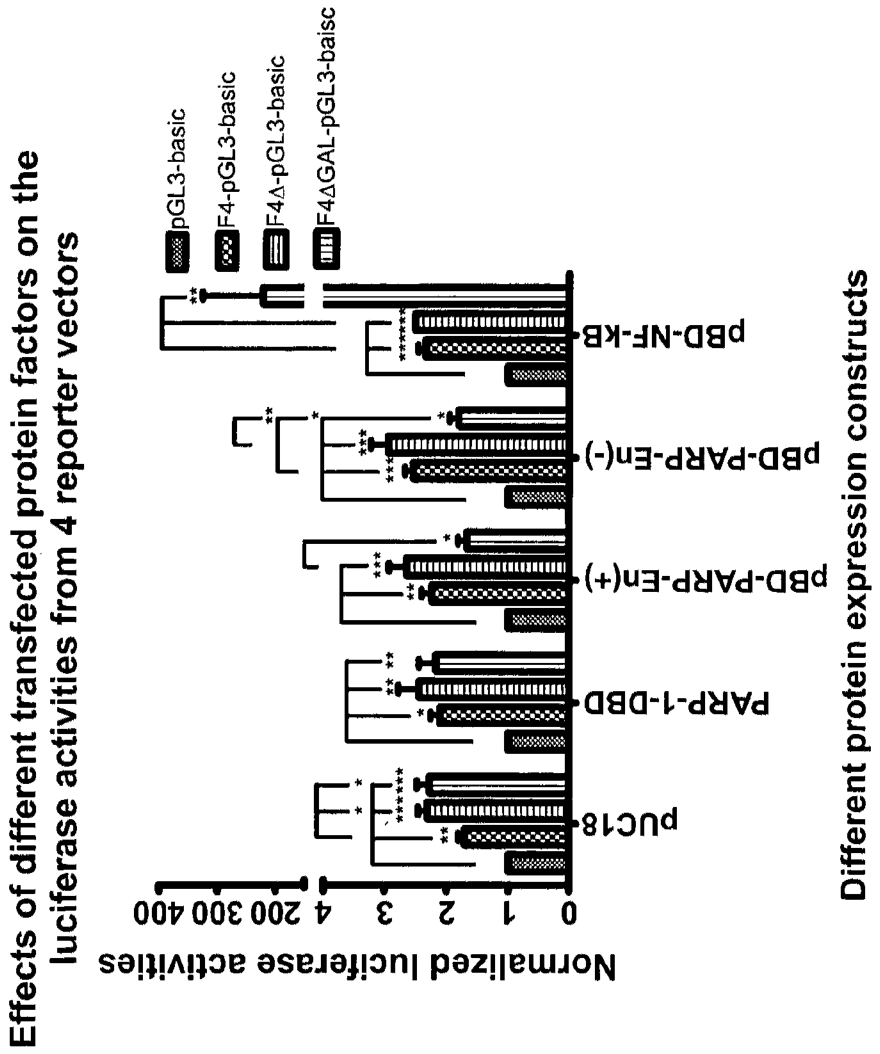

FIG. 20 shows the results of twenty DNA transfection mixtures being transiently transfected into KAK-1 cells. The luciferase activities were determined and normalized with Rennilar luciferase activities respectively for transfection efficiency, followed by normalization to the luciferase activity from pGL3-basic vector within the respective group. Experiments were triplicates. The luciferase activities were analyzed using paired one-tail t-test.

Figure 21:
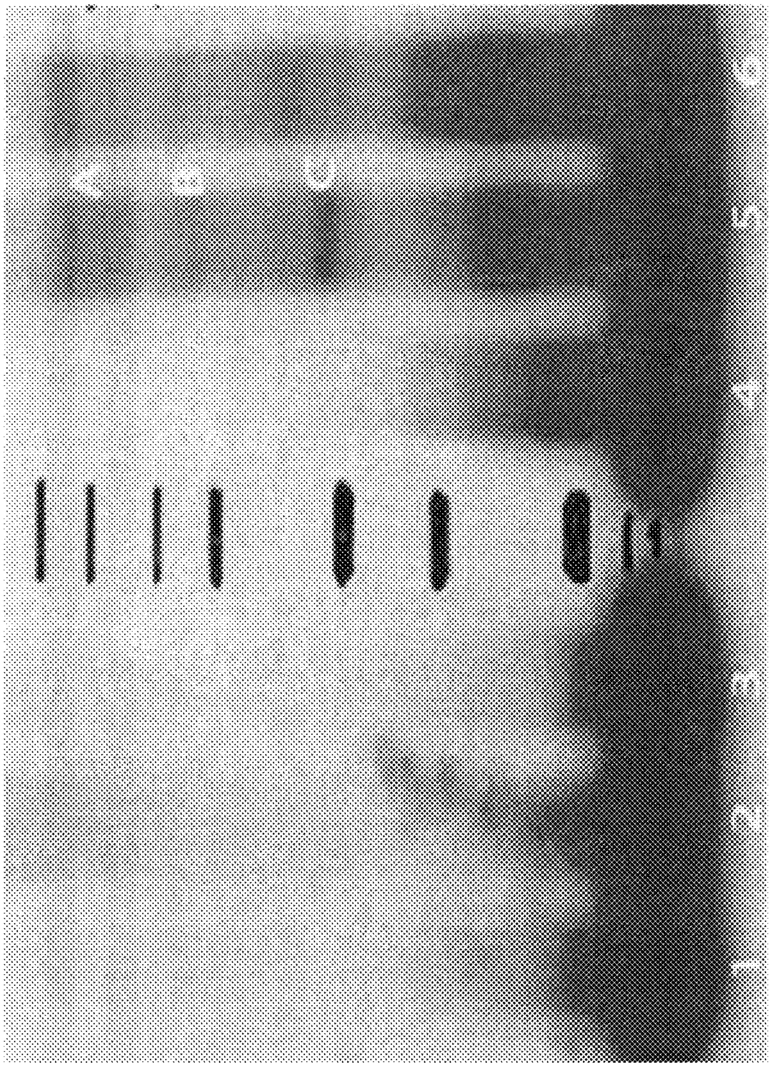

FIG. 21 shows the electrophoretic analysis of nuclear extract proteins cross-linked to NRBS by UV. The radiolabeled Comp-1 was mixed with KAK-1 nuclear extract, cross-linked by UV exposure and resolved on SDS-PAGE. Lane-1: radiolabeled Comp-1 only without UV exposure; Lane-2: radiolabeled Comp-1 only with UV exposure; Lane-3: radiolabeled Comp-1 plus KAK-1 nuclear extract, without UV exposure; Lane-4: radiolabeled Comp-1 plus KAK-1 nuclear extract plus 60× cold Comp-1, without UV exposure; Lane-5: radiolabeled Comp-1 plus KAK-1 nuclear extract, with UV exposure; Lane-6: mixture in Lane-4, with UV exposure. A, B, C mark the three regions that represent the Comp-1-specific probe-protein crosslink products.

FIG. 22, panel A shows the human NIS gene promoter sequence spanning from +1 nucleotide positioned in ATG translation start codon to −725 nucleotide (SEQ ID NO:3); panel B shows NRBS sequence spanning from −645 to −605 nucleotides upstream of the translation start site of human NIS gene (the sequence that is italicized in SEQ ID NO:3 in panel A) (SEQ ID NO:4); panel C shows NRBS sequence spanning from −648 to −620 nucleotides upstream of the translation start site of human NIS gene (the sequence that is boxed in SEQ ID NO:3 in panel A) (SEQ ID NO:5).

DETAILED DESCRIPTION

The present disclosure is based, in part, on the identification of a site in the human sodium-iodide symporter (NIS) promoter region, herein, referred to as NIS-repressor binding site (NRBS). The present disclosure is also based, in part, on the discovery and isolation of an NIS-repressor protein complex which is involved in interacting with NRBS and thereby repressing the transcription of NIS gene. As described herein in detail, one of the components of this complex has been identified as PARP-1.

In one aspect, the present disclosure provides a method of restoring or enhancing the activity of sodium-iodide symporter of a cell in uptaking iodide by contacting the cell with a modulator of the NIS-repressor protein complex binding to NRBS and then administering to the cell radiolabeled iodide.

In one embodiment, the present disclosure provides a method for treating thyroid cancer by restoring or enhancing thyroid cells' ability to uptake radioactive iodide. The method includes administering to a thyroid cancer cell an effective amount of a therapeutic agent capable of antagonizing the formation, activity, or binding of the NIS-repressor protein complex to the NIS-repressor binding site (NRBS) and further administering to the cell a radioactive iodine.

In another embodiment, the present disclosure provides a method for restoring or enhancing thyroid cells' ability to uptake radiolabeled iodide by administering to a thyroid cancer cell an effective amount of a therapeutic agent capable of antagonizing PARP-1 and further administering to the cell a radioactive iodine. In this embodiment, cancer cells are contacted with such agents that are capable of antagonizing PARP-1's association with the NIS-repressor binding site (NRBS). Such agents would be more specific for PARP-1's association with NRBS, such as PJ34, rather than demonstrate a generalized protein inhibition, such as, for example, 3 aminobenzamide or cycloheximide (although these agents can also cause this effect).

In one aspect, the present disclosure provides a method of restoring or enhancing the activity of sodium-iodide symporter of a cell in uptaking iodide by contacting the cell with a modulator of NRBS and then administering to the cell radiolabeled iodide. In one embodiment of this aspect of the disclosure, the modulator of NRBS can be a compound, a nucleic acid sequence, a protein or a peptidomimetic that is capable antagonizing the binding of NIS-repressor protein complex to NRBS.

In order for the present disclosure to be more readily understood, certain terms are defined herein. Additional definitions are set forth throughout the detailed description and in U.S. Pat. Nos. 6,015,376 and 7,029,879 and U.S. patent application Ser. No. 11/652,139, filed Jan. 11, 2007, as incorporated herein in their entirety by reference thereto.

The terms "antagonize" and its cognates, e.g., "reduce", "inhibit", "interfere" as used interchangeably herein refer to the ability of a compound, a composition, or a molecule to act as an antagonist of a certain reaction, activity, binding, or formation. For example, the term "antagonize" may refer to a decrease in the expression, activity, binding, or formation of NIS-repressor protein complex in the presence of a therapeutic compound, relative to the expression, activity, binding, or formation in the absence of the same compound. The decrease in the expression level, activity, binding, or formation is at least about 10%-90% or higher, such as 20%, 30%, 40%, 50%, 60%, 70%, 80%, 90%, 95% or higher. The term "antagonize" may also refer to an inhibition of the formation of a protein-protein or protein-DNA complex, wherein inhibition may mean a decrease in the amount or duration of a complex.

The term "modulate", "modulation", or "modulator" is used herein to refer to the capacity to reduce or inhibit the biological activity, binding, formation or functional property of NIS-repressor protein complex of the disclosure or a component thereof such as PARP-1 that renders the complex or a component thereof ineffective or less effective in binding to and repressing NIS expression.

Radiolabeled iodide ($I^{131}$) is the only known effective systemic therapy of metastatic thyroid cancer since chemotherapeutics are ineffective. $I^{131}$ response depends upon delivery of a sufficiently tumoricidal radiation dose by concentration of $I^{131}$ via the sodium-iodide symporter (NIS), as well as $I^{131}$ retention long enough to irradiate the cells. $I^{131}$ treatment failure is often due to tumor dedifferentiation with loss of iodide uptake and/or retention (Ain K B 2000 *Clin Endocrinol Metab* 14:615-629). Restoring these functions in dedifferentiated thyroid cancer cells should restore effectiveness of radioiodide therapy for these patients.

Based on a tumor $I^{131}$ residence time (effective half-life) of at least 4.5 days, tumor destruction can result from doses of 300 mCi, with a tumor $I^{131}$ uptake of only 0.1%. $I^{131}$ dosimetry studies, to verify safety limits of the administered dose, permitted Benua & Leeper to give single doses up to 600 mCi (Benua et al. 1986 *Plenum Medical Book Co;* 1317-1321) so that tumors with <0.05% (1/20 of normal thyroid) can be treatable. The Applicants have treated patients with aggressive disease with single doses over 800 mCi, without significant morbidity, using dosimetry. Thus, restoration of NIS activity, sufficient to treat thyroid cancer, does not require NIS expression to the levels seen in normal human thyroid follicular cells and can be achieved with lesser degrees of NIS expression. The effective therapeutic amount of any compound or composition of the present disclosure, therefore, can be an amount that promotes the expression of NIS to the levels sufficient for an effective radioiodide therapy.

Based on previous work (see U.S. Pat. Nos. 6,015,376 and 7,029,879 and U.S. patent application Ser. No. 11/652,139, filed Jan. 11, 2007) Applicants had expected the production of an activating protein transcription factor to be diminished by protein synthesis inhibitors (PSI (cycloheximide, anisomycin, emetine)), diminishing luciferase activity of the reporter construct as well as native hNIS mRNA expression. Contrary to these expectations all 3 PSIs stimulated normalized luciferase expression in a dose-dependent, time course-dependent, cell type-specific, and promoter-specific fashion. In addition, PSI increased endogenous hNIS gene transcription in thyroid cancer cells that did not express hNIS under basal or TSH (thyrotropin)-stimulated conditions. Transfections with reporter constructs containing consecutive deletions of hNIS promoter sequences demonstrated the sequence responsible for this PSI-effect to be −725 to −534 bp relative to the translation start site of the hNIS gene (−377 to −186 from transcription initiation site) (Li et al. 2007 *J Clin Endocrinol & Metab* 92(3):1080-1087). These results showed that a trans-active protein factor(s), binding to this portion of hNIS promoter, represses endogenous hNIS transcription in dedifferentiated thyroid cancer cells, accounting for loss of iodine uptake in thyroid cancer metastases. This NIS-repressor can also prove a key component of a common pathway by which diverse agents act to restore hNIS expression. Further studies showed that the NIS-repressor was a protein complex and PARP-1 was a major constituent of this complex.

As described more fully in the Example 5 and throughout the specification, the nucleotide sequence spanning from about −645 to about −605 upstream from the translation start site of human NIS gene (SEQ ID NO:4), the sequence from −648 to −620 upstream from the translation start site of human NIS gene (SEQ ID NO:5), or a nucleic acid sequence having at least 85% sequence identity thereto is the NRBS of the present disclosure.

Accordingly, a DNA construct, such as an expression vector, is also contemplated within the scope of the disclosure. Such a DNA construct comprises a NRBS sequence of the disclosure operably linked to a protein encoding sequence. The promoter includes a nucleotide sequence having a degree of homology upwards of 80%, preferably 85%, more preferably 90%, most preferably 95%, when compared with the NRBS of the disclosure, as described above. A preferred construct includes the nucleotide sequence from about residue −645 to residue −605 (SEQ ID NO:4). A further preferred construct includes the nucleotide sequence from residue −648 to residue −620 (SEQ ID NO:5). Another preferred construct includes the nucleotide sequence having at least 80%, or at least 85%, or at least 90%, or at least 95%, sequence identity with those of SEQ ID NOS: 4 or 5. The protein encoding sequence may be one that encodes the hNIS protein, such as whenever it is desired to increase expression of this protein in a cell, e.g., a carcinoma. Alternatively, the protein encoding sequence may be heterologous to the promoter, i.e., it may be a coding sequence that is not ordinarily under the control of the hNIS promoter (e.g., a reporter gene such as luciferase).

In a further aspect of the disclosure, a cell line is transfected with a DNA construct of the disclosure as described hereinabove. Preferably the cell line is from thyroid. A particularly preferred cell line is KAT-50, which is a thyroid cell line, in order that any thyroid-specific effects required for expression are provided.

As stated earlier, one aspect of the disclosure relates to a method of restoring iodide transport of thyroid carcinoma cells by administering a therapeutic agent that modulates the NIS-repressor protein complex of the disclosure and thus resulting in the restoration of NIS expression to the levels sufficient for an effective radioiodide therapy.

In one embodiment, the therapeutic agent reduces or antagonizes the formation of said NIS-repressor protein complex. The therapeutic agent can further reduce or antagonize the formation of said protein complex by effectively inhibiting the formation of at least one component of the complex at transcription or translation levels. In another embodiment, the therapeutic agent reduces or antagonizes the activity of said repressor protein complex. In yet another embodiment, the therapeutic agent reduces or antagonizes the binding of said protein complex to NRBS or any other factor involved in the transcription of hNIS gene.

Strategies used in inhibiting a protein at the transcription or translation levels include, for example, antisense and antigene strategies. For example, synthetic oligonucleotides can be used to inhibit messenger RNA (mRNA) translation (an antisense strategy), to destroy specific mRNA molecules (a ribozyme strategy), to interfere with function of particular proteins (an aptameric strategy); or to modulate the expression of individual genes by targeting a genome (an antigene strategy); Braasch, et al., "Antisense inhibition of gene expression in cells by oligonucleotides incorporating locked nucleic acids: effect of mRNA target sequence and chimera design," Nucleic Acids Research 2002 30: 5160-5167; Kurreck, et al., "Design of antisense oligonucleotides stabilized by locked nucleic acids," Nucleic Acids Research 2002 30: 1911-1918; Tallet-Lopez, et al., "Antisense oligonucleotides targeted to the domain IIId of the hepatitis C virus IRES compete with 40S ribosomal subunit binding and prevent in vitro translation," Nucleic Acids Research 2003 31: 734-742; Sullivan, et al., "Hammerhead ribozymes designed to cleave all human rod opsin mRNAs which cause autosomal dominant retinitis pigmentosa," Molecular Vision 2002 8: 102-113; Wang, et al., "A general approach for the use of oligonucleotide effectors to regulate the catalysis of RNA-cleaving ribozymes and DNAzymes," Nucleic Acids Research 2002 30:1735-1742; McKay, et al., "Characterization of a potent and specific class of antisense oligonucleotide inhibitor of human Protein Kinase C-α expression," J. Biological Chemistry 1999 274: 1715-1722; Schumacher, et al., "Exposure of human vascular smooth muscle cells to Raf-1 antisense oligodeoxynucleotides: Cellular responses and pharmacodynamic implications," Molecular Pharmacology 1998 53: 97-104; Hicke, et al., "Tenascin-C aptamers are generated using tumor cells and purified protein,". Journal of Biological Chemistry 2001 276:48644-48654; Rhodes, et al., "The generation and characterization of antagonist RNA aptamers to human oncostatin," Journal of Biological Chemistry 2000 275: 28555-28561; Giovannangeli, et al., "Accessibility of nuclear DNA to triplex-forming oligonucleotides: The integrated HIV-1 provirus as a target," Proc Natl Acad Sci USA 1997 94: 79-84; McGuffie, et al., "Anti gene and antiproliferative effects of a c-myc-targeting phosphorothioate triple helix-forming oligonucleotide in human leukemia cells," Cancer Research 2000 60: 3790-3799; Zhou-Sun, et al., "A physico-chemical study of triple helix formation by an oligodeoxythymidylate with N3'->P5' phosphoramidate linkages," Nucleic Acid Research 1997 25: 1782-1787.

Also provided are antibodies that bind to the NIS-repressor protein complex of the disclosure. Suitable antibodies are obtained by immunizing a host animal with peptides comprising all or a portion of the repressor protein. Suitable host animals include rat, sheep, goat, hamster, rabbit, etc. The origin of the protein immunogen may be mouse, rat, monkey etc. The host animal will generally be a different species than the immunogen, e.g. human protein used to immunize rabbit, etc.

The immunogen may comprise the complete repressor protein, or fragments and derivatives thereof. Preferred immunogens comprise all or a part of the subject repressor protein, where these residues contain the post-translation modifications, such as glycosylation, found on the native target protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may include the complete target repressor protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target repressor protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies of the subject disclosure may be produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using MPTS bound to an insoluble support, protein A sepharose, etc.

Monoclonal antibodies can be prepared using a wide variety of methods known in the art including the use of hybridoma, recombinant, phage display and combinatorial antibody library methodologies, or a combination thereof. For example, monoclonal antibodies can be produced using hybridoma techniques including those known in the art and taught, for example, in Harlow and Lane, Antibodies: A Laboratory Manual, Cold Spring Harbor Laboratory Press (1989); Hammerling, et al., in: Monoclonal Antibodies and T-Cell Hybridomas 563-681, Elsevier, N.Y. (1981); Harlow et al., Using Antibodies: A Laboratory Manual, Cold Spring Harbor Laboratory Press (1999), and Antibody Engineering: A Practical Guide, C. A. K. Borrebaeck, Ed., W.H. Freeman and Co., Publishers, New York, pp. 103-120 (1991). Examples of known methods for producing monoclonal antibodies by recombinant, phage display and combinatorial antibody library methods, including libraries derived from immunized and naive animals can be found described in Antibody Engineering: A Practical Guide, C. A. K. Borrebaeck, Ed., supra.

Another aspect of the disclosure relates a method of restoring iodide transport of human thyroid carcinoma cells by using a therapeutic agent that modulates the activity of PARP-1 which is a component of NIS-repressor protein complex capable of repressing the NIS expression.

In one embodiment, prior to administering radioactive iodide to thyroid carcinoma cells, a therapeutic agent capable of antagonizing PARP-1 is contacted to the thyroid cells. The therapeutic agent can antagonize PARP-1 at transcription or translation levels. In another embodiment, the therapeutic agent antagonizes the activity of PARP-1 protein. In yet another embodiment, the therapeutic agent antagonizes the binding of PARP-1 to other factors in the NIS-repressor complex which binds to NRBS of the disclosure and represses the hNIS gene expression. In an embodiment, the PARP-1 inhibitors can be used in the methods of the present disclosure. The PARP-1 inhibitors used in the present disclosure can act via a direct or indirect interaction with PARP-1. The PARP-1 inhibitors used herein can antagonize PARP-1 or can modulate one or more entities in the PARP-1 pathway. The PARP inhibitors can in some embodiments inhibit PARP activity.

PARP (poly-ADP ribose polymerase) participates in a variety of DNA-related functions including gene amplification, cell division, differentiation, apoptosis, DNA base excision repair and also has effects on telomere length and chromosome stability (d'Adda di Fagagna et al, 1999, *Nature Gen.,* 23(1): 76-80). PARP-inhibition has been shown to represent an effective approach to treat a variety of diseases. Various compounds and methods of antagonizing PARPs including PARP-1 are currently known and can be found in, for example, U.S. Patent Applications No. 2008/0076778, titled as "Methods for designing PARP inhibitors and uses thereof"; 2008/0039480, tilted as "Quinazolinedione derivatives as PARP inhibitors"; 2007/0179160, titled as "Use of RNAi inhibiting PARP activity for the manufacture of a medicament for the treatment of cancer"; 2007/0105835, titled as "Compositions and methods for modulating poly (ADP-ribose) polymerase activity; 2006/0204981, titled as "Compositions for modulation of PARP and methods for screening for same.

In some embodiments, the expression of PARP-1 can be inhibited. Inhibition of PARP-1, for example, can be accomplished using any convenient means, including administration of an agent that inhibits PARP-1 (e.g., small molecules or antisense agents), inactivation of PARP-1 gene, e.g., through recombinant techniques, etc.

For example, the anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted repressor protein, and inhibits expression of the targeted repressor protein. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules can be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), Nature Biotechnol. 14:840-844).

A specific region or regions of the endogenous sense strand mRNA sequence of PARP-1 can be chosen to be complemented by the antisense sequence.

Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH 2-5'-O-phosphonate and 3'—NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without compromising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), Nucl. Acids Res. 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), Appl. Biochem. Biotechnol. 54:43-56.

In other embodiments, in accordance with an aspect of the present disclosure, one or more compounds, nucleic acid sequences, proteins or peptidomimetics can be used to antagonize NRBS and its binding to the NIS-repressor protein complex. In one embodiment an NRBS antagonist is administered first and a radiolabeled iodide is administered next.

One method of antagonizing NRBS is to employ double-stranded, i.e., duplex, oligonucleotide decoys for NRBS, which binds to the NIS-repressor protein complex and thereby prevent the repressor complex from binding to its target NRBS of the disclosure. These duplex oligonucleotide decoys have at least that portion of the sequence of NRBS required to bind to NIS-repressor protein complex and thereby prevent its binding to NRBS of the disclosure. In some embodiments, the subject decoy nucleic acid molecules include a sequence of nucleotides that is the same as a sequence found in the DNA molecule spanning from −645 to −605 nucleotides (SEQ ID NO:4) or from −648 to −620 nucleotide (SEQ ID NO:5) upstream from the translation start site of human NIS gene. In other embodiments, the subject decoy nucleic acid molecules include a sequence of nucleotides that is substantially the same as or identical to a sequence found in the DNA molecule of SEQ ID NO:4 or SEQ ID NO:5; where the terms substantially the same as and identical thereto in relation to nucleic acids are defined below. In using such oligonucleotide decoys, the decoys are placed into the environment of NRBS and the NIS-repressor protein complex, resulting in de-repression of the transcription and expression of the NIS coding sequence. Oligonucleotide decoys and methods for their use and administration are further described in general terms in Morishita et al., Circ Res (1998) 82 (10):1023-8. These oligonucleotide decoys generally include an NRBS recognized by the NIS-repressor protein complex, including the specific regions detailed above, where these particular embodiments include nucleic acid compositions of the subject disclosure, as described in greater detail below.

By 'substantially the same as' is meant a protein having a sequence that has at least about 50%, usually at least about 60% and more usually at least about 75%, and in many embodiments at least about 80%, usually at least about 90% and more usually at least about 95%, 96%, 97%, 98% or 99% sequence identity with the sequence of NRBS of the disclosure, as measured by the BLAST program to compare two sequences (available on the NCBI website using default settings). Such DNA sequence will be capable of binding to NIS-repressor protein complex. To determine whether an NRBS sequence substantially the same as the refined NRBS (R-NRBS) of the disclosure still binds to the NIS-repressor protein complex, in vitro titrations can be done using EMSA methods described in the Examples. For example, a skilled artisan familiar with molecular biology can systematically change the nucleotides of R-NRBS of the disclosure and determine if the sequence still binds to the NIS-repressor binding complex of the disclosure.

The interaction between NRBS of the present disclosure and the NIS-repressor protein complex can further be antagonized by using antibodies or peptidomimetics that are capable of binding to NRBS and inhibit or reduce the effective binding of the repressor complex to this site. Such antibodies can be prepared by the methods known and described in the art in the references cited above.

In some embodiments, a synthetic peptide, polypeptide or peptiodomimetic capable of binding to NRBS of the present disclosure can be used as a blocking agent affecting the interaction of NRBS with the NIS repressor protein complex.

Methods for synthesizing peptides, polypeptides, peptidomimetics and proteins are well known in the art (see, for example, U.S. Pat. Nos. 5,420,109; 5,849,690; 5,686,567; 5,990,273; in PCT publication WO 01/00656, and in M. Bodanzsky, Principles of Peptide Synthesis (1st ed. & 2d rev. ed.), Springer Verlag, New York, N.Y. (1984 & 1993), see Chapter 7; Stewart and Young, Solid Phase Peptide Synthesis, (2d ed.), Pierce Chemical Co., Rockford, Ill. (1984).

Another aspect of the disclosure relates to a method of identifying a candidate molecule that is capable of modulating the formation, activity, or binding of PARP-1 or the NIS-repressor protein complex in thyroid carcinoma, comprising contacting the candidate molecule with a test cell, where the test cell contains an expression vector having an NIS-repressor oligonucleotide-binding site (NRBS) operably linked to a reporter gene; and identifying the molecule as an agent capable of modulating PARP-1 or the NIS-repressor protein complex when the amount of the reporter product produced by the test cell is greater than an amount of reporter product produced by the test cell grown in the absence of the candidate molecule. In one embodiment, the test cell does not express hNIS (due to production or presence of PARP-1 and/or the hNIS-repressor protein complex). In another embodiment the test cell is selected from cell lines such as, for example, KAK-1 and NPA'87. In yet another embodiment, the reporter gene includes, for example, hNIS.

Another aspect of the disclosure relates to method of screening for therapeutic agents useful in restoring the expression of hNIS gene and the uptake of radioiodine in a thyroid cancer cell, comprising the steps of contacting the test cell with a therapeutic agent capable of antagonizing the formation, activity, or binding of PARP-1 or the NIS-repressor protein complex with NRBS and detecting the hNIS gene or protein expression and/or radioiodine uptake by that cell. In one embodiment, the test cell does not express hNIS (due to production or presence of PARP-1 and/or the hNIS-repressor protein complex). In another embodiment the test cell is selected from cell lines such as, for example, KAK-1 and NPA'87.

The agent screening methods include methods of detecting an agent that antagonizes the NIS-repressor protein complex or a component thereof and thereby result in an increased level of a NIS mRNA and/or NIS polypeptide in a cell. In some embodiments, the methods involve contacting a cell that produces NIS-repressor protein complex with a test agent, and determining the effect, if any, of the test agent on the level of NIS mRNA in the cell.

A wide variety of cell-based assays may be used for identifying agents which antagonize the NIS-repressor protein complex and increase a level of NIS mRNA in a eukaryotic cell, using, for example, KAK-1 and NPA'87.

Accordingly, the present invention provides a method for identifying an agent, particularly a biologically active agent, that increases the level of NIS expression in a cell, the method comprising: combining a candidate agent to be tested with a cell containing a nucleic acid which encodes a NIS-repressor protein complex, and/or a construct comprising the NRBS of the present disclosure operably linked to NIS or a reporter gene; and determining the effect of said agent on NIS or the reporter gene expression. For example, an increase of at least about 5%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, in the level (i.e., an amount) of NIS mRNA and/or polypeptide following contacting the cell with a candidate agent being tested, compared to a control to which no agent is added, is an indication that the agent modulates NIS expression.

Cell-based assays generally comprise the steps of contacting the cell with an agent to be tested, forming a test sample, and, after a suitable time, assessing the effect of the agent on NIS (or reporter gene) expression. A control sample comprises the same cell without the candidate agent added. NIS or reporter gene expression levels are measured in both the test sample and the control sample. A comparison is made between NIS or reporter gene expression level in the test sample and the control sample; the expression can be assessed using conventional assays. A suitable period of time for contacting the agent with the cell can be determined empirically, and is generally a time sufficient to allow entry of the agent into the cell and to allow the agent to have a measurable effect on NIS mRNA and/or polypeptide levels. Generally, a suitable time is between 10 minutes and 24 hours, or from about 1 hour to about 8 hours.

Methods of measuring NIS mRNA levels are known in the art and also shown in the Examples. Any of these methods can be used in the methods of the present disclosure to identify an agent which modulates the association between NRBS and NIS-repressor protein complex, and thereby result in a change in the mRNA levels. For example, a polymerase chain reaction (PCR), such as a PCR employing detectably labeled oligonucleotide primers, and any of a variety of hybridization assays can be used for measuring NIS or reporter gene mRNA levels.

Similarly, NIS polypeptide levels can be measured using any standard method, several of which have been described herein, including, but not limited to, an immunoassay such as enzyme-linked immunosorbent assay (ELISA), for example an ELISA employing a detectably labeled antibody specific for a NIS polypeptide.

Fluorescent proteins suitable for use include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) J. Protein Chem. 20:507-519; "humanized" recombinant GFP (hrGFP) (Stratagene); any of a variety of fluorescent and colored proteins from Anthozoan species, as described in, e.g., Matz et al. (1999) Nature Biotechnol. 17:969-973; and the like. Where the fusion partner is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

Another aspect of the disclosure relates to a method for identifying additional components and/or binding partners of NIS-repressor protein complex, comprising contacting an NRBS probe with nuclear extracts from thyroid cancer cells, allowing the repressor protein complex to form, and detecting the additional binding partner. In one embodiment, the detection step can be carried out by, for example, mass spectroscopy or immunohistochemistry. In another embodiment, cell-based assays, such as the ones disclosed in the following Examples, can be used for detection and isolation of NRBS binding partners.

Another aspect of the disclosure relates to a method for diagnosing or screening a patient for the presence of or a predisposition for a thyroid cancer cell to lose the ability to concentrate radioactive iodine characterized by an aberrant level of PARP-1 protein comprising measuring the level of PARP-1 mRNA, protein, or functional activity in a thyroid cell sample derived from the subject, in which an increase or decrease in any of those levels is measured relative to an analogous sample not having an impairment of iodine concentrating ability.

In another aspect, a kit is provided containing, for example, mRNA primers, antibodies, or tagged NAD for detecting PARP-1's mRNA, protein, or activity levels, respectively. In another embodiment, the kit includes standardized control reagents obtained from a sample not having an impairment of iodine concentrating ability.

This disclosure also provides therapeutic kits comprising therapeutic agents for use in the present treatment methods. Such kits will generally contain, in suitable container means, a pharmaceutically acceptable formulation of at least one therapeutic agent which is capable of antagonizing the association of the NIS repressor protein complex and the NRBS of the present disclosure, and a radioactive iodide. The kit can also contain other pharmaceutically acceptable formulations, either for diagnosis or combined therapy. For example, such kits may contain any one or more of a range of chemotherapeutic or radiotherapeutic drugs; anti-angiogenic agents; anti-tumor cell antibodies; and/or anti-tumor vasculature or anti-tumor stroma immunotoxins or coaguligands.

The kits may have a single container (container means) that contains the therapeutic agent which is capable of antagonizing the association of the NIS repressor protein complex and the NRBS of the present disclosure, with or without any additional components, or they may have distinct containers for each desired agent. In one embodiment, the therapeutic agent capable of antagonizing the association of the NIS repressor protein complex with the NRBS of the present disclosure, and other anti-cancer agents such as a radioactive iodide are maintained separately within distinct containers prior to administration to a patient.

The containers of the kit will generally include at least one vial, test tube, flask, bottle, syringe or other container means, into which the therapeutic agent and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluents.

The kits may also contain instructions and means by which to administer the therapeutic agent to a subject, e.g., one or more needles or syringes, or even an eye dropper, pipette, or other such like apparatus, from which the formulation may be injected into the subject or applied to a diseased area of the body. The kits of the present disclosure will also typically include a means for containing the vials, or such like, and other component, in close confinement for commercial sale, such as, e.g., injection or blow-molded plastic containers into which the desired vials and other apparatus are placed and retained.

Additional objects and advantages of the disclosure will be set forth in part in the description which follows, and in part will be obvious from the description, or may be learned by practice of the disclosure.

EXAMPLES

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and H (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.).

The following describes materials and methods used in the procedures described in the subsequent Examples.

Cell Lines

The human thyroid cell line NPA'87 (derived from a papillary thyroid carcinoma) and DRO (derived from anaplastic thyroid carcinoma) was provided by G. J. F. Juillard, University of California-Los Angeles School of Medicine). KAK-1 was obtained from a histologically benign follicular adenoma; Ain et al., 1994 J Clin Endocrinol Metab 78:1097-102. Primary cultures were previously treated with medium containing D-valine; Gilbert et al., 1975 Cell 5:11-7; and cis-4-hydroxy-1-proline; Kao et al., 1977 *Nature* 266:634; to ensure the absence of fibroblasts.

Cell Culture Conditions

The basal media and supplements were all from GIBCO/Invitrogen Corporation, Grand Island, N.Y. All thyroid cell lines were grown in phenol red-free RPMI 1640 (GIBCO) with 10% FBS, 100 nmol/L sodium selenite, and 0.1 nmol/L bovine TSH (Sigma) at 37° C. in 5% $CO_2$. KAK-1 cells were also cultured in high-glucose, phenol red-free RPMI 1640 supplemented with 10% FBS, 100 nM sodium selenite, 5 pIU/ml human TSH, 0.1 mM non-essential amino acids, 1 mM sodium pyruvate at 37° C. in 5% CO2. Cell culture media was replenished every 2 days. All chemical reagents were obtained from Sigma Chemical Company (St. Louis, Mo.). In addition, PJ34 was obtained from CalBiochem/EMD Biosciences, Inc. (La Jolla, Calif.) and used at 30 μmole/liter. Cycloheximide (CHX), 3-aminobenzamide (3-AB), 5-azacytidine (azaC), and sodium butyrate (NaB) were from Sigma-Aldrich Chemical Company (St. Louis, Mo.) and used at 10 μg/ml, 7.5 mM, 0.5 μM, 1 mM respectively.

Total RNA Isolation and Quantitative RT-PCR (qRT-PCR)

Total RNA was isolated using TRIzol reagent (Invitrogen Corp., Carlsbad, Calif.), genomic DNA contamination removed using DNA-free kit (Ambion Inc., Austin, Tex.), and cDNA synthesized from 2 μg total RNA using Advantage RT-for-PCR kit (BD Biosciences Clontech, Palo Alto, Calif.) with random hexamer primers. TaqMan Universal PCR Master Mix (Applied Biosystems, Foster City, Calif.) and Assay-on-Demand Gene Expression Products (Hs00166567_m1 for hNIS mRNA and Hs999999-1_s1 for 18sRNA, respectively; Applied Biosystems) were used for RNA quantitation. The hNIS fragment (1446-1865, +1 is translation initiation codon "A") was PCR amplified using NIS-F (5'-ctgcgtggctctct-cagtc-3' SEQ ID NO:6) and NIS-R (5'-ccctccagctccttctgc-3' SEQ ID NO:7), followed by ligation into pCR2.1 vector (Invitrogen). The same procedure was followed using 18s-F (5'-atggtgaccacgggtgacg-3' SEQ ID NO:8) and 18s-R (5'-ttattcctagctgcggtatcc-3' SEQ ID NO:9) for 18s qPCR standard. DNA preparations of these two plasmids were quantitated, diluted and used as quantitation standards in qPCR measurements.

Chromatin Immunoprecipitation Assay (ChIP)

Chromatin immunoprecipitation assay (ChIP) was performed using ChIP-IT™ kit from Active Motif® (Carlsbad, Calif.) with KAK-1 cells cultured under basal conditions. Cells were fixed with formaldehyde, chromatin DNA was isolated and sheared using the enzymatic shearing cocktail in the kit. The human PARP-1/chromatin DNA complex were immunoprecipitated using anti-human PARP-1 polyclonal antibodies from Roche® (Indianapolis, Ind.) and R&D System® (Minneapolis, Minn.) respectively, followed by addition of Protein G beads. Chromatin DNA were eluted from the beads and heated to reserve cross-links between protein and DNA and then purified using mini-columns. Interaction between PARP-1 and NRBS probe was interrogated with PCR using NRBS-F and NRBS-R primer pair, which covers from −708 to −551 bp relative to the translation start site of human NIS gene. The PCR parameters were: 95° C.×15 min to activate the HotStarTaq™ DNA polymerase from Qiagen® (Valencia, Calif.) followed by 40 cycles of 94° C.×30 sec, 57° C.×25 sec, 72° C.×30 sec.

Vector Constructions 1) hNIS promoter luciferase reporter constructs containing site-directed mutations in hNIS promoter.

A series of site-directed mutation primers, Muta-Fx and Muta-Rx (x=1 to 17, and 19 to 23) were synthesized together with primer F-4.5 (5'-gaggtaccggagcaaagtcttccccaag-3' SEQ ID NO:10, from −953 to −934 relative to the "A" in hNIS translation initiation codon. KpnI site is underlined) and Luc-R1 (5'-agaagcftggaggtcgccttggggcttac-3' SEQ ID NO:11, from −1 to −22, Hind3 site is underlined). The sequences of all the mutation oligos are listed in the Table 1.

TABLE 1

Primers used to make site-directed mutations in hNIS promoter

| X= | Muta-Fx (5' to 3') | Muta-Rx (5' to 3') |
|---|---|---|
| 1 | aaaaaggtattcaagcacaatac SEQ ID NO:12 | ttttggggagctcactttcatgc SEQ ID NO:13 |
| 2 | aaaagcacaatacggctttgagt SEQ ID NO:14 | tttccttgagctatggggagctc SEQ ID NO:15 |
| 3 | aaattgagtgctgaagcaggctg SEQ ID NO:16 | tttattgtgcttgaataccttga SEQ ID NO:17 |
| 4 | aaaaagcaggctgtgcaggcttg SEQ ID NO:18 | ttttcaaagccgtattgtgcttg SEQ ID NO:19 |
| 5 | aaatgcaggcttggatagtgaca SEQ ID NO:20 | tttgcttcagcactcaaagccgt SEQ ID NO:21 |
| 6 | aaagatagtgacatgcccttttttg SEQ ID NO:22 | ttttgcacagcctgcttcagcac SEQ ID NO:23 |
| 7 | aaatgccctttttgagcctcaattt SEQ ID NO:24 | ttttatccaagcctgcacagcct SEQ ID NO:25 |
| 8 | aaatttgagcctcaatttcccca SEQ ID NO:26 | tttatgtcactatccaagcctgc SEQ ID NO:27 |
| 9 | aaacaatttccccacctgtcaac SEQ ID NO:28 | tttaaaaagggcatgtcactatcc SEQ ID NO:29 |
| 10 | aaactgtcaacagcagacagtga SEQ ID NO:30 | tttaaattgaggctcaaaaaggg SEQ ID NO:31 |
| 11 | aaaacagcagacagtgacagctgt SEQ ID NO:32 | tttgtggggaaattgaggctcaa SEQ ID NO:33 |
| 12 | aaaacagtgacagctgtgatcag SEQ ID NO:34 | ttttgacaggtggggaaattga SEQ ID NO:35 |
| 13 | aaagctgtgatcaggggatcaca SEQ ID NO:36 | ttttgtctgctgttgacaggtgg SEQ ID NO:37 |
| 14 | aaaatcaggggatcacagtgcat SEQ ID NO:38 | ttttgtcactgtctgctgttgac SEQ ID NO:39 |
| 15 | aaaatcacagtgcatggggatgg SEQ ID NO:40 | tttatcacagctgtcactgtctg SEQ ID NO:41 |
| 16 | aaagcatggggatgggtgtgtgc SEQ ID NO:42 | tttatcccctgatcacagctgtc SEQ ID NO:43 |
| 17 | aaaggatgggtgtgtgcatgg SEQ ID NO:44 | tttactgtgatcccctgatcaca SEQ ID NO:45 |
| 19 | aaagcatggggatggaggggca SEQ ID NO:46 | tttccatccccatgcactgtgat SEQ ID NO:47 |
| 20 | aaaggatggaggggcatttgg SEQ ID NO:48 | tttacacacccatccccatgcac SEQ ID NO:49 |
| 21 | aaaaggggcatttgggagcc SEQ ID NO:50 | tttccatgcacacacccatccc SEQ ID NO:51 |
| 22 | aaaatttgggagccctccccga SEQ ID NO:52 | tttccatccccatgcacacacc SEQ ID NO:53 |
| 23 | aaacctccccgataccacccccct SEQ ID NO:54 | tttaaatgcccctccatccccat SEQ ID NO:55 |

Briefly, after treatment with T4 polynucleotide kinase to phosphorylate the 5' end of all the Muta-F and Muta-R primers, taking the F1-pGL3-Basic plasmid template, F-4.5 and Muta-Rx was used as primer pairs to amplify 22 different 5' regions all starting from the F4.5, while Luc-R1 and Muta-Fx was used as primer pairs to amplify 22 different 3' regions all ending at Luc-R1. All the PCR fragments were gel-purified, followed by 22 ligation reactions to link the F4.5/Muta-Rx fragment with the Luc-R1/Muta-Fx fragment for each site separately using T4 DNA ligase. Then, 22 different promoter mutation fragments all starting from the primer F-4.5 and ending at Luc-R1 were PCR amplified using these 22 ligation products as templates and using the primer F4.5 and R1 as the primer pair. Finally, these 22 PCR fragments were gel-purified and double digested with HindIII and KpnI, followed by separate ligation into pGL3-basic vector from Promega (Madison, Wis.) that had been double digested with these same enzymes to make 22 constructs each containing a single site-directed mutation (F4.5/Muta-x-pGL3-basic). Also, a construct containing the PCR fragment amplified from the F1-pGL3-basic plasmid using F-4.5 and R1 as primer pair was produced as the control plasmid (F4.5-pGL3-basic). All the oligo primers were synthesized by Integrated DNA Technologies, Inc. (Coralville, Iowa).

The DNA sequence covering −724 to −534 bp of hNIS is shown in FIG. 6 with the numbers above the sequence indicating the mutations and the square brackets enclosing the original sequences, together with the sequences in lower case below each square bracket showing the mutated sequence.

2) Expression plasmid for human PARP-1 DNA-binding-domain.

The DNA sequence encoding two tandem influenza hemaglutinin (HA) tag was synthesized by ligation of two annealed double strand synthetic oligos listed as follow. HA-1: 5'-gatcctatccctatgatgtgcccgactatgcttccggtac-3' (SEQ ID NO:56)/5'-cggaagcatagtcgggcacatcatagggatag-3' (SEQ ID NO:57). HA-2: 5'-ctacccttacgacg ttcctgactacgccagcctctaat-3' (SEQ ID NO:58)/5'-ctagattagaggctggcgtagtcaggaacgtcgtaagggtaggt-3' (SEQ ID NO:59). The annealed tandem HA tag sequence was inserted into pCR3.1 vector (Invitrogen) at BamHI/XbaI sites to form pCR3.1-HA2 plasmid. The DNA-binding domain (DBD) of human PARP-1 containing amino acids 1-372 was PCR amplified using human PARP-1/pCMV6-XL5 plasmid from OriGene (Rockville, Md., Cat# sc119157) as template, with PARP-1F (5' ag gctaqcgccaccatggcggagtcttcggataagctc-3' SEQ ID NO:60, NheI site and Kozak sequence are underlined) and PARP-1R (5'-acggatccggagggcggaggcgtggccg-3' SEQ ID NO:61, BamHI site is underlined) as PCR primer pair. The PCR product was gel-purified and digested with NheI/BamHI, followed by ligation into pCR3.1-HA2 plasmid that had been cut with the same enzymes to obtain the DBD-HA2/pCR3.1 plasmid.

3) Expression plasmids for the fusion proteins consisting of yeast GAL4 DNA-binding domain (DBD) and wild type or mutant (C908R) human PARP-1 enzymatic domain.

a. Expression plasmid for the fusion protein of yeast GAL4 DBD and wild type human PARP-1 enzymatic domain (amino acids 233-1014).

The C-terminal portion of hPARP-1 was PCR amplified using human PARP-1/pCMV6-XL5 clone from OriGene as template with EcoRV-F (5'-tgcgtatgacttggaagtcatc-3' SEQ ID NO:62) and PARP-end (5' gc ctcgagttaccacagggaggtcttaaaattg-3' SEQ ID NO:63, XhoI site is underlined) as primer pair. An XhoI site was introduced immediately downstream of the stop codon of hPARP-1 coding region in this PCR step. The PCR product was gel-purified, digested with EcoRV/XhoI, and ligated into pCR2.1 plasmid at Hind3/XhoI sites together with a 1.8 kb DNA fragment released from the PARP-1/pCMV6-XL5 plasmid by Hind3/EcoRV digestion to get the pCR2.1 plasmid containing hPARP-1 enzymatic domain from amino acids 233 to 1014. Later the full PARP-1 enzymatic domain (aa233-1014) was recovered with Hind3/XbaI digestion, followed by ligation into pCMV-BD vector from Stratagene (La Jolla, Calif.) that had been digested with BamHI/XbaI in the presence of the BamHI/Hind3 adaptor prepared by annealing Adaptor-F (5'-gatcctcggacaaggatagta-3', SEQ ID NO:64) and Adaptor-R (5'-agcttactatccttgtccgag-3', SEQ ID NO:65) to obtain pBD-PARP-En(+).

b. Expression plasmid for the fusion protein of yeast GAL4 DBD and mutant (C908R) human PARP-1 enzymatic domain.

The C908R mutation was introduced by PCR as follows. First, two mutation fragments were PCR amplified using the PARP-1/pCMV6-XL5 plasmid as template with EcoRV-F/908R (5'-tccctgagacgtatggcggtagttggcactcttgg-3' SEQ ID NO:66, the mutation is underlined) and 908F (5'-ccaagagtgccaactaccgccatacgtctcaggga-3' SEQ ID NO:67, the mutation is underlined)/PARP-end as primer pairs separately, followed by gel-purification. Then, these two PCR fragments were linked together by PCR using the mixture of these 2 mutation fragments as template and EcoRV-F/PARP-end as PCR primer pair to obtain mutant (C908R) EcoRV-F/PARP-end fragment. The following procedures were the same as those in the construction of pBD-PARP-En(+) to obtain pBD-PARP-En(−).

c. Luciferase reporter plasmid containing hNIS promoter region with deletion of −667 to −588 base pair.

The 5'-fragment and 3'-fragment were PCR amplified using F1-pGL3-basic as template, with Luc-F4/-668R (5'-gt ggtacctgatagggacaagccagactc-3' SEQ ID NO:68/5'-ag ggatccgcctgcacagcctgcttcag-3' SEQ ID NO:69, KpnI, BamHI sites are underlined) and −587F (5'-ag ggatcctcgagacagtgcatggggatgggt-3' SEQ ID NO:70, BamHI site is underlined and XhoI site is italic.)/Luc-R1 as primer pairs separately. These two fragments were gel-purified, digested with KpnI/BamHI and BamHI/Hind3 respectively, followed by ligation together into pGL3-basic that had been digested with KpnI/Hind3 to get the luciferase reporter plasmid F4Δ-pGL3-basic, which contains hNIS promoter region from −1252 to −348 bp inserted upstream of luciferase coding sequence, but with the region from −667 to −588 bp deleted.

d. Luciferase reporter plasmid containing hNIS promoter region with the sequence from −667 to −588 base pair replaced with 5×GAL4 binding element.

The 5×GAL4 binding element was PCR amplified using pFR-Luc vector from Stratagene with GAL-F (5'-ag ggatccttgcatgcctgcaggtc-3' SEQ ID NO:71, BamHI site is underlined)/GAL-R (5'-agctcgagccctctagagtctccgct-3' SEQ ID NO:72, XhoI site is underlined) as primer pair. The PCR product was gel-purified and digested with BamHI/XhoI. The Luc-F4/-668R1 and −587F/Luc-R1 PCR products mentioned above in c. were digested with KpnI/BamHI and XhoI/Hind3 respectively. These 3 digested PCR fragments were ligated together with pGL3-basic vector that had been digested with KpnI/Hind3 to get the luciferase reporter plasmid F4ΔGAL-pGL3-basic, which contains hNIS promoter region from −1252 to −348 bp inserted upstream of luciferase coding sequence, but with the sequence from −667 to −588 bp replaced with 5×GAL binding element.

Transient Transfection Assay with Luciferase Reporter Constructs

For the transient transfection assays to test the luciferase activities from the mutant hNIS promoter reporter constructs in response to CHX treatment, CHX was added at 10 μg/mL 1 hr before transfection. Luciferase reporter plasmids/pUC18/phRG-B (Promega) were transfected into KAK-1 cells using Lipofectamine 2000 from Invitrogen. Twenty four hours later, transfection mixtures were replaced with fresh media containing CHX. Luciferase and Rennilar luciferase activities were determined 24 hr later with the Dual-luciferase Assay Kit from Promega.

For the transient transfection assays to monitor the effects of PJ34, PJ34 was administered at 30 μM one hour before DNA transfection mixtures were added to the KAK-1 cultures. Twenty-four hours later, transfection mixtures were replaced with fresh media containing PJ34. Luciferase and Rennilar activities were determined 24 hr later. Luciferase activity was normalized to Rennilar activity to account for the variations in transfection efficiency. Triplicate transfections were performed and data were presented as mean±SD.

Electrophoretic Mobility Shift Assay (EMSA)

Nuclear extracts were prepared using the NucBuster Protein Extraction kit from Novagen/EMD Biosciences, Inc. (La Jolla, Calif.) following its instructions. The radioactive EMSA probes were end-labeled using T4 polynucleotide kinase in the presence of γ-$P^{32}$-ATP (GE Healthcare Bio-Sciences Corp., Piscataway, N.J.), followed by removal of the free radioactive ATP with the QIAquick Nucleotide Removal Kit from Qiagen (Valencia, Calif.). EMSA reaction was performed using the EMSA Accessory Kit (Novagen) following its instructions. Briefly, 1 µL 10 mM DTT, 5 µL 4×EMSA buffer, 1 µL Salmon sperm DNA and 1 µL poly dI:dC were mixed with 3 µL nuclear extracts, 1 µL radioactive EMSA probe and water to make up to 18 µL. In some reactions, antibodies or cold competitive probes were added. The mixtures were incubated on ice for 30 min, Then 2 µL loading dye were added to each reaction tubes, and the samples were loaded onto 7.5% PAGE/0.5×TBE, and run overnight. The gel was dried, exposed to X-ray films that were developed 2-3 days later. The competitive EMSA probes were prepared by annealing the sense and anti-sense single strand synthetic oligos respectively, which are listed in Table 2.

TABLE 2

Oligonucleotides used to make double-stranded competitive probes for EMSA assay

| Probes | Sense strand sequence Sequence (5' to 3') | Anti-sense strand sequence Sequence (5' to 3') |
|---|---|---|
| Comp-0.9 -660 to -627 | gtgacatgcccttttgagcctcaatttccccac Seq ID No:73 | gtggggaaattgaggctcaaaaagggcatgtcac Seq ID No:74 |
| Comp-1 -653 to -615 | gcccttttgagcctcaatttccccacctgtcaacagca Seq ID No:75 | tgctgttgacaggtggggaaattgaggctcaaaaagggc Seq ID No:76 |
| Comp-1.1 -653 to -630 | gcccttttgagcctcaatttccc Seq ID No:77 | gggaaattgaggctcaaaaagggc Seq ID No:78 |
| Comp-1.2 -648 to -625 | ttttgagcctcaatttccccacct Seq ID No:79 | aggtggggaaattgaggctcaaaa Seq ID No:80 |
| Comp-1.3 -643 to -620 | agcctcaatttccccacctgtcaa Seq ID No:81 | ttgacaggtggggaaattgaggct Seq ID No:82 |
| Comp-1.4 -638 to -615 | caatttccccacctgtcaacagca Seq ID No:83 | tgctgttgacaggtgggggaaattg Seq ID No:84 |
| Comp-2 -633 to -595 | tccccacctgtcaacagcagacagtgacagctgtgatca Seq ID No:85 | tgatcacagctgtcactgtctgctgttgacaggtgggga Seq ID No:86 |
| AP-1 (c-jun) | cgcttgatgagtcagccggaa Seq ID No:87 | ttccggctgactcatcaagcg Seq ID No:88 |
| AP-2 | gatcgaactgaccgcccgcggcccgt Seq ID No:89 | acgggccgcgggcggtcagttcgatc Seq ID No:90 |
| CREB | agagattgcctgacgtcagagagctag Seq ID No:91 | ctagctctctgacgtcaggcaatctct Seq ID No:92 |
| Sp-1 | attcgatcggggcggggcgagc Seq ID No:93 | gctcgccccgccccgatcgaat Seq ID No:94 |
| TTF-1/Pax-8 | cactgcccagtcaagtggttcttga Seq ID No:95 | tcaagaaccacttgactgggcagtg Seq ID No:96 |
| TTF-2 | gagggagttcctgtgactagcagagaaaacaaagtgagccac Seq ID No:97 | gtggctcactttgttttctctgctagtcacaggaactccctc Seq ID No:98 |
| Pax-8 | cagctgctctatgaagtgtgaagaa Seq ID No:99 | ttcttcacacttcatagagcagctg Seq ID No:100 |

The EMSA probe A (126 bp, −684 to −565 bp) was prepared by PCR amplification with the forward primer Muta-F4 (5'-aaaaagcaggctgtgcaggcttg-3'. SEQ ID NO:101) and the reverse primer Muta-R20 (5'-tttacacacccatccccatgcac-3' SEQ ID NO:102). The EMSA probe B (196 bp, −533 to −348 bp) was PCR amplified with the forward primer F6.1 (5'-ga ggtaccccgataccacccctgca-3' SEQ ID NO:103, KpnI site is underlined) and reverse primer LucRl (5'-ag aagcttggaggtcgccttggggcttac-3' SEQ ID NO:104, Hind3 site is underlined). The plasmid F1-pGL3-basic was used as the PCR template in these two PCR amplifications.

LC/MS/MS Analysis

The biotinylated affinity probe was made by PCR using F1-pGL3-basic plasmid as template with wtF4 (5'-ttgagtgctgaagcaggctgtgc-3' SEQ ID NO:105)/Biotin-R22 (5'-BioTEG/tgcccctccatccccatgcac-3' SEQ ID NO:106) as primer pair. The control probe was made similarly, but with wtF20 (5'-catggggatggaggggcatt-3' SEQ ID NO:107)/Luc-R1 as primer pair. These two probes were gel-purified and quantitated. Dynabeads M-280 streptavidin from Invitrogen were washed 3 times with 2M NaCl, 1 mM EDTA, 10 mM Tris-HCl (pH7.5), followed by washing twice with 1×EMSA buffer (100 mM KCl, 20 mM HEPES pH8.0, 0.2 mM EDTA, 20% Glycerol). Then the beads were incubated with bovine insulin solution (5 mg/ml in 1×EMSA buffer) at room temperature for 15 min on a rolling wheel to block non-specific binding to the beads. Later, the beads were washed twice again with 1×EMSA buffer and resuspended in 1×EMSA buffer. 500 μL of nuclear extract (8 μg/μL) from KAK-1 cells cultured under basal conditions was mixed with 220 μL 1×EMSA buffer, 40 μL salmon testes DNA (500 ng/μL, Sigma), 40 μL poly dI:dC (0.01 U/μL, Sigma), 40 μL DTT (10 mM), 8 pmole biotinylated affinity probe and 32 pmole control probe. The mixture was incubated at 4° C. for 30 min on a rolling wheel, followed by addition of 100 μL pre-blocked M-280 beads, and further incubated at 4° C. for 1 hr. The beads were collected by magnet force and washed 5 times with 500 μL 1×EMSA buffer supplemented with 0.5 mM DTT (final concentration). Each washing step lasted for 3 min at 4° C. on a rolling wheel. The M-280 beads were collected, washed once with 500 μL cold HBSS, resuspended in cold HBSS and sent for LC/MS/MS analysis.

The beads were collected and eluted with NH4HCO3 at increasing concentrations. The eluate was acidified with formic acid, evaporated to dryness and then digested with trypsin. Digests were acidified, dried, and reconstituted with 10 μL of 5% acetonitrile. Five microliters of sample was injected in a C18 capillary column, eluted with an acetonitrile-H2O gradient. Electron spray ionization followed by tandem mass spectrometry (LC/MS/MS) was performed on a Finnigan LTQ with the resulting MS-MS spectra analyzed using the Mascot (Matrix Science) protein database search engine against mammalian proteins in the SwissProt database.

UV-Crosslinking Experiment

The EMSA assay was set up as described above, followed by UV-crosslink on ice using HB-2000 Hybridizer from UVP Inc. (Upland, Calif.) at 400 mJ/cm2 for 20 times at wavelength of 254 nm. The samples were added with SDS-PAGE loading dye, heated for 5 min at 95° C., and resolved on 7% SDS-PAGE gel. The gel was dried and exposed to X-film, which was to be developed 3 days later.

Example 1

Effects of Treatment with Anisomycin, Emetine and Puromycin on the Normalized Luciferase Activity in pGL3-Basic Reporter Plasmid and Luc-1/pGL3-Basic Reporter Construct This example shows the effect of protein synthesis inhibitors (Aniosomycin, Emetine, and Puromycin) on the activity of the luciferase reporter gene in the absence or presence of hNIS promoter.

Figure 3:
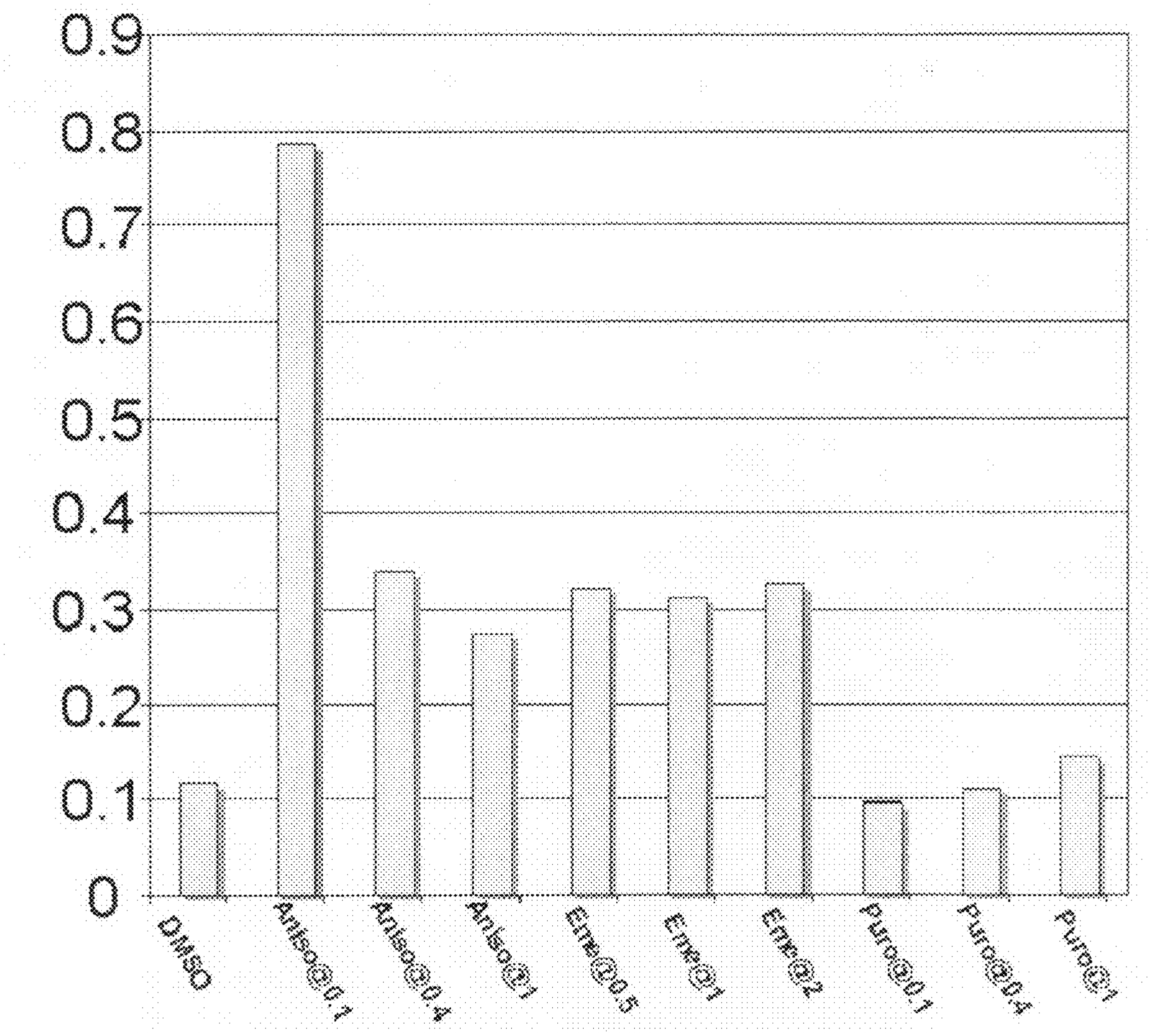
FIG. 3 shows the effects of treatment with Anisomycin, Emetine and Puromycin on the normalized luciferase activity in pGL3-basic reporter construct.

The pGL3-basic plasmid, together with phRG-B plasmid (as transfection efficiency control) and pUC-18 (as carrier) were transiently transfected into KAK-1 cells cultured under basal conditions supplemented with 0.01% DMSO (as solvent control), Anisomycin (0.1, 0.4, 1 μg/ml), Emetine (0.5, 1, 2 μg/ml) and Puromycin (0.1, 0.4, 1 μg/ml) respectively for 2 days. The cells were then lysed and firefly luciferase activity and *Renilla* luciferase activity were quantitated using a luminometer (FIG. 3).

Figure 4:
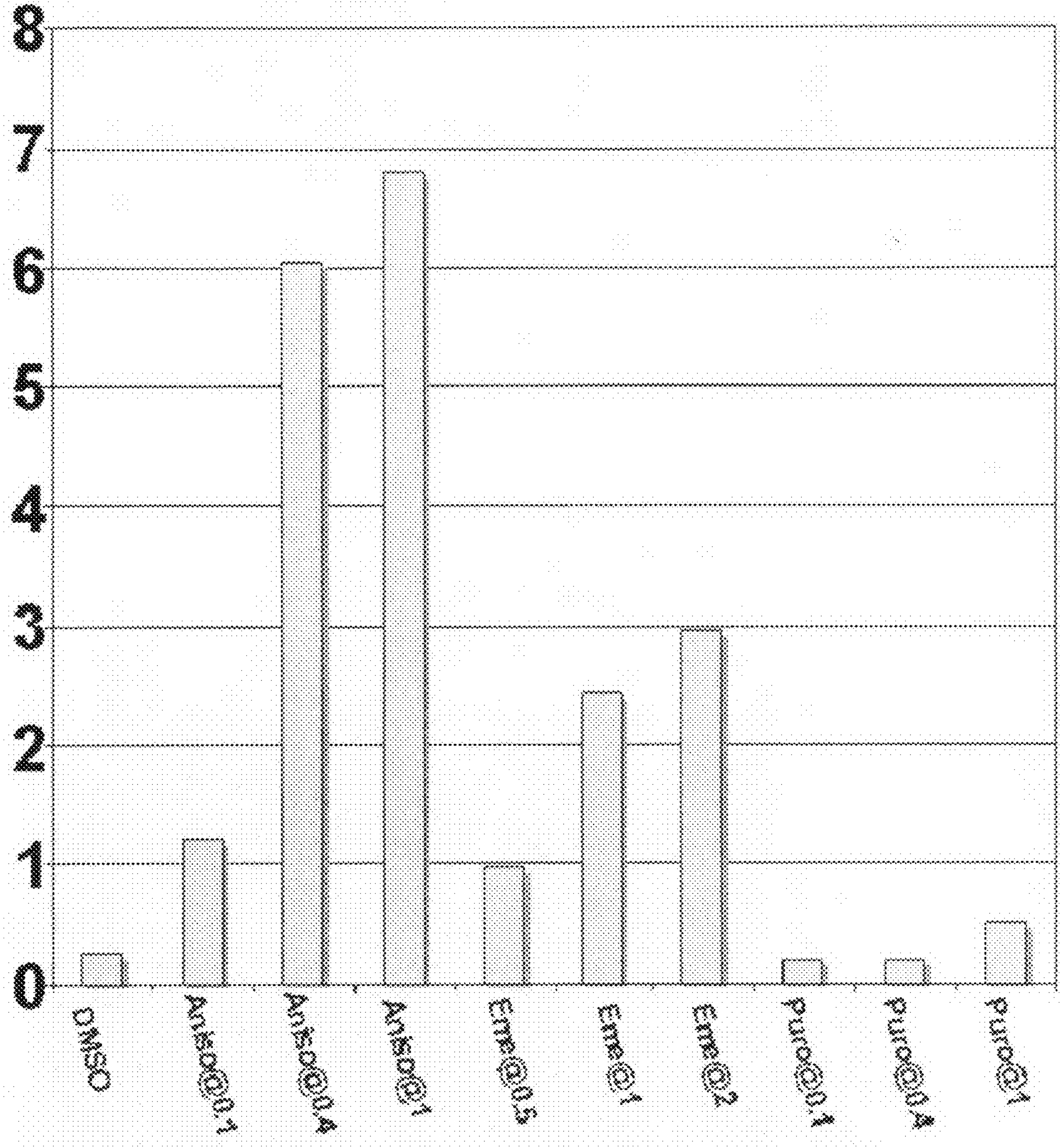
FIG. 4 shows the effects of treatment with Anisomycin, Emetine and Puromycin on the normalized luciferase activity in Luc-1/pGL3-basic reporter construct.

Luc-1/pGL3-basic reporter construct (Luc-1) was prepared containing the promoter region of the human sodium/iodide symporter gene (see Venkataraman et al. 1998 *Thyroid* 8:63-69 and U.S. Pat. No. 6,015,376; Genebank Accession Number: AF059566) from −1667 to −348 bp (FIG. 2) inserted into pGL3-basic luciferase vector at KpnI and HindIII site upstream of the luciferase coding sequence. The Luc-1/pGL3-basic construct, together with phRG-B plasmid (as transfection efficiency control) and pUC-18 (as carrier) were transiently transfected into KAK-1 cells cultured under basal conditions supplemented with 0.01% DMSO (as solvent control), Anisomycin (0.1, 0.4, 1 μg/ml), Emetine (0.5, 1, 2 μg/ml) and Puromycin (0.1, 0.4, 1 μg/ml) respectively for 2 days. The cells were then lysed and firefly luciferase activity and *Renilla* luciferase activity were quantitated using luminometer (FIG. 4).

As compared with the results with the pGL3-basic vector, treatment with Anisomycin at 0.4, 1 μg/ml and Emetine at 1, 2 μg/ml, dramatically stimulated the normalized luciferase activity driven by the 1.3 kb DNA sequence from human NIS promoter region in KAK-1 cells, while Puromycin treatment even at the highest concentration used did not stimulate the luciferase activity much. The result showed that a trans-active protein factor(s), binding to the hNIS promoter, represses luciferase gene transcription.

Example 2

Figure 1:
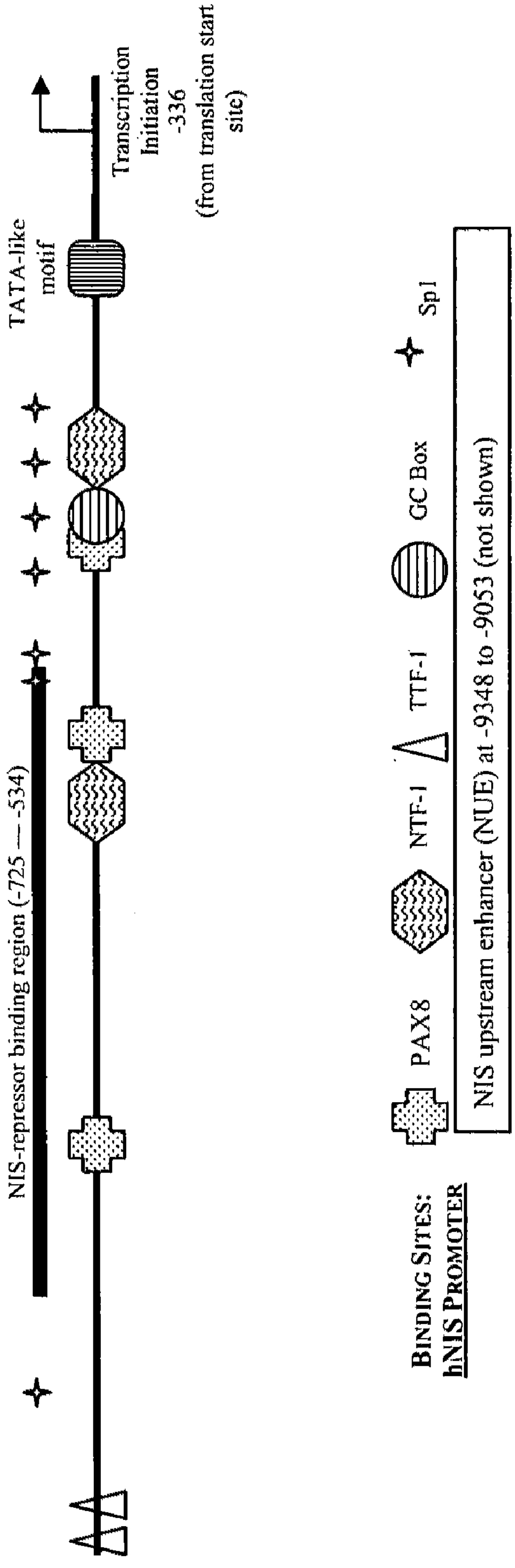
FIG. 1 is a representation of known transcription factor binding sites upstream of the hNIS gene coding region.

The Effects of Deletion of −724 to −534 bp Region from the Luc-1/pGL3-Basic Reporter Construct Here, the effects of the deletion of −725 to −534 bp region from the translation start site of the hNIS promoter (FIG. 1), designated as NIS-Repressor Binding Site (NRBS), on the expression of reporter gene was assessed.

Figure 5:
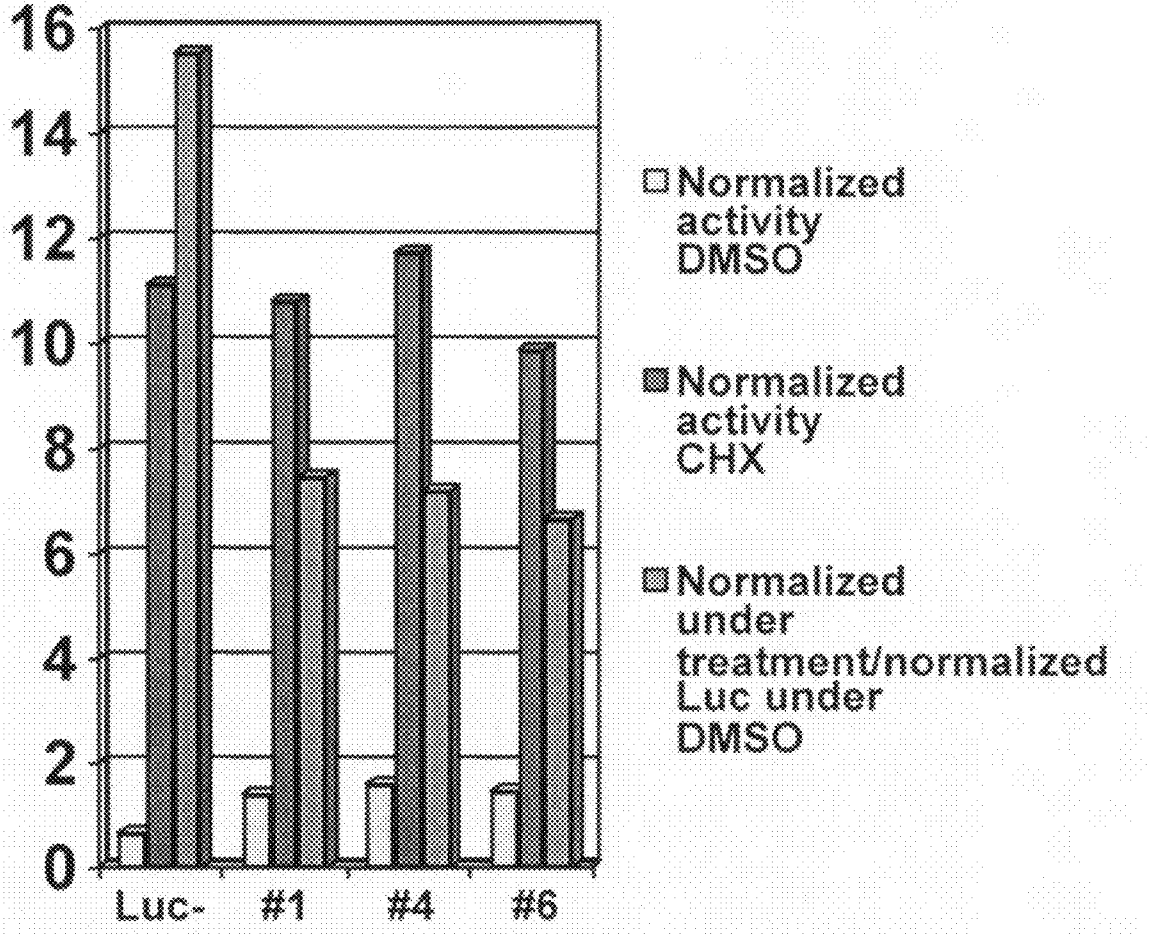
FIG. 5 shows the effects of deletion of −724 to −534 bp region from the Luc-1/pGL3-basic reporter plasmid, when treated with cyclohexamide.

As shown in FIG. 5, the #1, #4, #6 bar sets represent the results for different clones, in which the DNA fragment from −724 to −534 bp (SEQ ID NO:2) has been deleted from the Luc-1/pGL3-basic reporter plasmid. The plasmid DNA constructs, together with phRG-B plasmid (as transfection efficiency control) and pUC-18 (as carrier) were transiently transfected in to KAK-1 cells cultured at basal conditions supplemented with 0.01% DMSO (as solvent control) or CHX at 10 μg/ml for 2 days. The cells were lysed, followed by the quantitation of firefly luciferase and *Renilla* luciferase activities. The data in FIG. 5 show that deletion of the region from −724 to −534 increases the normalized luciferase activity by 100%. The data showed that the deletion resulted in increased luciferase expression.

Example 3

NIS-Repressor Binding Site (NRBS) is Refined by Site-Directed Mutagenesis

This example shows further refinement of the NRBS by site-directed mutations.

Figure 7:
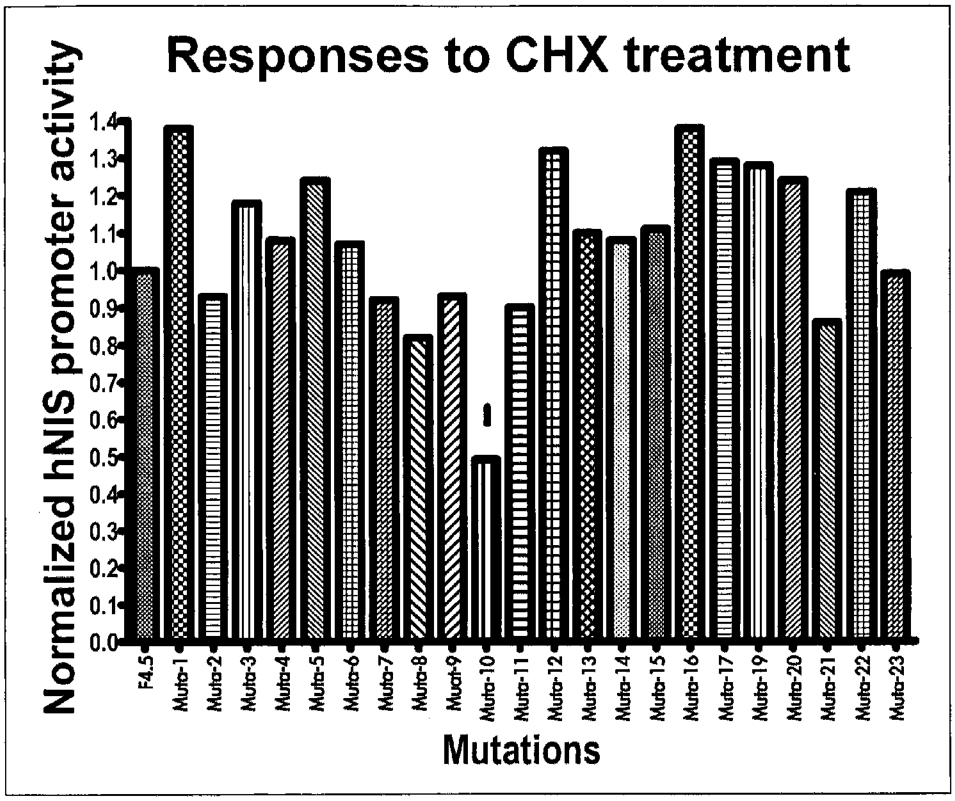
FIG. 7 shows the activities of the 22 mutant hNIS promoter constructs were normalized to the F4.5-pGL3-basic control vector. The luciferase activity from the reporter construct with mutation-10 in response to CHX treatment was decreased most dramatically, suggesting that the sequence in mutation-10 was most likely involved in the transcription-repressing activity of hNIS-repressor.

Previous work (Li et al. 2007, *JCin Endocrinol Metab* 92:1080-10874), utilizing serial deletions of hNIS promoter regions, provided evidence that a region between −774 to −478 bp (NRBS) is a binding site for a trans-active transcriptional repressor, NIS-repressor. In those studies, thyroid cancer cells treated with cycloheximide (CHX) had enhanced transcription of hNIS, both the native gene mRNA product and when studied using an hNIS promoter-luciferase reporter assay. To further refine the NRBS, site-directed mutations are introduced into NRBS. The effects of CHX treatment on 22 mutant hNIS promoter constructs are shown in FIG. 7 with data normalized to the F4.5-pGL3-basic control vector. The result demonstrates that mutation-10 resulted in a remarkable reduction of luciferase activity. In consideration of the activity of flanking mutations (mutations 8 to 11), it appears to refine the NRBS to a region from −653 to −621 bp from the hNIS translation start site (R-NRBS, Refined NRBS).

Example 4

Factors in KAK-1 Nuclear Extract Binds to NRBS

This example shows that NRBS is the binding site of nuclear factors identified as NIS-repressor.

Figure 8:
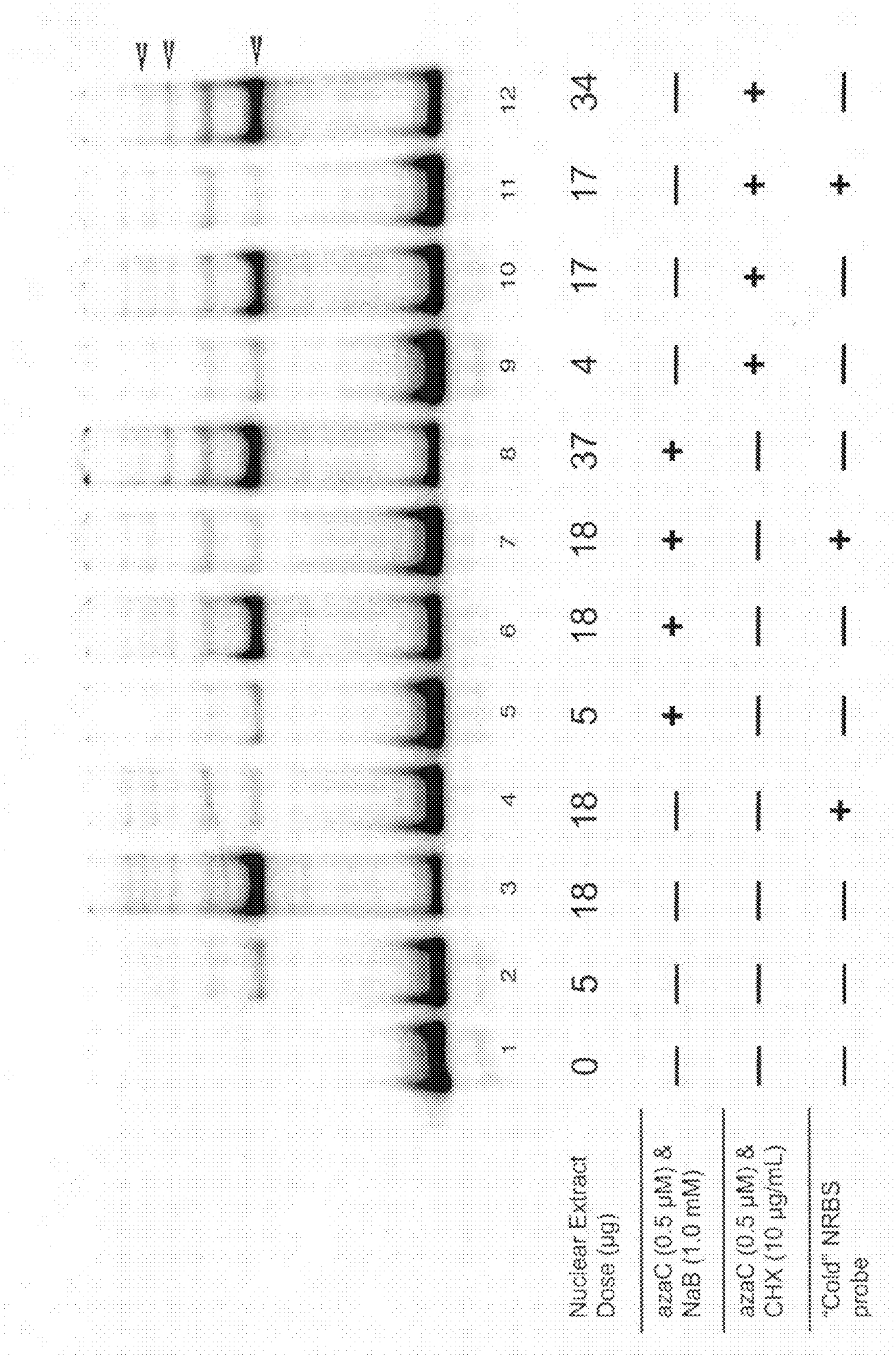
FIG. 8 shows electrophoretic mobility shift assay (EMSA) results using the radio-labeled EMSA probe-A (−684 to −565) and nuclear extracts from KAK-1 cells cultured under basal condition, KAK-1 cells cultured under basal condition supplemented with 5-azacytidine (azaC, 0.5 μM) plus sodium butyrate (NaB, 1 mM) or azaC plus cycloheximide (CHX, 10 μg/ml) for 2 days. Lane-1: hot probe-A (−684 to −565; Lane-2, 3: hot probe-A plus 5 and 18 μg nuclear extract from KAK-1, respectively; Lane-4: hot probe-A mixed with 18 μg nuclear extract from KAK-1 cells and 20-fold cold probe; lane-5, 6, 8: hot probe-A mixed with 5, 18, 37 μg nuclear extract from KAK-1 cells treated with azaC plus NaB, respectively; Lane-7: the mixture of lane-6 plus 20-fold cold probe-A; Lane-9, 10, 12: hot probe-A mixed with 4, 17, 34 μg nuclear extract from KAK-1 cells treated with azaC plus CHX, respectively; Lane-11: mixture of Lane-10 plus 20-fold cold probe-A. The arrows point to the mobility shifted bands, which are EMSA probe-A-specific.

Electrophoretic mobility shift assay was performed using radio-labeled NRBS (−684 to −565) oligonucleotides as a probe and nuclear extracts from KAK-1 cells cultured under basal conditions (not expressing hNIS mRNA), as well as with azaC/NaB and azaC/CHX treatments (shown in FIG. 8 on far left).

A PCR fragment (−684 to −565 bp of hNIS promoter; Probe A), encompassing the R-NRBS region including 31 bp upstream and 56 bp downstream from R-NRBS was used as a probe in an electrophoretic mobility shift assay (EMSA) utilizing KAK-1 nuclear extract.

The EMSA demonstrated a nuclear extract dose-related, probe-specific shift in three bands (arrows on right in FIG. 8). AzaC/NaB or AzaC/CHX treatment did not alter the density of the shifted bands. This EMSA result was identical for NPA87 cells (papillary thyroid cancer), similarly revealing evidence of NIS-repressor (FIG. 9).

Figure 9:
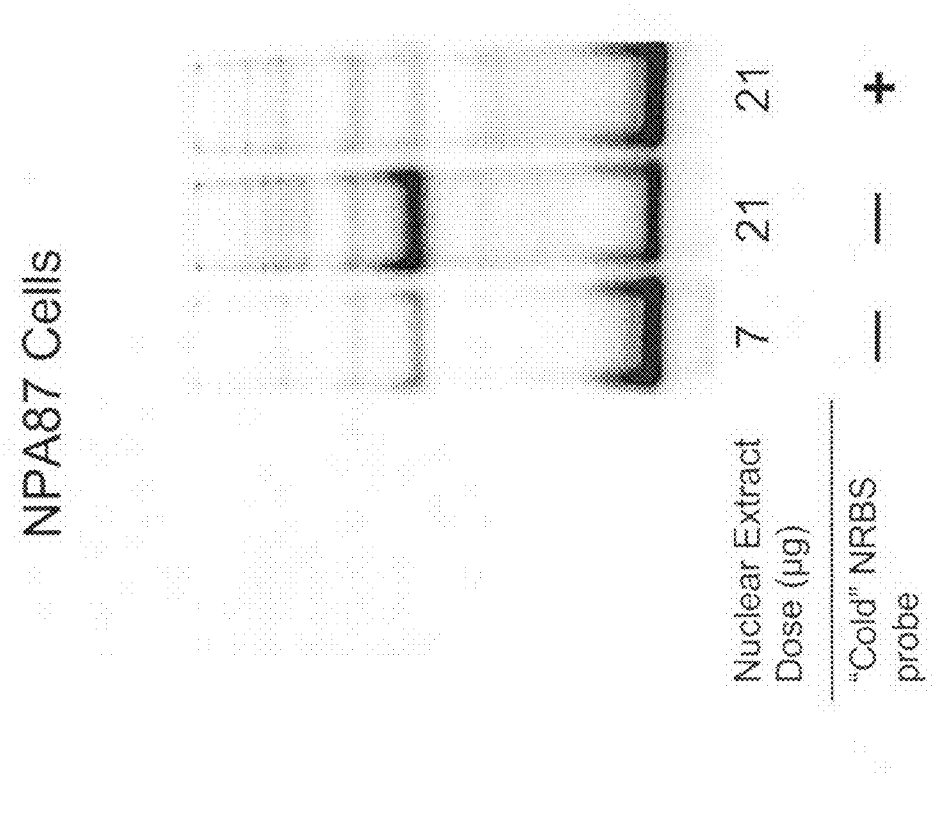
FIG. 9 is the EMSA results of lanes 9-11 in FIG. 14 relating to NPA-87 cells cultured under basal condition, and cold annealed probe-A. As mentioned in the description of FIG. 14, respectively; Lane-9, 10: hot probe-A mixed with 7 and 21 μg of nuclear extract from NPA-87 cells cultured under basal condition; Lane-11: mixture in Lane-10 plus 20-fold cold probe-A. This EMSA results indicated that NPA-87 cells, like KAK-1 cells, also contained the protein factor(s) that resulted in the shifted bands.
Figure 10:
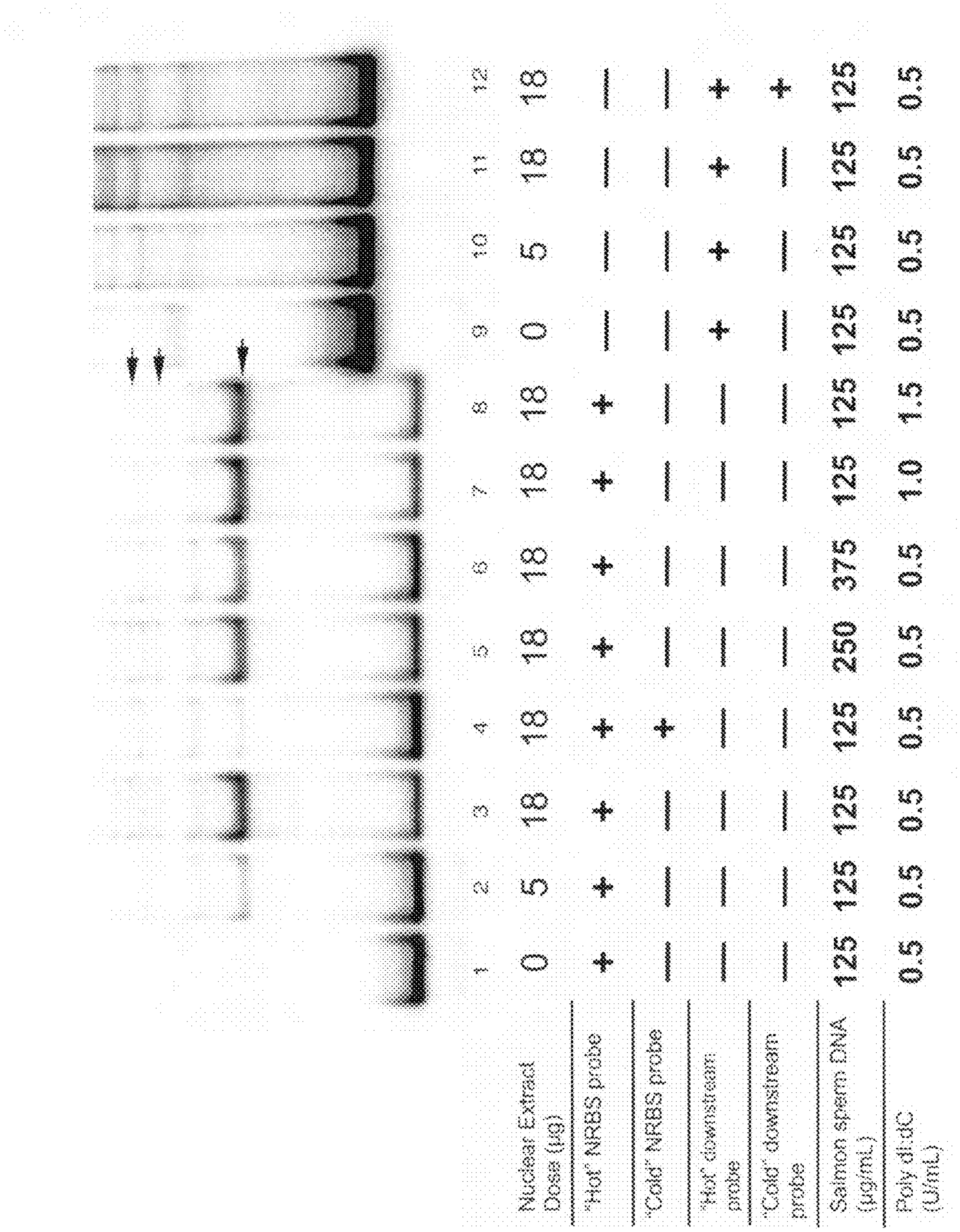
FIG. 10 shows the electrophoretic mobility shift assay (EMSA) results using radio-labeled EMSA probe-A or probe-B (−533 to −348) and nuclear extracts from KAK-1 cells cultured under basal condition. Lane-1: the hot probe-A; Lane-2, 3: hot probe-A mixed with 5, 18 μg nuclear extract from KAK-1 cells cultured under basal condition, respectively; Lane-4: mixture in Lane-3 plus 20-fold cold probe-A; Lane-5, 6: mixture in Lane-3 plus 1× and 2× more sonicated Salmon sperm DNA as inhibitor for non-specific protein-probe binding, respectively; Lane-7, 8: mixture in Lane-3 plus 1× and 2× more poly dI:dC as inhibitor for non-specific protein-probe binding, respectively; Lane-9: hot EMSA probe-B; Lane-10, 11: hot probe-B mixed with 5, 18 μg nuclear extract from KAK-1 cells cultured under basal condition, respectively; lane-12: mixture in Lane-11 plus 20-fold cold probe-B. The arrows point to the mobility shifted bands, which are EMSA-probe-A-specific. No mobility shift was found for EMSA probe-B-specific.

The radiograph from this assay revealed three probe A-specific bands, one major band and two minor bands in FIGS. 8, 9, and 10 (see FIG. 10, lanes 1-8). In FIG. 10, it was shown that the signals of these three lanes were increased with increased amounts of nuclear extract (lanes 2-3), diminished with addition of excess cold Probe A (lane 4), and not altered by addition of either more sonicated salmon sperm DNA (as non-specific DNA competitor; lanes 5-6) or more poly dI:dC (an artificial non-specific DNA competitor; lanes 7-8), demonstrating factor(s) in KAK-1 nuclear extract binding specifically to Probe A. An additional PCR fragment (−533 to −348 bp; Probe B), downstream from Probe A, failed to show these same mobility shift bands when used as an EMSA probe and incubated with the same KAK-1 nuclear extract. Also, the EMSA signal pattern seen with Probe B was unaltered by changed amounts of nuclear extract or by the addition of cold Probe B (lanes 9-12), demonstrating that this EMSA pattern resulted from the non-specific binding from the nuclear extract.

Example 5

Figure 11:
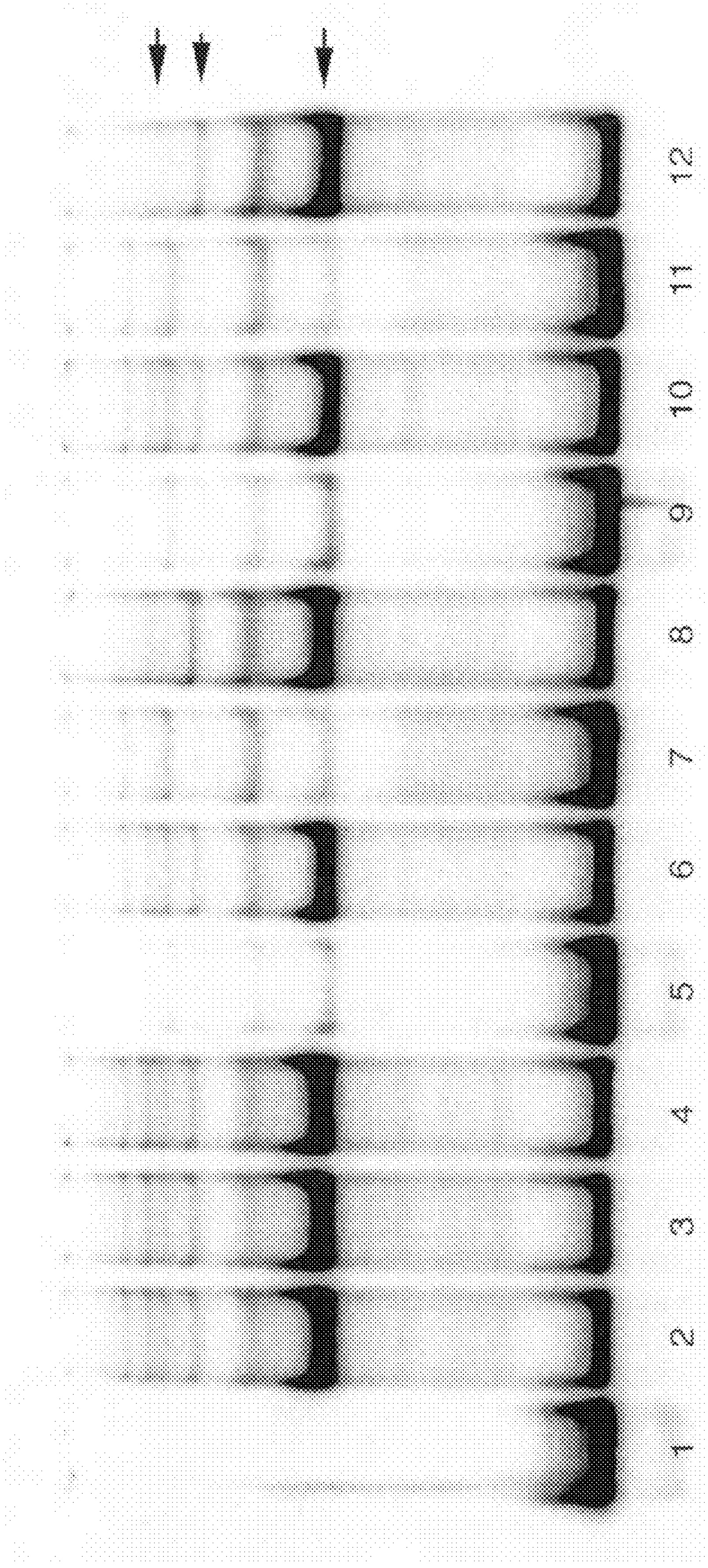
FIG. 11 shows the results of an electrophoretic mobility shift assay (EMSA) results using the radio-labeled EMSA probe-A and nuclear extracts from KAK-1 cells cultured under basal condition, KAK-1 cells cultured under basal condition supplemented with 5-azacytidine (azaC, 0.5 μM) or sodium butyrate (NaB, 1 mM) for 2 days. Lane-1: hot probe-A; Lane-2: hot probe-A plus 18 μg nuclear extract from KAK-1; Lane-3: mixture in Lane-2 plus 20-fold cold EMSA competitor probe-1 (−774 to −645); lane-4: mixture in Lane-2 plus 20-fold cold EMSA competitor probe-2 (−605 to −348); Lane-5, 6, 8: hot probe-A mixed with 4, 15, 29 μg nuclear extract from KAK-1 cells treated with azaC, respectively; Lane-7: the mixture of lane-6 plus 20-fold cold probe-A; Lane-9, 10, 12: hot probe-A mixed with 4.2, 17, 34 μg nuclear extract from KAK-1 cells treated with NaB, respectively; Lane-11: mixture of Lane-10 plus 20-fold cold probe-A. The arrows point to the mobility shifted bands, which are EMSA probe-A-specific.

The DNA Region in hNIS Promoter Responsible for the EMSA Signals is Narrowed Down to −648 to −620 bp Further refinement of the promoter region responsible for the EMSA signal seen with KAK-1 nuclear extract is shown in FIG. 11 (lanes 14), with different cold PCR fragments being used to compete against the radiolabeled Probe A in EMSA, Probe C spanning −774 to −645 bp and Probe D spanning −605 to −348 bp. These cold probes did not diminish the EMSA signals, denoting that the DNA sequence responsible for the gel-shift signals resided in the hNIS promoter region spanning −645 to −605 bp.

Figure 12:
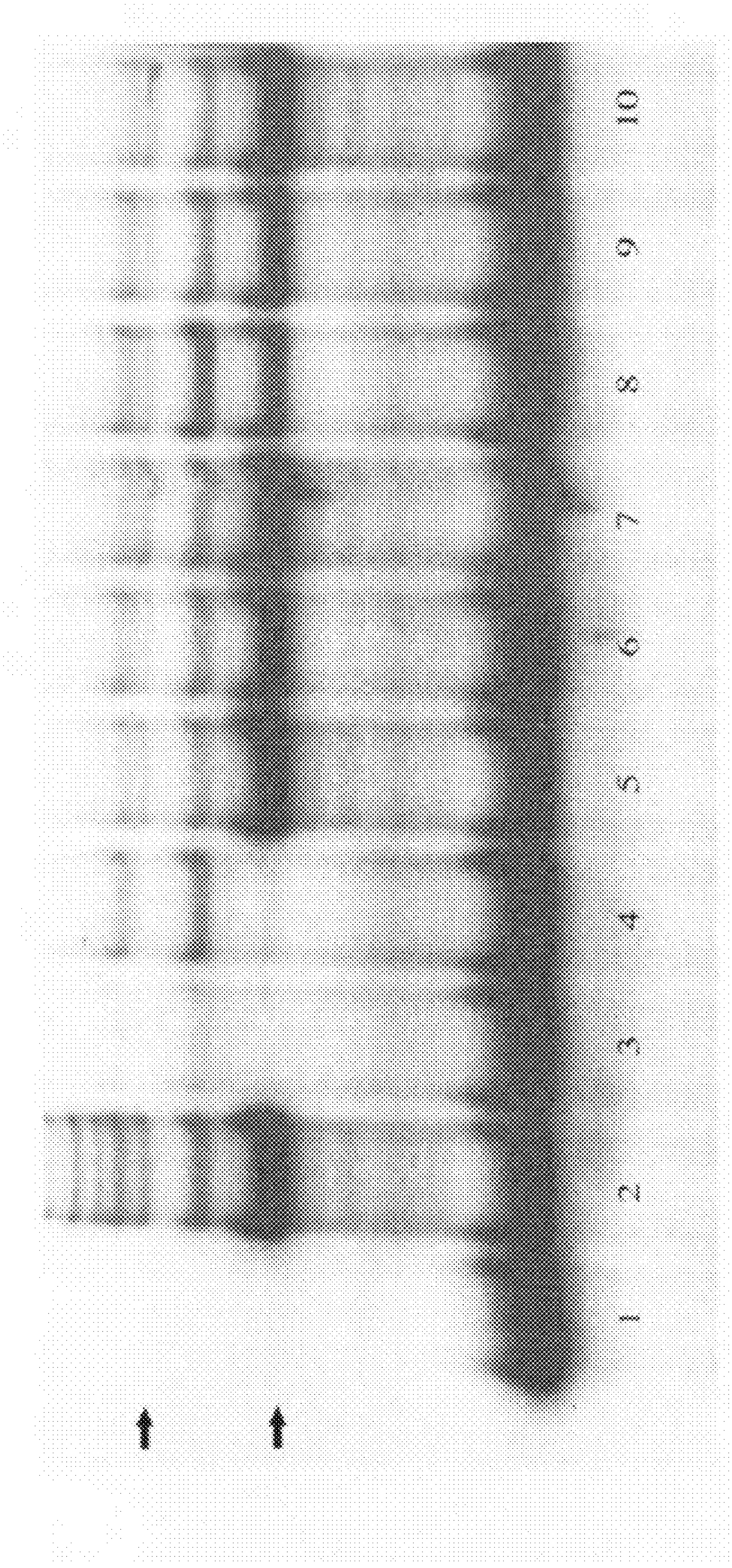
FIG. 12 shows the electrophoretic mobility shift assay results using the radiolabeled EMSA Probe A and the nuclear extract from KAK-1 cells cultured under basal conditions in the presence of different cold competitor oligos. Lane-1.

Furthermore, as shown in FIG. 12, excess cold double-stranded oligonucleotides, [Comp-2 (−633 to −595 bp, lane 5; also in lane 12 of FIG. 13), Comp-0.9 (−660 to −627 bp, lane-6), Comp-1.1 (−653 to −630 bp, lane 7), Comp-1.4 (−638 to −615 bp, lane 10)] were demonstrated to fail to compete against the radiolabeled Probe A in EMSA assay. In contrast, excess cold double-stranded oligonucleotide, Comp-1 (−653 to −615 bp), completely erased the characteristic gel-shift signal (lane 4, FIG. 12 and lane 11, FIG. 13) (SEQ ID NO. 153), while two other cold double-stranded oligonucleotides, Comp-1.2 (−648 to −625, lane 8, FIG. 12) (SEQ ID NO. 155j and Comp-1.3 (−643 to −620, lane 9, FIG. 12)(SEQ ID NO. 154D effectively competed against the radiolabeled Probe A in these studies. All of these results further refined the DNA sequence responsible for the characteristic gel-shift signal to the region of −648 to −620 bp in hNIS promoter (SEQ ID NO: 5), which is consistent with the R-NRBS region identified in functional studies using the luciferase assay with a series of site-directed hNIS promoter mutants.

Example 6

Treatment of KAK-1 Cells with azaC and Sodium Butyrate did not Alter the EMSA Signal Pattern of Nuclear Extract Probed with NRBS Since 5-azacytidine (azaC) and sodium butyrate were shown to increase hNIS transcription in KAK-1 cell, the effects of these agents on the gel shift patterns were studied to determine if their mechanism of activity is independent of protein binding to NRBS. The results (FIG. 11) showed that the gel shift pattern remained the same with nuclear extract prepared from KAK-1 cells treated with azaC (0.5 μM×3 days, FIG. 11; lanes 5-8). The signals increased in intensity with greater amounts of nuclear extract (lanes 5, 6, 8) and diminished with competition by cold Probe A (lane 7). Likewise, with nuclear extract prepared from cells treated with sodium butyrate (1 mM×3 days), there was a similar lack of effect upon the EMSA gel shift pattern (FIG. 11; lanes 9-12). This showed that the effects of azaC and sodium butyrate did not change the DNA-binding capability of the factors responsible for the EMSA gel shift pattern.

Example 7

Known Thyroidal Transcription Factors (AP-1, AP-2, CREB, Pax-8, Sp-1, TTF-1, and TTF-2) are Unlikely to be Responsible for the Gel-Shift Signals Additional studies were performed to further explore the specificity of the NRBS-nuclear extract binding (FIG. 13) and whether known thyroidal transcription factors were candidates for binding to NRBS as components of a NIS-repressor complex. In this study, it was evaluated whether cold oligonucleotides containing the consensus binding sites for thyroidal transcription factors could compete against Probe A in EMSA, thus altering the gel-shift signal pattern. FIG. 13 shows that cold double-stranded oligonucleotides containing the consensus binding sites for AP-1 (lane 4), AP-2 (lane 5), CREB (lane 6), PAX-8 (lane 7), Sp-1 (lane 8), TTF-1/Pax-8 (lane 9), TTF-2 (lane 10) failed to alter the gel-shift signal pattern seen using Probe A, showing that the nuclear extract constituents responsible for this EMSA pattern did not contain proteins that bound to these oligonucleotides. This implied that these specific thyroidal transcription factors are unlikely to be constituents of the NIS-repressor complex that binds to NRBS.

Example 8

Nuclear Extract Components Reduce Binding to Probe A at Higher Salt Concentrations This example demonstrates that the major EMSA gel-shift band, seen with KAK-1 nuclear extract and Probe A, gradually diminished in the presence of higher concentrations of KCl (FIG. 16, lanes 2-12). Extra addition of KCl to 0.2 M in the EMSA system reduced the gel shift signals by approximately 50% compared with the controls, in which no extra KCl was added. This was consistent with the typical salt elution conditions for protein transcription factors from their DNA binding sites.

Example 9

Identifying the NIS-Repressor Components Using LC/MS/MS

KAK-1 nuclear extract was incubated with biotinylated probe A and Dynabeads M-280 to isolate the bound protein factors. Eluates from the Dynabeads were analyzed by LC/MS/MS. Results of this analysis revealed the predominance of human PARP-1, with a Mascot score of 852 (probability based Mowse Score, >33 indicates identity, $p<0.05$) with 50 peptides and 459 amino acids matched, 42% of the sequence covered with 39 unique peptides as shown in bold in Table 4.

Biotinylated NRBS was bound to streptavidin-coated paramagnetic beads and incubated with KAK-1 nuclear extract, cultured under basal conditions producing no hNIS mRNA, when NIS-repressor would be at a high level. Beads were washed and eluted with 300 mM $NH_4HCO_3$. Eluate was acidified with formic acid, evaporated to dryness and digested with trypsin. Digests were acidified, dried, and reconstituted with 10 μL of 5% acetonitrile. Five μL was injected in a C18 capillary column, eluted with an acetonitrile-$H_2O$ gradient. Electron spray ionization with tandem mass spectrometry (LC/MS/MS) was performed on Finnigan LTQ with resulting MS-MS spectra analyzed using the Mascot (Matrix Science) protein database search engine against mammalian proteins in the SwissProt database. Applicants identified human PARP-1; Mascot score 852 (probability based Mowse Score, >33 indicates identity with $p<0.05$) with 50 peptides and 459 amino acids matched. The sequence coverage was 42% with 39 unique peptides (Tables 3 and 4).

TABLE 3

Peptides fragments identified from PARP-1

Accession: PARP1_HUMAN
Description: (P09874) Poly [ADP-ribose] polymerase-1
(EC 2.4.2.30) (PARP-1) (ADPRT) (NAD(+) ADP-ribosyltransferase
MOWSE Score: 852
Sequence Coverage: 42%
Mass: 112953 Da
Unique peptides: 39

| | |
|---|---|
| YLLK (SEQ ID NO:108) | SKLPKPVQDLIK (SEQ ID NO:128) |
| AMIEK (SEQ ID NO:109) | TTNFAGILSQGLR (SEQ ID NO:129) |
| ILTLGK (SEQ ID NO:110) | QQVPSGESAILDR (SEQ ID NO:130) |
| HSVKGLGK (SEQ ID NO:112) | MAIMVQSPMFDGK (SEQ ID NO:131) |
| GTNSYYK (SEQ ID NO:113) | KPPLLNNADSVQAK (SEQ ID NO:132) |
| LLWHGSR (SEQ ID NO:114) | HPDVEVDGFSELR (SEQ ID NO:133) |
| VGTVIGSNK (SEQ ID NO:115) | VVSEDFLQDVSASTK (SEQ ID NO:134) |

TABLE 3-continued

Peptides fragments identified from PARP-1

Accession: PARP1_HUMAN
Description: (P09874) Poly [ADP-ribose] polymerase-1
(EC 2.4.2.30) (PARP-1) (ADPRT) (NAD(+) ADP-ribosyltransferase
MOWSE Score: 852
Sequence Coverage: 42%
Mass: 112953 Da
Unique peptides: 39

| | |
|---|---|
| ELLIFNK (SEQ ID NO:116) | MVDPEKPQLGMIDR (SEQ ID NO:135) |
| KLTVNPGTK (SEQ ID NO:117) | TAEAGGVTGKGQDGIGSK (SEQ ID NO:136) |
| LYRVEYAK (SEQ ID NO:118) | MVDPEKPQLGMIDR (SEQ ID NO:137) |
| GIYFADMVSK (SEQ ID NO:119) | EELGFRPEYSASQLK (SEQ ID NO:138) |
| TLGDFAAEYAK (SEQ ID NO 120) | AMVEYEIDLQKMPLGK (SEQ ID NO:139) |
| DSEEAEIIRK (SEQ ID NO 121) | LEQMPSKEDAIEHFMK (SEQ ID NO:140) |
| MEEVKEANIR (SEQ ID NO:122) | GGAAVDPDSGLEHSAHVLEK (SEQ ID NO:141) |
| MIFDVESMKK (SEQ ID NO:123) | NREELGFRPEYSASQLK (SEQ ID NO:142) |
| AMVEYEIDLQK (SEQ ID NO:124) | VEMLDNLLDIEVAYSLLR (SEQ ID NO:143 |
| KGDEVDGVDEVAK (SEQ ID NO:125) | SLQELFLAHILSPWGAEVK (SEQ ID NO:144 |
| VFSATLGLVDIVK (SEQ ID NO:126) | HPDVEVDGFSELRWDDQQK (SEQ ID NO:145) |
| QIQAAYSILSEVQQAVSQGSSDSQILDLSNR (SEQ ID NO:146) | |
| RQIQAAYSILSEVQQAVSQGSSDSQILDLSNR (SEQ ID NO:147) | |
| IFPPETSASVAATPPPSTASAPAAVNSSASADKPLSNMK (SEQ ID NO:148) | |

TABLE 4

| PARP1 (EC 2.4.2.30) protein sequence. Peptides identified from PARP1 are in Bold | | | | | |
|---|---|---|---|---|---|
| 0001 | AESSDKLYRV | EYAKSGRASC | KKCSESIPKD | SLR**MAIMVQS** | **PMFDGK**VPHW |
| 0051 | YHFSCFWKVG | HSIR**HPDVEV** | **DGFSELRWDD** | **QQK**VKK**TAEA** | **GGVTGKGQDG** |
| 0101 | **IGSK**AEK**TLG** | **DFAAEYAK**SN | RSTCKGCMEK | IEKGQVRLSK | K**MVDPEKPQL** |
| 0151 | **GMIDR**WYHPG | CFVK**NREELG** | **FRPEYSASQL** | **K**GFSLLATED | KEALKKQLPG |
| 0201 | VKSEGKR**KGD** | **EVDGVDEVAK** | KKSKKEKDKD | SKLEKALKAQ | NDLIWNIKDE |
| 0251 | LKKVCSTNDL | **KELLIFNKQQ** | **VPSGESAILD** | **R**VADGMVFGA | LLPCEECSGQ |
| 0301 | LVFKSDAYYC | TGDVTAWTKC | MVKTQTPNRK | EWVTPKEFRE | ISYLKKLKVK |
| 0351 | KQDR**IFPPET** | **SASVAATPPP** | **STASAPAAVN** | **SSASADKPLS** | **NMKILTLGK**L |
| 0401 | SRNKDEVK**AM** | **IEK**LGGKLTG | TANKASLCIS | TKKEVEKMNK | K**MEEVKEANI** |
| 0451 | **RVVSEDFLQD** | **VSASTKSLQE** | **LFLAHILSPW** | **GAEVK**AEPVE | VVAPRGKSGA |
| 0501 | ALSKKSKGQV | KEEGINKSEK | RMKLTLK**GGA** | **AVDPDSGLEH** | **SAHVLEK**GGK |
| 0551 | **VFSATLGLVD** | **IVKGTNSYYK** | LQLLEDDKEN | RYWIFRSWGR | **VGTVIGSNKL** |
| 0601 | **EQMPSKEDAI** | **EHFMK**LYEEK | TGNAWHSKNF | TKYPKKFYPL | EIDYGQDEEA |
| 0651 | VK**KLTVNPGT** | **KSKLPKPVQD** | **LIKMIFDVES** | **MKKAMVEYEI** | **DLQKMPLGKL** |
| 0701 | SK**RQIQAAYS** | **ILSEVQQAVS** | **QGSSDSQILD** | **LSNR**FYTLIP | HDFGMK**KPPL** |
| 0751 | **LNNADSVQAK** | **VEMLDNLLDI** | **EVAYSLLR**GG | SDDSSKDPID | VNYEKLKTDI |
| 0801 | KVVDR**DSEEA** | **EIIRK**YVKNT | HATTHNAYDL | EVIDIFKIER | EGECQRYKPF |
| 0851 | KQLHNRR**LLW** | **HGSRTTNFAG** | **ILSQGLR**IAP | PEAPVTGYMF | GK**GIYFADMV** |
| 0901 | **SK**SANYCHTS | QGDPIGLILL | GEVALGNMYE | LKHASHISKL | PKGKHSVKGL |
| 0951 | GKTTPDPSAN | ISLDGVDVPL | GTGISSGVND | TSLLYNEYIV | YDIAQVNLKY |
| 1001 | LLKLKFNFKT | SLW (SEQ ID NO:149) | | | |

Example 10

Identifying PARP-1 as a Component of the NIS-Repressor Protein Complex using Chromatin Immunoprecipitation Assay In this example, the association of PARP-1 to endogenous hNIS promoter in KAK-1 cells under basal culture conditions was evaluated using ChIP assay.

KAK-1 cells under basal culture conditions were fixed with formaldehyde. The chromatin DNA was enzymatically sheared, followed by incubation with antibodies. Protein G-agarose beads were then added to capture the DNA/protein/antibody complex, which was then heated to reverse the crosslink between DNA and protein factors. The free genomic DNA was purified. The interaction between human PARP-1 and human NIS-repressor binding site (NRBS) was interrogated by PCR using NRBS-Forward (NRBS-F: 5' AGCACAATACGGCTTTGAGTG 3' SEQ ID NO:150) and NRBS-Reverse (NRBS-R: 5' CTCCATCCCCATGCACAC 3' SEQ ID NO:151) primer pair flanking NRBS. The PCR products were resolved in a 1.5%-agarose gel as shown in FIG. 17. The DNA bands in lanes 3 and 4 (with lengths of about 200 bp) of FIG. 17 show that NRBS was successfully amplified from the genomic DNA samples in which anti-PARP-1 antibodies were used in immunoprecipitation. The results demonstrate that PARP-1 is associated with the region from −708 to −551 bp of the hNIS promoter, covering R-NRBS, in KAK-1 cells under the same basal culture conditions in which there is no hNIS transcription.

Example 11

PARP-1 is Associated with Endogenous hNIS Promoter in KAK-1 Cells Under Basal Culture Conditions This example shows whether PARP-1 binds to endogenous hNIS promoter in KAK-1 cells under basal culture conditions using ChIP assay.

To evaluate whether purified PARP-1 is associated with NRBS, Applicants performed EMSA using commercial PARP-1 and radiolabeled Probe A (FIG. 18, lane 3). The commercial PARP-1 failed to produce any gel-shift band (lane 4). As PARP-1 was reported to bind to DNA using its N-terminal domain, the N-terminal DNA-binding domain (1-372 aa) from human PARP-1 were stably transfected into KAK-1 cells. Nuclear extract from multiple pooled positive clones from this transfection or a single positive clone from the same transfection experiment were incubated with labeled Probe A and subjected to EMSA (FIG. 18; lanes 6 & 10, respectively). The gel-shift bands produced were not appreciably different from those produced by nuclear extract from KAK-1 cells transfected with the empty vector (pCR3.1; lane 8) or those produced by parental KAK-1 nuclear extract (lane 2). Addition of cold Probe A, in each case, competed similarly against their respective matched lanes (lanes 3, 7, 9, & 11). These results showed that the N-terminal domain of human PARP-1 is not directly involved in binding to NRBS or has a much lower affinity compared with the endogenous whole PARP-1 molecules to influence the EMSA signals, especially when the expression level of the N-terminal DNA-binding domain level is lower than the endogenous PARP-1 level.

Example 12

Pharmacological Inhibition of hPARP-1 with PJ34 Increased hNIS Promoter Activity in Luciferase Reporter Assay PJ34 is a potent inhibitor for PARP-1. Its effect on hNIS transcription was determined using luciferase reporter assay with pGL3-basic, F4-pGL3-basic (containing hNIS promoter from −1252 to −348 bp) and F4Δ-pGL3-basic constructs (the same as F4-pGL3-basic but with deletion of sequence from −667 to −588 bp, encompassing R—NRBS). The results were summarized in FIG. 19, revealing that: 1) the normalized luciferase activities from F4-pGL3-basic and F4Δ-pGL3-basic were increased significantly ($p<0.05$, t-test) compared with that from pGL3-basic control vector in the absence or presence of PJ34 treatment; 2) the normalized luciferase activities from F4Δ-pGL3-basic were increased significantly ($p<0.05$, t-test) compared with that from F4-pGL3-basic in the absence of PJ34 treatment; and 3) treatment with PJ34 at 30 μM for 2 days significantly ($p<0.05$, t-test) stimulated luciferase activity from all the constructs compared with their counterparts without PJ34 treatment. These results demonstrated that pharmacological inhibition of hPARP-1 with PJ34 increased hNIS promoter activity. The increased luciferase activity seen with the F4Δ-pGL3-basic construct with PJ34 treatment, compared to the same construct without PJ34 treatment, showed that PARP-1 enzymatic activity has inhibitory effects on NIS transcription that are operative despite the absence of the NIS-repressor binding site.

Example 13

Pharmacological Inhibition of hPARP-1 Stimulates Endogenous hNIS Transcription, Shown by qRT-PCR Assay The qRT-PCR assay was used to measure hNIS mRNA levels after different treatments in KAK-1 cells.

As previously shown, multiple agents that are thought to affect promoter methylation and histone acetylation are able to increase the transcription of hNIS mRNA dramatically, exemplified by the combination of azaC and NaB (Table 5).

Likewise, both azaC and CHX stimulate hNIS mRNA singly, but when applied together their effect is synergistic. This effect of CHX has been postulated to be consequent to inhibition of the NIS-repressor. If the effects of NIS-repressor were solely due to the enzymatic activity of PARP-1, then the effects of CHX should be recapitulated by treatment with PJ34. Although PJ34 alone will stimulate hNIS mRNA more than CHX alone, it lacks any synergistic effect when combined with azaC. This showed that the synergy in enhancing hNIS mRNA transcription seen with CHX and azaC can be consequent to co-inhibition of other protein constituents of the NIS-repressor complex besides PARP-1. This idea is further supported by the results seen with the triple combination of azaC, CHX and PJ34 in comparison to the combination of azaC and CHX, seen in Table 5.

TABLE 5

Relative hNIS mRNA levels under treatment with 5-azacytidine (azaC), sodium butyrate (NaB), cycloheximide (CHX), 3-aminobenzamide (3-AB), PJ34, or their combinations.

| Treatment | Relative hNIS mRNA level |
|---|---|
| control | 1 (4 copies/$10^9$ 18s RNA) |
| azaC | 5 |
| azaC/NaB | 372 |
| CHX | 4 |
| azaC/CHX | 182 |
| 3-AB | 1 |
| azaC/3-AB | 3.5 |
| PJ34 | 26 |
| azaC/PJ34 | 29 |
| azaC/CHX/PJ34 | 221 |

Since the CHX effects are thought to diminish the NIS-repressor complex, likely including PARP-1, the addition of PJ34 to the CHX would not be expected to enhance the effects of CHX alone.

Although 3-aminobenzamide (3-AB) is known as an inhibitor of PARP-1 enzymatic activity, it is much less potent than PJ34. Consistent with this, 3-AB is not effective in stimulating hNIS mRNA transcription and did not enhance the effects of azaC.

Example 14

Co-Transfection of KAK-1 Cells with Plasmids, Expressing Either PARP-1 DNA-Binding Domain or PARP-1 Enzymatic Domain, and Plasmids Containing NIS Promoter Constructs Elucidates PARP-1 Effects on the NIS Promoter PARP-1 has three structural domains, including: an N-terminal DNA-binding domain containing two zinc fingers, an automodification domain containing a breast cancer susceptibility protein C terminus, and a C-terminal catalytic domain. The above examples demonstrated that PARP-1 is associated with the endogenous hNIS promoter region and that pharmacological inhibition of hPARP-1 with PJ34 stimulates both hNIS promoter activity and endogenous hNIS mRNA level. It is plausible that the DNA-binding domain of PARP-1 mediates its interaction with the NRBS as part of the NIS-repressor complex. This was evaluated by transfecting KAK-1 cells with an expression plasmid for the PARP-1 DNA-binding domain, without the other domains of PARP-1, expecting this to provide an inhibition of endogenous PARP-1 activity and restore NIS promoter activity. This technique has been utilized to provide dominant-negative effects upon PARP-1 in other systems (Schreiber et al. 1995 *Proc Natl Acad Sci USA* 92:4753-47579).

FIG. 20 reports the data regarding this effect. KAK-1 cells were co-transfected with a luciferase reporter construct, a hybrid protein expression construct, and the *Renilla* luciferase plasmid. The luciferase-reporter constructs included: pGL3-basic (empty vector as control), F4-pGL3-basic (full length hNIS promoter), F4Δ-pGL3-basic (hNIS promoter with R-NRBS deleted), and F4ΔGAL-pGL3-basic (GAL4 DNA-binding site inserted into hNIS promoter in place of R-NRBS). The hybrid protein expression constructs include: pUC18 (as negative control), DBD (PARP-1 DNA-binding domain), pBD-PARP-En(+) (fusion protein of GAL4 DNA-binding domain and wild-type PARP-1 enzymatic domain), pBD-PARP-En(−) (fusion protein of GAL4 DNA-binding domain and C908R mutant defective PARP-1 enzymatic domain) and pBD-NF-κB (fusion protein of GAL4 DNA-binding domain and NF-κB transcription activation domain that constitutively activates promoters with GAL4 DNA-binding sites). The *Renilla* luciferase plasmid is co-transfected to normalize the transfection efficiency.

Data in FIG. 20 showed that the NIS promoter region, with or without R-NRBS, increased luciferase activity compared to the pGL3-basic (empty vector). Deletion of R-NRBS enhanced luciferase activity over that of the full length NIS promoter basal activity, regardless of whether a GAL4 DNA binding domain was inserted in its place when no extra hybrid protein is expressed using the pUC18 control. In the second set of co-transfections, expression of DBD seemed to increase the luciferase activity of the constructs with full-length promoter (F4-pGL3-basic) to a similar level as constructs missing NRBS (F4Δ-pGL3-basic). This showed the possibility that DBD interferes with endogenous NIS-repressor. In the third set of co-transfections, fusion protein of GAL4 DNA-binding domain and wild-type PARP-1 enzymatic domain, (pBD-PARP-En(+), had no effect upon any of the reporter constructs except for the F4ΔGAL-pGL3-basic reporter. This reveals that PARP-1 without its DNA-binding domain, placed in proximity to the R-NRBS locus of the promoter, inhibits promoter activity. Such inhibition is independent of PARP-1 enzymatic activity, as revealed by the fourth set of co-transfections using pBD-PARP-En(−) containing defective PARP-1 enzymatic domain. The fifth set of co-transfections demonstrated a robust response of luciferase activity to the NF-κB transcription activation domain targeted by GAL4 DNA-binding domain, verifying the selectivity of the GAL4 DNA-binding domain.

Example 15

Electrophoretic Analysis of NRBS Cross-Linked with Nuclear Extract Shows that NIS-Repressor is a Protein Complex To test the composition of hNIS-repressor, Comp-1 probe, consisting of double-stranded DNA (corresponding to the most tightly defined portion of the NRBS; −653 to −615 bp) was radiolabeled, mixed with nuclear extract, then cross-linked by UV exposure and resolved on SDS-PAGE. The data from this example demonstrated three major regions that were diminished in intensity by addition of cold Comp-1 probe (A, B, & C). See FIG. 21. These likely resulted from multiple protein factors bound to the Comp-1 probe and showed that NIS-repressor, bound to NRBS, is a protein complex.

Other embodiments of the disclosure will be apparent to those skilled in the art from consideration of the specification and practice of the disclosure disclosed herein. It is intended that the specification and examples be considered as exemplary only. The skilled artisan readily recognizes that many other embodiments are encompassed by the disclosure. All publications and patents cited and sequences identified by accession or database reference numbers in this disclosure are incorporated by reference in their entirety. To the extent the material incorporated by reference contradicts or is inconsistent with the present specification, the present specification will supersede any such material. The citation of any references herein is not an admission that such references are prior art to the present disclosure.

What is claimed is:

1. An isolated nucleic acid sequence selected from the group consisting of a sequence from −645 to −605 (SEQ ID NO:4) upstream of the translation start site of human sodium iodide symporter (NIS) gene, a sequence from −648 to −620 (SEQ ID NO:5) upstream of the translation start site of human sodium iodide symporter (NIS) gene, and a sequence that is at least 85% identical to the full length or SEQ ID No: 4 or SEQ ID NO: 5; wherein the nucleic acid binds to a sodium iodide symporter (NIS)-repressor protein complex.

2. The isolated nucleic acid sequence of claim 1, wherein said isolated nucleic acid sequence is SEQ ID NO: 4.

3. The isolated nucleic acid sequence of claim 1, wherein said isolated nucleic acid sequence is SEQ ID NO: 5.

4. The isolated nucleic acid sequence of claim 1, wherein said isolated nucleic acid sequence is a sequence that is at least 85% identical to the full length of SEQ ID NO: 4.

5. The isolated nucleic acid sequence of claim 1, wherein said isolated nucleic acid sequence is a sequence that is at least 85% identical to the full length of SEQ ID NO: 5.

6. The isolated nucleic acid sequence of claim 1, wherein said isolated nucleic acid sequence is SEQ ID NO: 154 or SEQ ID NO: 155.

7. An isolated nucleic acid sequence that is SEQ ID NO: 153.

* * * * *

SEQUENCE LISTING

```
<160> NUMBER OF SEQ ID NOS: 155

<210> SEQ ID NO 1
<211> LENGTH: 1801
<212> TYPE: DNA
<213> ORGANISM: Homo sapiens

<400> SEQUENCE: 1

ggagacgggg tcttgctgtg ctgcccaggc tggagtgctg tgcagttctc gaccacagct      60

cattgcagcc tcgaacttcc acgctcaagc gatcctccca cttcagcctt ctgagtagct     120

gggattacag gcatgtgcca ccacgcctcg ctaatattgt atttttcata cagacaagat     180

ctcactatgt tgctcagggt agtctcgaat tctgggactc aaatgatcct cccacttcag     240

cctcccaaag tgctgggatt acaggcataa gccatcatgc ccggcctctg acgctgtttc     300

tttcaacccc caggatttca gattccacca gcttatggag aagggaacca agtttgagat     360

gcgtgattgc ccagaaagtt ggaggctgag ctgagacttg aacccagaga ccagaacctc     420

cagaggtcaa agtcctcctg ggtcccccag agaagggccc tgagatgaca gctcgttggt     480

cctcatggaa gcgtgacccc cccagtagac tttctcccac acccaacctt ggtttcctca     540

tctatatgat agggacaagc cagactctac ctccctggtg gtcatggtct ccgcttattc     600

gggttcataa ccttaaaggc ccctcgcacc acctcagtga gccatttatg cctggcacag     660

ggccaactct cagtgcatat ctgcaaagga accaatgaat gaatgaatga agtgacaaat     720

gaataaagga ataaatgaat gaggcactta tcatgtacca ggctttcgtt accacgtccc     780
```

-continued

```
atttattcct ctgaggcagg gtctatttta tccttgttac agatggggaa actaaggccc    840

agggaggagc aaagtcttcc ccaagtatgt acccactcag aacttgagct ctgaatgtct    900

cccacccagc ttagcccaag agcggggttc agtgatgccc accccctaag gctctagaga    960

aagggggtag gcccacatgc cagtttgggg gtggtaaagc caggtaagtt ttctttatgg   1020

gtcccctgaa accctgaaag tgaaccccag tcctgcatga aagtgagctc cccatagctc   1080

aaggtattca agcacaatac ggctttgagt gctgaagcag gctgtgcagg cttggatagt   1140

gacatgccct ttttgagcct caatttcccc acctgtcaac agcagacagt gacagctgtg   1200

atcaggggat cacagtgcat ggggatgggt gtgtgcatgg ggatggaggg gcatttggga   1260

gccctccccg ataccacccc ctgcagccac ccagatagcc tgtcctggcc tgtctgtccc   1320

agtccagggc tgaaagggtg cgggtcctgc ccgcccctag gtctggaggc ggagtcgcgg   1380

tgacccggga gcccaataaa tctgcaaccc acaatcacga gctgctcccg taagccccaa   1440

ggcgacctcc agctgtcagc gctgagcaca gcgcccaggg agagggacag acagccggct   1500

gcatgggaca gcggaaccca gagtgagagg ggaggtggca ggacagacag acagcagggg   1560

cggacgcaga gacagacagc ggggacaggg aggccgacac ggacatcgac agcccataga   1620

ttcctaaccc agggagcccc ggcccctctc gccgcttccc accccagacg gagcggggac   1680

aggctgccga gcatcctccc acccgccctc cccgtcctgc ctcctcggcc cctgccagct   1740

tcccccgctt gagcacgcag ggcgtccgag gacgcgctgg gcctccgcac ccgccctcat   1800

g                                                                   1801
```

<210> SEQ ID NO 2
<211> LENGTH: 191
<212> TYPE: DNA
<213> ORGANISM: Homo sapiens

<400> SEQUENCE: 2

```
tagctcaagg tattcaagca caatacggct ttgagtgctg aagcaggctg tgcaggcttg     60

gatagtgaca tgcccttttt gagcctcaat ttccccacct gtcaacagca gacagtgaca    120

gctgtgatca ggggatcaca gtgcatgggg atgggtgtgt gcatggggat ggaggggcat    180

ttgggagccc t                                                         191
```

<210> SEQ ID NO 3
<211> LENGTH: 727
<212> TYPE: DNA
<213> ORGANISM: Homo sapiens

<400> SEQUENCE: 3

```
tagctcaagg tattcaagca caatacggct ttgagtgctg aagcaggctg tgcaggcttg     60

gatagtgaca tgcccttttt gagcctcaat ttccccacct gtcaacagca gacagtgaca    120

gctgtgatca ggggatcaca gtgcatgggg atgggtgtgt gcatggggat ggaggggcat    180

ttgggagccc tccccgatac caccccctgc agccacccag atagcctgtc ctggcctgtc    240

tgtcccagtc cagggctgaa agggtgcggg tcctgcccgc ccctaggtct ggaggcggag    300

tcgcggtgac ccgggagccc aataaatctg caacccacaa tcacgagctg ctcccgtaag    360

ccccaaggcg acctccagct gtcagcgctg agcacagcgc ccagggagag ggacagacag    420

ccggctgcat gggacagcgg aacccagagt gagaggggag gtggcaggac agacagacag    480

caggggcgga cgcagagaca gacagcgggg acagggaggc cgacacggac atcgacagcc    540

catagattcc taacccaggg agccccggcc cctctcgccg cttcccaccc cagacggagc    600
```

-continued

```
ggggacaggc tgccgagcat cctcccaccc gccctccccg tcctgcctcc tcggcccctg    660

ccagcttccc ccgcttgagc acgcagggcg tccgaggacg cgctgggcct ccgcacccgc    720

cctcatg                                                              727


<210> SEQ ID NO 4
<211> LENGTH: 41
<212> TYPE: DNA
<213> ORGANISM: Homo sapiens

<400> SEQUENCE: 4

gagcctcaat ttccccacct gtcaacagca gacagtgaca g                         41


<210> SEQ ID NO 5
<211> LENGTH: 29
<212> TYPE: DNA
<213> ORGANISM: Homo sapiens

<400> SEQUENCE: 5

tttgagcctc aatttcccca cctgtcaac                                       29


<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

ctgcgtggct ctctcagtc                                                  19


<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

ccctccagct ccttctgc                                                   18


<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

atggtgacca cgggtgacg                                                  19


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

ttattcctag ctgcggtatc c                                               21


<210> SEQ ID NO 10
```

<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggtaccgg agcaaagtct tccccaag 28

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaagcttgg aggtcgcctt ggggcttac 29

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaaaaggtat tcaagcacaa tac 23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttttggggag ctcactttca tgc 23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaaagcacaa tacggctttg agt 23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttccttgag ctatggggag ctc 23

<210> SEQ ID NO 16
<211> LENGTH: 23
<212> TYPE: DNA

-continued

<213> ORGANISM: Artificial Sequence
<220> FEATURE:
<223> OTHER INFORMATION: Description of Artificial Sequence: Synthetic
primer

<400> SEQUENCE: 16
aaattgagtg ctgaagcagg ctg 23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
tttattgtgc ttgaatacct tga 23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
aaaaagcagg ctgtgcaggc ttg 23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
ttttcaaagc cgtattgtgc ttg 23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
aaatgcaggc ttggatagtg aca 23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
tttgcttcag cactcaaagc cgt 23

<210> SEQ ID NO 22
<211> LENGTH: 24
<212> TYPE: DNA
<213> ORGANISM: Artificial Sequence
<220> FEATURE:

-continued

<223> OTHER INFORMATION: Description of Artificial Sequence: Synthetic primer

<400> SEQUENCE: 22
aaagatagtg acatgccctt tttg 24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ttttgcacag cctgcttcag cac 23

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
aaatgccctt tttgagcctc aattt 25

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ttttatccaa gcctgcacag cct 23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
aaatttgagc ctcaatttcc cca 23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tttatgtcac tatccaagcc tgc 23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
aaacaatttc cccacctgtc aac 23

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tttaaaaagg gcatgtcact atcc 24

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
aaactgtcaa cagcagacag tga 23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tttaaattga ggctcaaaaa ggg 23

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
aaaacagcag acagtgacag ctgt 24

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tttgtgggga aattgaggct caa 23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 34

-continued aaaacagtga cagctgtgat cag 23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
tttttgacag gtggggaaat tga 23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
aaagctgtga tcaggggatc aca 23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
ttttgtctgc tgttgacagg tgg 23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
aaaatcaggg gatcacagtg cat 23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
ttttgtcact gtctgctgtt gac 23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
aaaatcacag tgcatgggga tgg 23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
tttatcacag ctgtcactgt ctg 23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
aaagcatggg gatgggtgtg tgc 23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
tttatcccct gatcacagct gtc 23

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
aaaggatggg tgtgtgcatg g 21

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
tttactgtga tcccctgatc aca 23

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
aaagcatggg gatggagggg ca 22

-continued

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tttccatccc catgcactgt gat 23

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
aaaggatgga ggggcatttg g 21

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
tttacacacc catccccatg cac 23

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
aaaaggggca tttgggagcc 20

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
tttccatgca cacacccatc cc 22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
aaaatttggg agccctcccc ga 22

<210> SEQ ID NO 53
<211> LENGTH: 22

<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
tttccatccc catgcacaca cc 22

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
aaacctcccc gataccaccc cct 23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
tttaaatgcc cctccatccc cat 23

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
gatcctatcc ctatgatgtg cccgactatg cttccggtac 40

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 57
cggaagcata gtcgggcaca tcatagggat ag 32

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
ctacccttac gacgttcctg actacgccag cctctaat 38

<210> SEQ ID NO 59
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
ctagattaga ggctggcgta gtcaggaacg tcgtaagggt aggt 44

<210> SEQ ID NO 60
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
aggctagcgc caccatggcg gagtcttcgg ataagctc 38

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
acggatccgg agggcggagg cgtggccg 28

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
tgcgtatgac ttggaagtca tc 22

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
gcctcgagtt accacaggga ggtcttaaaa ttg 33

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
gatcctcgga caaggatagt a 21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
agcttactat ccttgtccga g 21

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
tccctgagac gtatggcggt agttggcact cttgg 35

<210> SEQ ID NO 67
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
ccaagagtgc caactaccgc catacgtctc aggga 35

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
gtggtacctg atagggacaa gccagactc 29

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
agggatccgc ctgcacagcc tgcttcag 28

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
agggatcctc gagacagtgc atggggatgg gt 32

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
agggatcctt gcatgcctgc aggtc 25

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
agctcgagcc ctctagagtc tccgct 26

<210> SEQ ID NO 73
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
gtgacatgcc ctttttgagc ctcaatttcc ccac 34

<210> SEQ ID NO 74
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
gtggggaaat tgaggctcaa aaagggcatg tcac 34

<210> SEQ ID NO 75
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
gccctttttg agcctcaatt tccccacctg tcaacagca 39

<210> SEQ ID NO 76
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
tgctgttgac aggtggggaa attgaggctc aaaaagggc 39

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77 gcccttttg agcctcaatt tccc 24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
gggaaattga ggctcaaaaa gggc 24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
ttttgagcct caatttcccc acct 24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
aggtggggaa attgaggctc aaaa 24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
agcctcaatt tccccacctg tcaa 24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
ttgacaggtg gggaaattga ggct 24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
caatttcccc acctgtcaac agca 24

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
tgctgttgac aggtggggga aattg 25

<210> SEQ ID NO 85
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 85
tccccacctg tcaacagcag acagtgacag ctgtgatca 39

<210> SEQ ID NO 86
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 86
tgatcacagc tgtcactgtc tgctgttgac aggtgggga 39

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
cgcttgatga gtcagccgga a 21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
ttccggctga ctcatcaagc g 21

<210> SEQ ID NO 89
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
gatcgaactg accgcccgcg gcccgt 26

<210> SEQ ID NO 90

-continued

<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
acgggccgcg ggcggtcagt tcgatc 26

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
agagattgcc tgacgtcaga gagctag 27

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctagctctct gacgtcaggc aatctct 27

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
attcgatcgg ggcggggcga gc 22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gctcgccccg ccccgatcga at 22

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cactgcccag tcaagtggtt cttga 25

<210> SEQ ID NO 96
<211> LENGTH: 25
<212> TYPE: DNA

-continued

<213> ORGANISM: Artificial Sequence
<220> FEATURE:
<223> OTHER INFORMATION: Description of Artificial Sequence: Synthetic
oligonucleotide

<400> SEQUENCE: 96
tcaagaacca cttgactggg cagtg 25

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
gagggagttc ctgtgactag cagagaaaac aaagtgagcc ac 42

<210> SEQ ID NO 98
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 98
gtggctcact ttgttttctc tgctagtcac aggaactccc tc 42

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
cagctgctct atgaagtgtg aagaa 25

<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
ttcttcacac ttcatagagc agctg 25

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 101
aaaaagcagg ctgtgcaggc ttg 23

<210> SEQ ID NO 102
<211> LENGTH: 23
<212> TYPE: DNA
<213> ORGANISM: Artificial Sequence
<220> FEATURE:

<223> OTHER INFORMATION: Description of Artificial Sequence: Synthetic primer

<400> SEQUENCE: 102
tttacacacc catccccatg cac 23

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
gaggtacccc gataccaccc cctgca 26

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
agaagcttgg aggtcgcctt ggggcttac 29

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
ttgagtgctg aagcaggctg tgc 23

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
tgcccctcca tccccatgca c 21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
catggggatg gaggggcatt 20

<210> SEQ ID NO 108
<211> LENGTH: 4
<212> TYPE: PRT
<213> ORGANISM: Homo sapiens

<400> SEQUENCE: 108

Tyr Leu Leu Lys
1

<210> SEQ ID NO 109
<211> LENGTH: 5
<212> TYPE: PRT
<213> ORGANISM: Homo sapiens

<400> SEQUENCE: 109

Ala Met Ile Glu Lys
1 5

<210> SEQ ID NO 110
<211> LENGTH: 6
<212> TYPE: PRT
<213> ORGANISM: Homo sapiens

<400> SEQUENCE: 110

Ile Leu Thr Leu Gly Lys
1 5

<210> SEQ ID NO 111

<400> SEQUENCE: 111

000

<210> SEQ ID NO 112
<211> LENGTH: 8
<212> TYPE: PRT
<213> ORGANISM: Homo sapiens

<400> SEQUENCE: 112

His Ser Val Lys Gly Leu Gly Lys
1 5

<210> SEQ ID NO 113
<211> LENGTH: 7
<212> TYPE: PRT
<213> ORGANISM: Homo sapiens

<400> SEQUENCE: 113

Gly Thr Asn Ser Tyr Tyr Lys
1 5

<210> SEQ ID NO 114
<211> LENGTH: 7
<212> TYPE: PRT
<213> ORGANISM: Homo sapiens

<400> SEQUENCE: 114

Leu Leu Trp His Gly Ser Arg
1 5

<210> SEQ ID NO 115
<211> LENGTH: 9
<212> TYPE: PRT
<213> ORGANISM: Homo sapiens

<400> SEQUENCE: 115

Val Gly Thr Val Ile Gly Ser Asn Lys
1 5

<210> SEQ ID NO 116
<211> LENGTH: 7
<212> TYPE: PRT

<213> ORGANISM: Homo sapiens

<400> SEQUENCE: 116

Glu Leu Leu Ile Phe Asn Lys
1 5

<210> SEQ ID NO 117
<211> LENGTH: 9
<212> TYPE: PRT
<213> ORGANISM: Homo sapiens

<400> SEQUENCE: 117

Lys Leu Thr Val Asn Pro Gly Thr Lys
1 5

<210> SEQ ID NO 118
<211> LENGTH: 8
<212> TYPE: PRT
<213> ORGANISM: Homo sapiens

<400> SEQUENCE: 118

Leu Tyr Arg Val Glu Tyr Ala Lys
1 5

<210> SEQ ID NO 119
<211> LENGTH: 10
<212> TYPE: PRT
<213> ORGANISM: Homo sapiens

<400> SEQUENCE: 119

Gly Ile Tyr Phe Ala Asp Met Val Ser Lys
1 5 10

<210> SEQ ID NO 120
<211> LENGTH: 11
<212> TYPE: PRT
<213> ORGANISM: Homo sapiens

<400> SEQUENCE: 120

Thr Leu Gly Asp Phe Ala Ala Glu Tyr Ala Lys
1 5 10

<210> SEQ ID NO 121
<211> LENGTH: 10
<212> TYPE: PRT
<213> ORGANISM: Homo sapiens

<400> SEQUENCE: 121

Asp Ser Glu Glu Ala Glu Ile Ile Arg Lys
1 5 10

<210> SEQ ID NO 122
<211> LENGTH: 10
<212> TYPE: PRT
<213> ORGANISM: Homo sapiens

<400> SEQUENCE: 122

Met Glu Glu Val Lys Glu Ala Asn Ile Arg
1 5 10

<210> SEQ ID NO 123
<211> LENGTH: 10
<212> TYPE: PRT
<213> ORGANISM: Homo sapiens

<400> SEQUENCE: 123

Met Ile Phe Asp Val Glu Ser Met Lys Lys
1 5 10

<210> SEQ ID NO 124
<211> LENGTH: 11
<212> TYPE: PRT
<213> ORGANISM: Homo sapiens

<400> SEQUENCE: 124

Ala Met Val Glu Tyr Glu Ile Asp Leu Gln Lys
1 5 10

<210> SEQ ID NO 125
<211> LENGTH: 13
<212> TYPE: PRT
<213> ORGANISM: Homo sapiens

<400> SEQUENCE: 125

Lys Gly Asp Glu Val Asp Gly Val Asp Glu Val Ala Lys
1 5 10

<210> SEQ ID NO 126
<211> LENGTH: 13
<212> TYPE: PRT
<213> ORGANISM: Homo sapiens

<400> SEQUENCE: 126

Val Phe Ser Ala Thr Leu Gly Leu Val Asp Ile Val Lys
1 5 10

<210> SEQ ID NO 127

<400> SEQUENCE: 127

000

<210> SEQ ID NO 128
<211> LENGTH: 12
<212> TYPE: PRT
<213> ORGANISM: Homo sapiens

<400> SEQUENCE: 128

Ser Lys Leu Pro Lys Pro Val Gln Asp Leu Ile Lys
1 5 10

<210> SEQ ID NO 129
<211> LENGTH: 13
<212> TYPE: PRT
<213> ORGANISM: Homo sapiens

<400> SEQUENCE: 129

Thr Thr Asn Phe Ala Gly Ile Leu Ser Gln Gly Leu Arg
1 5 10

<210> SEQ ID NO 130
<211> LENGTH: 13
<212> TYPE: PRT
<213> ORGANISM: Homo sapiens

<400> SEQUENCE: 130

Gln Gln Val Pro Ser Gly Glu Ser Ala Ile Leu Asp Arg
1 5 10

<210> SEQ ID NO 131
<211> LENGTH: 13

<212> TYPE: PRT
<213> ORGANISM: Homo sapiens

<400> SEQUENCE: 131

Met Ala Ile Met Val Gln Ser Pro Met Phe Asp Gly Lys
1 5 10

<210> SEQ ID NO 132
<211> LENGTH: 14
<212> TYPE: PRT
<213> ORGANISM: Homo sapiens

<400> SEQUENCE: 132

Lys Pro Pro Leu Leu Asn Asn Ala Asp Ser Val Gln Ala Lys
1 5 10

<210> SEQ ID NO 133
<211> LENGTH: 13
<212> TYPE: PRT
<213> ORGANISM: Homo sapiens

<400> SEQUENCE: 133

His Pro Asp Val Glu Val Asp Gly Phe Ser Glu Leu Arg
1 5 10

<210> SEQ ID NO 134
<211> LENGTH: 15
<212> TYPE: PRT
<213> ORGANISM: Homo sapiens

<400> SEQUENCE: 134

Val Val Ser Glu Asp Phe Leu Gln Asp Val Ser Ala Ser Thr Lys
1 5 10 15

<210> SEQ ID NO 135
<211> LENGTH: 14
<212> TYPE: PRT
<213> ORGANISM: Homo sapiens

<400> SEQUENCE: 135

Met Val Asp Pro Glu Lys Pro Gln Leu Gly Met Ile Asp Arg
1 5 10

<210> SEQ ID NO 136
<211> LENGTH: 18
<212> TYPE: PRT
<213> ORGANISM: Homo sapiens

<400> SEQUENCE: 136

Thr Ala Glu Ala Gly Gly Val Thr Gly Lys Gly Gln Asp Gly Ile Gly
1 5 10 15

Ser Lys

<210> SEQ ID NO 137
<211> LENGTH: 14
<212> TYPE: PRT
<213> ORGANISM: Homo sapiens

<400> SEQUENCE: 137

Met Val Asp Pro Glu Lys Pro Gln Leu Gly Met Ile Asp Arg
1 5 10

<210> SEQ ID NO 138
<211> LENGTH: 15
<212> TYPE: PRT

<213> ORGANISM: Homo sapiens

<400> SEQUENCE: 138

Glu Glu Leu Gly Phe Arg Pro Glu Tyr Ser Ala Ser Gln Leu Lys
1 5 10 15

<210> SEQ ID NO 139
<211> LENGTH: 16
<212> TYPE: PRT
<213> ORGANISM: Homo sapiens

<400> SEQUENCE: 139

Ala Met Val Glu Tyr Glu Ile Asp Leu Gln Lys Met Pro Leu Gly Lys
1 5 10 15

<210> SEQ ID NO 140
<211> LENGTH: 16
<212> TYPE: PRT
<213> ORGANISM: Homo sapiens

<400> SEQUENCE: 140

Leu Glu Gln Met Pro Ser Lys Glu Asp Ala Ile Glu His Phe Met Lys
1 5 10 15

<210> SEQ ID NO 141
<211> LENGTH: 20
<212> TYPE: PRT
<213> ORGANISM: Homo sapiens

<400> SEQUENCE: 141

Gly Gly Ala Ala Val Asp Pro Asp Ser Gly Leu Glu His Ser Ala His
1 5 10 15

Val Leu Glu Lys
20

<210> SEQ ID NO 142
<211> LENGTH: 17
<212> TYPE: PRT
<213> ORGANISM: Homo sapiens

<400> SEQUENCE: 142

Asn Arg Glu Glu Leu Gly Phe Arg Pro Glu Tyr Ser Ala Ser Gln Leu
1 5 10 15

Lys

<210> SEQ ID NO 143
<211> LENGTH: 18
<212> TYPE: PRT
<213> ORGANISM: Homo sapiens

<400> SEQUENCE: 143

Val Glu Met Leu Asp Asn Leu Leu Asp Ile Glu Val Ala Tyr Ser Leu
1 5 10 15

Leu Arg

<210> SEQ ID NO 144
<211> LENGTH: 19
<212> TYPE: PRT
<213> ORGANISM: Homo sapiens

<400> SEQUENCE: 144

Ser Leu Gln Glu Leu Phe Leu Ala His Ile Leu Ser Pro Trp Gly Ala
1 5 10 15

-continued

Glu Val Lys

<210> SEQ ID NO 145
<211> LENGTH: 19
<212> TYPE: PRT
<213> ORGANISM: Homo sapiens

<400> SEQUENCE: 145

His Pro Asp Val Glu Val Asp Gly Phe Ser Glu Leu Arg Trp Asp Asp
1 5 10 15

Gln Gln Lys

<210> SEQ ID NO 146
<211> LENGTH: 31
<212> TYPE: PRT
<213> ORGANISM: Homo sapiens

<400> SEQUENCE: 146

Gln Ile Gln Ala Ala Tyr Ser Ile Leu Ser Glu Val Gln Gln Ala Val
1 5 10 15

Ser Gln Gly Ser Ser Asp Ser Gln Ile Leu Asp Leu Ser Asn Arg
20 25 30

<210> SEQ ID NO 147
<211> LENGTH: 32
<212> TYPE: PRT
<213> ORGANISM: Homo sapiens

<400> SEQUENCE: 147

Arg Gln Ile Gln Ala Ala Tyr Ser Ile Leu Ser Glu Val Gln Gln Ala
1 5 10 15

Val Ser Gln Gly Ser Ser Asp Ser Gln Ile Leu Asp Leu Ser Asn Arg
20 25 30

<210> SEQ ID NO 148
<211> LENGTH: 39
<212> TYPE: PRT
<213> ORGANISM: Homo sapiens

<400> SEQUENCE: 148

Ile Phe Pro Pro Glu Thr Ser Ala Ser Val Ala Ala Thr Pro Pro Pro
1 5 10 15

Ser Thr Ala Ser Ala Pro Ala Ala Val Asn Ser Ser Ala Ser Ala Asp
20 25 30

Lys Pro Leu Ser Asn Met Lys
35

<210> SEQ ID NO 149
<211> LENGTH: 1013
<212> TYPE: PRT
<213> ORGANISM: Homo sapiens

<400> SEQUENCE: 149

Ala Glu Ser Ser Asp Lys Leu Tyr Arg Val Glu Tyr Ala Lys Ser Gly
1 5 10 15

Arg Ala Ser Cys Lys Lys Cys Ser Glu Ser Ile Pro Lys Asp Ser Leu
20 25 30

Arg Met Ala Ile Met Val Gln Ser Pro Met Phe Asp Gly Lys Val Pro
35 40 45

His Trp Tyr His Phe Ser Cys Phe Trp Lys Val Gly His Ser Ile Arg
50 55 60

-continued

```
His Pro Asp Val Glu Val Asp Gly Phe Ser Glu Leu Arg Trp Asp Asp
65                  70                  75                  80

Gln Gln Lys Val Lys Lys Thr Ala Glu Ala Gly Gly Val Thr Gly Lys
                85                  90                  95

Gly Gln Asp Gly Ile Gly Ser Lys Ala Glu Lys Thr Leu Gly Asp Phe
            100                 105                 110

Ala Ala Glu Tyr Ala Lys Ser Asn Arg Ser Thr Cys Lys Gly Cys Met
        115                 120                 125

Glu Lys Ile Glu Lys Gly Gln Val Arg Leu Ser Lys Lys Met Val Asp
    130                 135                 140

Pro Glu Lys Pro Gln Leu Gly Met Ile Asp Arg Trp Tyr His Pro Gly
145                 150                 155                 160

Cys Phe Val Lys Asn Arg Glu Glu Leu Gly Phe Arg Pro Glu Tyr Ser
                165                 170                 175

Ala Ser Gln Leu Lys Gly Phe Ser Leu Leu Ala Thr Glu Asp Lys Glu
            180                 185                 190

Ala Leu Lys Lys Gln Leu Pro Gly Val Lys Ser Glu Gly Lys Arg Lys
        195                 200                 205

Gly Asp Glu Val Asp Gly Val Asp Glu Val Ala Lys Lys Lys Ser Lys
    210                 215                 220

Lys Glu Lys Asp Lys Asp Ser Lys Leu Glu Lys Ala Leu Lys Ala Gln
225                 230                 235                 240

Asn Asp Leu Ile Trp Asn Ile Lys Asp Glu Leu Lys Lys Val Cys Ser
                245                 250                 255

Thr Asn Asp Leu Lys Glu Leu Leu Ile Phe Asn Lys Gln Gln Val Pro
            260                 265                 270

Ser Gly Glu Ser Ala Ile Leu Asp Arg Val Ala Asp Gly Met Val Phe
        275                 280                 285

Gly Ala Leu Leu Pro Cys Glu Glu Cys Ser Gly Gln Leu Val Phe Lys
    290                 295                 300

Ser Asp Ala Tyr Tyr Cys Thr Gly Asp Val Thr Ala Trp Thr Lys Cys
305                 310                 315                 320

Met Val Lys Thr Gln Thr Pro Asn Arg Lys Glu Trp Val Thr Pro Lys
                325                 330                 335

Glu Phe Arg Glu Ile Ser Tyr Leu Lys Lys Leu Lys Val Lys Lys Gln
            340                 345                 350

Asp Arg Ile Phe Pro Pro Glu Thr Ser Ala Ser Val Ala Ala Thr Pro
        355                 360                 365

Pro Pro Ser Thr Ala Ser Ala Pro Ala Ala Val Asn Ser Ser Ala Ser
    370                 375                 380

Ala Asp Lys Pro Leu Ser Asn Met Lys Ile Leu Thr Leu Gly Lys Leu
385                 390                 395                 400

Ser Arg Asn Lys Asp Glu Val Lys Ala Met Ile Glu Lys Leu Gly Gly
                405                 410                 415

Lys Leu Thr Gly Thr Ala Asn Lys Ala Ser Leu Cys Ile Ser Thr Lys
            420                 425                 430

Lys Glu Val Glu Lys Met Asn Lys Lys Met Glu Glu Val Lys Glu Ala
        435                 440                 445

Asn Ile Arg Val Val Ser Glu Asp Phe Leu Gln Asp Val Ser Ala Ser
    450                 455                 460

Thr Lys Ser Leu Gln Glu Leu Phe Leu Ala His Ile Leu Ser Pro Trp
465                 470                 475                 480

Gly Ala Glu Val Lys Ala Glu Pro Val Glu Val Val Ala Pro Arg Gly
                485                 490                 495
```

-continued

```
Lys Ser Gly Ala Ala Leu Ser Lys Lys Ser Lys Gly Gln Val Lys Glu
                500                 505                 510

Glu Gly Ile Asn Lys Ser Glu Lys Arg Met Lys Leu Thr Leu Lys Gly
        515                 520                 525

Gly Ala Ala Val Asp Pro Asp Ser Gly Leu Glu His Ser Ala His Val
    530                 535                 540

Leu Glu Lys Gly Gly Lys Val Phe Ser Ala Thr Leu Gly Leu Val Asp
545                 550                 555                 560

Ile Val Lys Gly Thr Asn Ser Tyr Tyr Lys Leu Gln Leu Leu Glu Asp
                565                 570                 575

Asp Lys Glu Asn Arg Tyr Trp Ile Phe Arg Ser Trp Gly Arg Val Gly
                580                 585                 590

Thr Val Ile Gly Ser Asn Lys Leu Glu Gln Met Pro Ser Lys Glu Asp
        595                 600                 605

Ala Ile Glu His Phe Met Lys Leu Tyr Glu Glu Lys Thr Gly Asn Ala
    610                 615                 620

Trp His Ser Lys Asn Phe Thr Lys Tyr Pro Lys Lys Phe Tyr Pro Leu
625                 630                 635                 640

Glu Ile Asp Tyr Gly Gln Asp Glu Glu Ala Val Lys Lys Leu Thr Val
                645                 650                 655

Asn Pro Gly Thr Lys Ser Lys Leu Pro Lys Pro Val Gln Asp Leu Ile
                660                 665                 670

Lys Met Ile Phe Asp Val Glu Ser Met Lys Lys Ala Met Val Glu Tyr
        675                 680                 685

Glu Ile Asp Leu Gln Lys Met Pro Leu Gly Lys Leu Ser Lys Arg Gln
    690                 695                 700

Ile Gln Ala Ala Tyr Ser Ile Leu Ser Glu Val Gln Gln Ala Val Ser
705                 710                 715                 720

Gln Gly Ser Ser Asp Ser Gln Ile Leu Asp Leu Ser Asn Arg Phe Tyr
                725                 730                 735

Thr Leu Ile Pro His Asp Phe Gly Met Lys Lys Pro Pro Leu Leu Asn
                740                 745                 750

Asn Ala Asp Ser Val Gln Ala Lys Val Glu Met Leu Asp Asn Leu Leu
        755                 760                 765

Asp Ile Glu Val Ala Tyr Ser Leu Leu Arg Gly Gly Ser Asp Asp Ser
    770                 775                 780

Ser Lys Asp Pro Ile Asp Val Asn Tyr Glu Lys Leu Lys Thr Asp Ile
785                 790                 795                 800

Lys Val Val Asp Arg Asp Ser Glu Glu Ala Glu Ile Ile Arg Lys Tyr
                805                 810                 815

Val Lys Asn Thr His Ala Thr Thr His Asn Ala Tyr Asp Leu Glu Val
                820                 825                 830

Ile Asp Ile Phe Lys Ile Glu Arg Glu Gly Glu Cys Gln Arg Tyr Lys
        835                 840                 845

Pro Phe Lys Gln Leu His Asn Arg Arg Leu Leu Trp His Gly Ser Arg
    850                 855                 860

Thr Thr Asn Phe Ala Gly Ile Leu Ser Gln Gly Leu Arg Ile Ala Pro
865                 870                 875                 880

Pro Glu Ala Pro Val Thr Gly Tyr Met Phe Gly Lys Gly Ile Tyr Phe
                885                 890                 895

Ala Asp Met Val Ser Lys Ser Ala Asn Tyr Cys His Thr Ser Gln Gly
                900                 905                 910

Asp Pro Ile Gly Leu Ile Leu Leu Gly Glu Val Ala Leu Gly Asn Met
```

-continued

```
        915                 920                 925

Tyr Glu Leu Lys His Ala Ser His Ile Ser Lys Leu Pro Lys Gly Lys
    930                 935                 940

His Ser Val Lys Gly Leu Gly Lys Thr Thr Pro Asp Pro Ser Ala Asn
945                 950                 955                 960

Ile Ser Leu Asp Gly Val Asp Val Pro Leu Gly Thr Gly Ile Ser Ser
                965                 970                 975

Gly Val Asn Asp Thr Ser Leu Leu Tyr Asn Glu Tyr Ile Val Tyr Asp
            980                 985                 990

Ile Ala Gln Val Asn Leu Lys Tyr  Leu Leu Lys Leu Lys  Phe Asn Phe
        995                 1000                1005

Lys Thr  Ser Leu Trp
    1010


<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150

agcacaatac ggctttgagt g                                                21


<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151

ctccatcccc atgcacac                                                    18


<210> SEQ ID NO 152
<211> LENGTH: 168
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152

aaaaaaagga aaaaaagcac aataaaaaat tgaaaaaagc aaaaatgcaa aaaaagataa     60

aataaaaaat ttaaaacaat ttaaaaaaaa aaaaaaaaac aaaaaaaaaa ataaaataaa    120

aaaaaaagga tggaaaaaaa aaaaaaaaaa aaaaaattta aaaaacct                 168


<210> SEQ ID NO 153
<211> LENGTH: 39
<212> TYPE: DNA
<213> ORGANISM: Homo sapiens

<400> SEQUENCE: 153

cccttttga gcctcaattt ccccacctgt caacagcag                              39


<210> SEQ ID NO 154
<211> LENGTH: 24
<212> TYPE: DNA
<213> ORGANISM: Homo sapiens

<400> SEQUENCE: 154
```

-continued

```
gcctcaattt ccccacctgt caac                                              24


<210> SEQ ID NO 155
<211> LENGTH: 24
<212> TYPE: DNA
<213> ORGANISM: Homo sapiens

<400> SEQUENCE: 155

tttgagcctc aatttcccca cctg                                              24
```